United States Patent [19]
Cardinal et al.

[11] Patent Number: 5,698,220
[45] Date of Patent: Dec. 16, 1997

[54] ASYMMETRIC MEMBRANES IN DELIVERY DEVICES

[75] Inventors: John R. Cardinal, Old Lyme, Conn.; Scott M. Herbig, Bend, Oreg.; Richard W. Korsmeyer, East Lyme; Jeelin Lo, Old Lyme, both of Conn.; Kelly L. Smith, Bend, Oreg.; Avinash G. Thombre, Gales Ferry, Conn.

[73] Assignee: Pfizer Inc., New York, N.Y.

[21] Appl. No.: 462,473

[22] Filed: Jun. 5, 1995

Related U.S. Application Data

[62] Division of Ser. No. 951,931, Sep. 25, 1992, Pat. No. 5,612,059, which is a continuation of Ser. No. 391,741, Aug. 9, 1989, abandoned, which is a continuation-in-part of Ser. No. 238,371, Aug. 30, 1988, abandoned.

[51] Int. Cl.$^6$ .................. A61K 9/62; A61K 9/36
[52] U.S. Cl. .............. 424/451; 424/461; 424/463; 424/464; 424/480; 424/489; 424/494; 424/495
[58] Field of Search ................... 424/451, 463, 424/461, 464, 480, 489, 494, 495

[56] References Cited

U.S. PATENT DOCUMENTS

| | | | |
|---|---|---|---|
| 3,133,132 | 5/1964 | Loeb et al. | 264/49 |
| 3,538,214 | 11/1970 | Polli et al. | 424/19 |
| 3,615,536 | 10/1971 | Williams, Jr. | 430/390 |
| 3,845,770 | 11/1974 | Theeuwes et al. | 128/260 |
| 3,884,801 | 5/1975 | Kesting | 210/23 |
| 3,952,741 | 4/1976 | Baker | 128/266 |
| 3,977,404 | 8/1976 | Theeuwes | 424/427 |
| 3,995,631 | 12/1976 | Higuchi et al. | 128/266 |
| 4,016,880 | 4/1977 | Theeuwes et al. | 128/260 |
| 4,160,020 | 7/1979 | Ayers et al. | 424/15 |
| 4,160,452 | 7/1979 | Theeuwes et al. | 128/260 |
| 4,203,439 | 5/1980 | Theeuwes | 128/260 |
| 4,235,236 | 11/1980 | Theeuwes | 128/260 |

(List continued on next page.)

FOREIGN PATENT DOCUMENTS

| | | |
|---|---|---|
| 1980276 | 11/1976 | Australia . |
| 1718076 | 2/1978 | Australia . |
| 2255777 | 8/1978 | Australia . |
| 2878077 | 3/1979 | Australia . |
| 3098677 | 5/1979 | Australia . |
| 1785483 | 2/1984 | Australia . |
| 2251183 | 11/1984 | Australia . |
| 5514086 | 9/1986 | Australia . |
| 6078086 | 2/1987 | Australia . |
| 6203386 | 3/1987 | Australia . |
| 6529686 | 5/1987 | Australia . |
| 6532586 | 5/1987 | Australia . |
| 7071487 | 10/1987 | Australia . |
| 7369287 | 12/1987 | Australia . |
| 1252731 | 3/1989 | Canada . |
| 0056825 | 4/1982 | European Pat. Off. . |
| 0168862 | 1/1986 | European Pat. Off. . |
| 0171457 | 2/1986 | European Pat. Off. . |
| 0200386 | 8/1984 | New Zealand . |
| 0192532 | 10/1984 | New Zealand . |

(List continued on next page.)

OTHER PUBLICATIONS

R. E. Kesting "Synthetic Polymeric Membranes", Wiley–Interscience, 2nd Ed., 1985. (Chapters 3 and 8)).
R. E. Kesting "Synthetic Polymeric Membranes", McGraw–Hill, 1971.(Chapters 4 and 5).
Desalination, vol. 35, pp. 39–58; Amsterdam, Netherlands; H. Strathmann: Development of New Membranes (1980).
Remington's Pharmaceutical Science, pp. 1633–1639 (1988).
R. E. Kesting "Synthetic Polymeric Membranes", Wiley–Interscience, 2nd Ed., 1985. (Chapter 7) Remington's Pharmaceutical Science, pp. 1633–1639 (1988).

*Primary Examiner*—Jyothsan Venkat
*Attorney, Agent, or Firm*—Peter C. Richardson; Gregg C. Benson; A. Dean Olson

[57] ABSTRACT

A device for controlled release of an active substance through one or more asymmetric membranes by diffusion and/or osmotic pumping.

50 Claims, 44 Drawing Sheets

Example 1. SEM (Scanning Electron Microscope) Cross Section of an Asymmetric Membrane Tablet Coating
1 cm = 50 μm.

U.S. PATENT DOCUMENTS

| | | | |
|---|---|---|---|
| 4,333,972 | 6/1982 | Kesting | 427/244 |
| 4,439,196 | 3/1984 | Higuchi | 604/890 |
| 4,455,143 | 6/1984 | Theeuwes et al. | 128/260 |
| 4,483,846 | 11/1984 | Koide et al. | 424/19 |
| 4,557,925 | 12/1985 | Lindahl et al. | 424/19 |
| 4,609,374 | 9/1986 | Ayer | 664/892 |
| 4,629,619 | 12/1986 | Lindahl et al. | 424/15 |
| 4,629,620 | 12/1986 | Lindahl et al. | 424/15 |
| 4,673,405 | 6/1987 | Guittard et al. | 604/890 |
| 4,687,660 | 8/1987 | Baker et al. | 424/465 |
| 4,693,896 | 9/1987 | Wheatley et al. | 424/480 |
| 4,732,586 | 3/1988 | Dick et al. | 55/158 |
| 4,784,858 | 11/1988 | Ventouras | 424/468 |
| 4,786,500 | 11/1988 | Wong | 424/422 |
| 4,803,076 | 2/1989 | Ranade | 424/438 |
| 4,824,678 | 4/1989 | Lindahl et al. | 424/473 |
| 4,828,705 | 5/1989 | Thakore et al. | 210/636 |
| 4,837,111 | 6/1989 | Deters et al. | 424/473 |
| 4,849,457 | 7/1989 | Ichii et al. | 521/62 |

FOREIGN PATENT DOCUMENTS

| | | |
|---|---|---|
| 0204438 | 5/1985 | New Zealand . |
| 0200519 | 8/1985 | New Zealand . |
| 0214635 | 11/1985 | New Zealand . |
| 0202095 | 5/1986 | New Zealand . |
| 0210310 | 1/1988 | New Zealand . |
| 0217696 | 5/1989 | New Zealand . |
| 0217024 | 7/1989 | New Zealand . |
| 0222107 | 7/1989 | New Zealand . |
| 0218297 | 3/1990 | New Zealand . |

Example 1. SEM (Scanning Electron Microscope) Cross Section of an Asymmetric Membrane Tablet Coating. 1 cm = 50 μm.

Example 2. SEM Cross Section of an Asymmetric Membrane Tablet Coating.
1 cm = 10 μm.

Example 3. SEM of a Cross Section of an Asymmetric Membrane Tablet Coating.
1 cm = 10 μm.

Example 4. Release of Trimazosin into Water From Tablets Coated With Dense and Asymmetric Membrane Coatings.

Example 6. Release Rate of Trimazosin From Tablets Placed Alternately into a 2.4-wt% MgSO$_4$ Solution, Then Water, and Then a 2.4-wt% MgSO$_4$ Solution. Three replicates.

Example 8. Effect of Formamide Content of Membrane-Coating Solution on Release Rate.

Tablet core: 40 wt% Trimazosin, 58 wt% Avicel pH 102, 2 wt% magnesium stearate 350 mg total.

Coating solution: 15 wt% CA 398-10, 7 to 35 wt% formamide, acetone. Coating weights were proportional to formamide content within the range from 9.7 mg/tablet at 7% formamide to 17 mg/tablet at 35% formamide.

Reference: BRI 454-75, 76,465-20, 55-57, 60

Example 10. Release of Doxazosin With Respect to the Osmotic Driving Force.

Example 11. SEM of the Surface of Asymmetric Membrane Coating. 1% (weight) glycerol in coating solution. 1 cm = 14 μm.

Example 11. SEM of the Surface of an Asymmetric
Membrane Coating. 5% (weight) glycerol in the coating solution.
1 cm = 10 μm.

Example 11. SEM of the Surface of an Asymmetric Membrane Coating. 10% (weight) glycerol in the coating solution. 1 cm = 10 μm.

Example 11. SEM of the Surface of Asymmetric Membrane Coating. 20% (weight) glycerol in the coating solution. 1 cm = 10 μm.

Example 12. SEM of the Surface of an Asymmetric Coating. 5% (weight) sodium acetate in the coating solution. 1 cm = 14 μm.

Example 15. SEM of a Cross Section of an Asymmetric Membrane Capsule Wall. 1 cm = 50 μm.

Example 16. Release of Doxazosin From Asymmetric Membrane Capsules into Gastric Buffer (7.5 atm) and Dextrose Solutions (21 atm and 34 atm) at 37°C Capsule forming solution: 17% CA/30% ethanol/53% acetone
Capsule loading: 1% Doxazosin, 10% Adipic acid, 89% lactose—250 mg total Example 18. SEM of an Asymmetric Membrane Capsule Wall with Macropores Through the Surface. 1 cm = 50 μm.

Example 20. SEM of a Cross Section of an Asymmetric Membrane Coating on a Non-Pareil Bead. 1 cm = 10 μm.

Example 21. SEM of a Cross Section of a "Triple Coated" Asymmetric Membrane Coating on a Bead.
1 cm = 14 μm.

Example 21. Release of Doxazosin From Coated Beads (1 to 3 coats) into a Lactose Solution.

Example 22. Release of Doxazosin From Triple-Coated Beads into Receptor Solutions with Different Osmotic Pressures Beads: 5 wt% Doxazosin, 15 wt% Avicel, 71 wt% lactose, 9 wt% adipic acid, 2 wt% precoat (Sucrose/HPMC)

Example 23. SEM of the Surface of an Asymmetric Membrane Coating on a Bead with Macropores Through the Surface. 1 cm = 14 μm.

Example 24. Release of Trimazosin Beads Formulated in Asymmetric Cellulose Acetate Beads (diameter 2 to 3 mm) Formed by the Quench Process.

Coating solution: 15 wt% CA, 33 wt% ethanol, 52 wt% acetone

Example 27. SEM of a Cross Section of an Asymmetric Membrane Capsule Wall Made of Ethylcellulose.
5 cm = 100 μm.

Example 28. SEM of a Cross Section of an Asymmetric Membrane Capsule Wall Made of Cellulose Acetate Butyrate. 2.5 cm = 200 μm.

Example 29. SEM of a Cross Section of an Asymmetric Membrane Capsule Wall Made of a Blend of Ethylcellulose and Cellulose Acetate. 2.5 cm = 20 μm.

Example 30. SEM of a Cross Section of an Asymmetric Membrane Capsule Wall Made of a Blend of Cellulose Acetate Butyrate and Ethylcellulose.
3.75 cm = 200 μm.

Example 31. SEM of a Cross Section of an Asymmetric Membrane Capsule Wall Made of a Blend of Cellulose Acetate Butyrate and Cellulose Acetate.
3.5 cm = 10 μm.

Example 32. SEM of a Cross Section of an Asymmetric Membrane Capsule Wall Made of Cellulose Acetate Propionate. 5.25 cm = 500 μm.

Example 33. SEM of a Cross Section of an Asymmetric Membrane Capsule Wall Made of Nitrocellulose.
4 cm = 200 μm Example 34. SEM of a Cross Section of an Asymmetric Membrane Capsule Wall Made of Cellulose Acetate Phthalate. 4 cm = 100 μm.

Example 35. SEM of a Cross Section of an Asymmetric Membrane Capsule Wall Made of Cellulose Acetate Trimellitate. 4 cm = 200 μm.

Example 36. SEM of a Cross Section of an Asymmetric Membrane Capsule Wall Made of Polyvinyl Alcohol. 4 cm = 200 μm.

Example 37. SEM of a Cross Section of an Asymmetric Membrane Capsule Wall Made of Ethylenevinyl Alcohol. 4.5 cm = 200 μm.

200 μm

Example 38. SEM of a Cross Section of an Asymmetric Membrane Capsule Wall Made of Polyurethane.
5 cm = 200 μm.

Example 39. SEM of a Cross Section of an Asymmetric Membrane Capsule Wall Made of Polyvinylidene Fluoride. 4.5 cm = 50 μm.

100 μm

Example 40. SEM of a Cross Section of an Asymmetric Membrane Capsule Wall Made of Polysulfone.
4.5 cm = 100 μm.

Example 41. SEM of a Cross Section of an Asymmetric Membrane Capsule Wall Made of Polymethyl Methacrylate. 3.5 cm = 20 μm.

50 μm

Example 42. SEM of a Cross Section of an Asymmetric Membrane Capsule Wall Made of Polyamide.
4.5 cm = 50 μm.

Example 43. SEM of a Cross Section of an Asymmetric Membrane Capsule Wall Made With a Blend of Ethylcellulose and Cellulose Acetate Phthalate.
4.5 cm = 200 μm.

200 μm

Example 44. SEM of a Cross Section of an Asymmetric Membrane Capsule Wall Made With a Blend of Ethylcellulose and Cellulose Acetate Trimellitate.
4 cm = 200 μm.

10 μm

Example 45. SEM of a Cross Section of an Asymmetric Membrane Wall Made of Ethylcellulose on a Drug Containing Bead.
3.5 cm = 10 μm.

Example 46. SEM of a Cross Section of an Asymmetric Membrane Wall Made of a Cellulose Acetate Butyrate on a Drug Containing Bead.
3 cm = 20 μm.

Example 47. Water Fluxes and Corresponding Release Rates from Asymmetric Membrane Capsules.

Example 49. SEM of Cross Section of Multiple Layers of Asymmetric Membranes Made of Cellulose Acetate on Beads.

ASYMMETRIC MEMBRANES IN DELIVERY DEVICES

This application is a divisional of U.S. application Ser. No. 07/951,931 filed on Sep. 25, 1992 now U.S. Pat. No. 5,612,059 which is a continuation of application Ser. No. 07/391,741 filed on Aug. 9, 1989, now abandoned, which was a continuation-in-part of application Ser. No. 07/238,371 filed on Aug. 30, 1988, now abandoned. The priority of all such applications is hereby claimed.

BACKGROUND OF THE INVENTION

Asymmetric membranes, which consist of a very thin, dense skin supported by a thicker, porous sub-structure layer, are used extensively in the reverse-osmosis desalination of brine. The technology for the formation of economically feasible asymmetric membranes for reverse osmosis was developed by Loeb and Sourirajan [Adv. Chem. Ser. 38, 117 (1962)] and continues to be improved.

Asymmetric membranes of polyquinoxalines have been employed in the separation of gaseous mixtures (U.S. Pat. No. 4,732,586).

While the literature is replete with descriptions of tablets, capsules and multiparticulates which deliver active substances by diffusion or osmotic pumping, none have taught the use of delivering active substances using a device with a coating comprised of an asymmetric membrane.

SUMMARY OF THE INVENTION

It has now been found that a device for controlled release of one or more active substances into an environment of use, said device comprising a core of said substances, with or without one or more excipients, surrounded by one or more asymmetric membranes is feasible and practical.

A preferred feature of the device is a membrane which is permeable and imperforate and where the release is either substantially by osmotic pumping or substantially by diffusion.

A second preferred feature of the device is a membrane which is permeable and perforate and where the release is either substantially osmotic pumping or substantially by diffusion.

A third preferred feature is a device in which the asymmetric membrane is a cellulose ester or ethyl cellulose.

A fourth preferred feature is a device in the form of a tablet, capsule or bead.

A fifth preferred feature is a device having a membrane which is semipermeable and imperforate, where the release is substantially osmotic pumping and the device is in the form of a capsule, tablet or bead.

The present invention also includes a tablet, capsule or bead for administration to an animal which releases one or more pharmaceutically active substances into said animal over an appreciable time interval which comprises a core of said active substance or substances, with or without one or more pharmaceutically acceptable excipients, said core being surrounded by one or more asymmetric membranes.

A preferred feature is a tablet, capsule or bead, wherein the administration is oral and the release is into the fluid of the gastrointestinal tract of said animal.

Preferred is a tablet, capsule or bead wherein the active substance is an antihypertensive agent. Especially preferred are prazosin, nifedipine, trimazosin and doxazosin.

Also preferred is a tablet, capsule or bead wherein the active substance is an antianxiety agent. Especially preferred are hydroxyzine and sertraline.

Also preferred is a tablet, capsule or bead wherein the active substance is an anticlotting agent. Especially preferred is dazmergrel.

Also preferred is a tablet, capsule or bead wherein the active substance is a hypoglycemic agent. Especially preferred is glipizide.

Also preferred is a tablet, capsule or bead wherein the active substance is a decongestant, an antihistamine or cough or cold agent. Especially preferred are brompheniramine, dexbrompheniramine and chlorpheniramine maleates, phenylephrine and pseudoephedrine hydrochlorides and cetirizine.

The present invention also includes a process for preparing a tablet for controlled release of one or more active substances into an environment of use, said tablet comprised of a core of said active substances, with or without one or more excipients, surrounded by an asymmetric membrane wherein said membrane is formed by a phase inversion process.

Preferred is a wet process which comprises the steps of:
a) coating said core with a solution comprised of about 10–20% of a cellulose ester or ethyl cellulose by weight and, optionally, about 0–35% of one or more pore-forming substances by weight in acetone,
b) immersing the coated core into an aqueous quench bath and
c) drying.

Preferred in this process is the use of cellulose acetate 398-10 present in the amount of 15% by weight and the pore-forming substances are formamide, acetic acid, glycerol, a ($C_1$–$C_4$)alkanol, sodium acetate, aqueous hydrogen peroxide or polyvinylpyrrolidone. Especially preferred is the use of ethanol as a pore-forming agent, present in the amount of 30% by weight or the use of glycerol as a pore-forming agent, present in the amount of 10% by weight.

A second preferred wet process for preparing tablets comprises the steps of:
a) coating said core with a solution comprised of abut 10–20% of a cellulose ester or ethyl cellulose by weight and, optionally, about 0–40% of one or more pore-forming substances by weight in acetone,
b) immersing the coated core into water until the membrane has solidified,
c) immersing the coated core into isopropanol until the water has been replaced by isopropanol,
d) immersing the coated core in hexane until the isopropanol has been replaced by hexane and drying.

Preferred in this process is the use of cellulose acetate 398-10 present in the amount of 15% by weight and the pore-forming substances are formamide, acetic acid, glycerol, a ($C_1$–$C_4$)alkanol, sodium acetate, aqueous hydrogen peroxide or polyvinylpyrrolidone. Especially preferred is the use of ethanol, as a pore-forming agent, present in the amount of 30% by weight.

Another preferred phase inversion process for preparing tablets is a dry process comprising the steps of:
a) coating said core with a solution comprised of 10–20% of a cellulose ester or ethyl cellulose by weight and about 20–40% of one or more pore-forming substances by weight in acetone and
b) drying the tablet.

Preferred in this process is the use of cellulose acetate 398-10 present in the amount of 15% by weight and the pore-forming substances are comprised of glycerol, water, butanol and ethanol present in the amount of 1.9, 2.7, 11.7 and 21.7%, respectively, by weight.

Also part of the present invention is a process for preparing a capsule for controlled release of one or more active substances into an environment of use, said capsule comprised of a core of said active substances, with or without one or more excipients, surrounded by an asymmetric membrane, wherein said membrane is formed by a phase inversion process.

Preferred is a wet process which comprises the steps of:
a) coating a mandrel device, sized and shaped to match the inner dimensions of the desired capsule, with a solution comprised of about 10–20% of a cellulose ester or ethyl cellulose by weight and, optionally, about 0–40% of one or more pore-forming substances by weight in acetone,
b) immersing the coated device into an aqueous quench bath,
c) drying,
d) removing the capsule shell from the device,
e) filling the capsule shell with the core material and
f) sealing the capsule.

Preferred in this process is the use of cellulose acetate 398-10 present in the amount of 16% by weight and the pore-forming substance is formamide, acetic acid, glycerol, a $(C_1-C_4)$alkanol, sodium acetate, aqueous hydrogen peroxide or polyvinylpyrrolidone. Especially preferred is the use of ethanol and glycerol as pore-forming substances, present in the amount of 28 and 8%, respectively, by weight. Also especially preferred is the use of glycerol as the pore-forming substance, present in the amount of 10% by weight.

Also part of the present invention is a process for preparing beads for controlled release of one or more active substances into an environment of use, said beads comprised of a core of said active substances, with or without one or more excipients, surrounded by an asymmetric membrane wherein said membrane is formed by a phase inversion process.

Preferred is a dry process comprising the steps of:
a) spray drying a slurry of said active substances in the form of beads coated with a solution comprised of about 10–20% of a cellulose ester or ethyl cellulose by weight and about 20–40% of one or more pore-forming substances by weight in acetone into a chamber maintained at about 25°–95° C., and
b) separating the dried beads from any excess polymer by sieving or by using cyclones.

Preferred within this process is the use of a pore-forming mixture comprising 38% by weight of the total and composed of ethanol, butanol, water and glycerol present in the amount of 57, 31, 7 and 5%, respectively, by weight, and the cellulose ester is cellulose acetate 398-10 present in the amount of 15% by weight. Especially preferred is the spray drying under a pressure of 10–100 psi above atmospheric pressure into a chamber at atmospheric pressure.

Also preferred within this process for preparing beads is a wet process which comprises the steps of:
a) coating said core of active substances in the form of beads with a solution comprised of about 10–20% of a cellulose ester or ethyl cellulose by weight and, optionally, about 0–40% of one or more pore-forming substances by weight in acetone,
b) immersing the coated beads into an aqueous quench bath,
c) removing the beads after the membrane has solidified and drying.

Preferred in this process is the use of cellulose acetate 398-10 present in the amount of 15% and the pore-forming substance is ethanol present in the amount of 33% by weight.

The present invention also relates to a method for releasing one or more active substances into an environment of use which comprises placing in said environment a device containing said active substances surrounded by an asymmetric membrane.

Preferred in this method is a device which is a tablet, capsule or bead. Especially preferred is said device wherein the membrane is permeable and imperforate or perforate, and the release is substantially either by diffusion or osmotic pumping. Also especially preferred is said device wherein the membrane is semipermeable and imperforate and the release is substantially osmotic pumping.

The present invention also relates to a capsule device for the controlled release of one or more active substances into an environment of use, said device comprising a core of said substances, with or without excipients, enclosed in a capsule the top or bottom of which is comprised of one or more asymmetric membranes. Preferred is said device wherein the membrane is permeable and perforate or imperforate. Especially preferred is such a device wherein the release is by osmotic pumping.

Finally, the instant invention relates to a process for preparing a capsule shell to be used for controlled release of one or more active substances into an environment of use, said shell comprised of an asymmetric membrane, wherein said membrane is formed by a phase inversion process.

Preferred is a wet process which comprises the steps of:
a) coating a mandrel device, sized and shaped to match the inner dimensions of the desired capsule, with a solution comprised of about 10–20% of a cellulose ester or ethyl cellulose by weight and, optionally, about 0–40% of one or more pore-forming substances by weight in acetone,
b) immersing the coated device into an aqueous quench bath,
c) drying and
d) removing the capsule shell from the device.

Preferred in this process is the use of cellulose acetate 398-10 present in the amount of 16% by weight and the pore-forming substance is formamide, acetic acid, glycerol, a $(C_1-C_4)$alkanol, sodium acetate, aqueous hydrogen peroxide or polyvinylpyrrolidone. Especially preferred is the use of ethanol and glycerol as pore-forming substances, present in the amount of 28 and 8%, respectively, by weight. Also especially preferred is the use of glycerol as the pore-forming substance, present in the amount of 10% by weight.

The present invention also relates to a process for preparing a bead, tablet or capsule device for controlled release of one or more active substances into an environment of use, said device comprised of a core of said active substances, with or without excipients, surrounded by more than one asymmetric membrane wherein said membranes are formed by a phase inversion process.

Preferred is a dry process comprising spray coating of said device suspended in the temperature controlled air flow of a fluidized bed coating system with a solution comprised of about 5–10% of a cellulose ester or ethyl cellulose by weight and about 35–40% of one or more pore-forming substances by weight in acetone until the desired number of asymmetric membranes have been applied. Especially preferred is the use of ethanol as the pore-former and cellulose acetate 398-10 as the membrane material.

The present invention also includes a process for preparing a tablet for controlled release of one or more active substances into an environment of use, said tablet comprised of a core of said active substances, with or without one or more excipients, surrounded by an asymmetric membrane wherein said membrane is formed by a phase inversion process.

Preferred is a dry process comprising spray coating said core in a perforated pan coating machine with a solution comprised of about 10–15% of a cellulose ester or ethyl cellulose by weight and about 20–40% of one or more pore-forming substances by weight in acetone. Especially preferred is the use of cellulose acetate 398-10 and glycerol, water, butanol and ethanol together as pore-formers in the amount of 2, 2.8, 12.4 and 22% by weight, respectively.

DETAILED DESCRIPTION OF THE INVENTION

Figure 1:
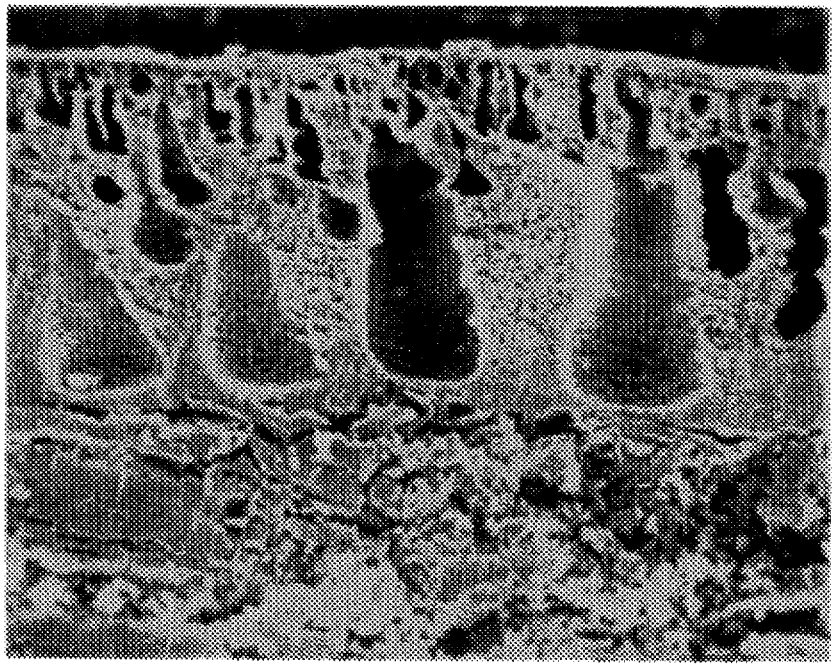
FIG. 1 shows the SEM (scanning electron microscope) cross section of an asymmetric membrane tablet coating having a dense imperforate skin prior to use. The membrane was prepared according to the procedure of Example 1, employing a phase inversion-wet process and using cellulose acetate as the membrane material and formamide as the pore-forming substance.

As previously indicated, an asymmetric membrane is comprised of two regions or membrane layers. The substructure is relatively thick and very porous in nature. This substructure supports the other portion of the membrane, a very dense, thin skin.

The materials of which the asymmetric membranes of the present invention are made consist of cellulose derivatives. In particular, they consist of cellulose esters and ethers, namely, the mono-, di- and triacyl esters wherein the acyl group consists of two to four carbon atoms and lower alkyl ethers of cellulose wherein the alkyl group is of one to four carbon atoms. The cellulose esters can also be mixed esters, such as cellulose acetate butyrate, or a blend of cellulose esters. The same variations can be found in ethers of cellulose and includes blends of cellulose esters and cellulose ethers. Other cellulose derivatives which can be used in making the asymmetric membranes of the present invention include those materials which are associated with reverse osmosis membranes, and include cellulose nitrate, acetaldehyde dimethyl cellulose, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate p-toluene sulfonate, cellulose cyanoacetates, cellulose acetate trimellitate and cellulose methacrylates.

These materials can be formed by the acylation of cellulose with the corresponding acyl anhydride or acyl halide.

Several of the common cellulose esters are available commercially. cellulose acetate 394-60, 398-10 and 400-25, having acetyl contents of 39.4, 39.8 and 40%, respectively, are readily available from Eastman Chemical Co., Kingsport, Tenn.

In addition to cellulose derivatives, materials useful for fabricating asymmetric membranes include polysulfones, polyamides, polyurethanes, polypropylene, ethylene-vinyl acetate, polyvinyl chloride, polyvinyl alcohol, ethylenevinyl alcohol, polyvinylidene fluoride, polymethyl methacrylate as well as many others.

As mentioned, it has now been found that tablets and multiparticulates or beads can be coated with an asymmetric membrane and capsule shells can be made of an asymmetric membrane for release of one or more active substances in an environment of use over a period of time.

The process by which this membrane is formed is a phase inversion process (R. E. Kesting, "Synthetic Polymeric Membranes," Wiley-Interscience, 2nd Ed., 1985). In this process a polymer solution is induced to undergo phase separation in a particular way, resulting in a structured, continuous polymer phase. In preparing the membrane of the present invention the process can be a wet process or a dry process. In the wet process the polymer is dissolved in a solvent system consisting of one or more solvents. A film of this solution is coated on a delivery device, in particular a tablet, bead or capsule form, and following an optional period of air drying, the coated device is immersed in a quench bath consisting of a solvent in which the polymer is not soluble, but in which the original polymer solvent system is soluble. The quench bath extracts the solvent or solvents from the film of coated polymer solution, resulting in a precipitation of the polymer in the form of a structured membrane on the device. In the wet process several baths can be used, the polymer being precipitated in the first bath followed by other baths to facilitate drying of the membrane.

The wet process can also use a pore-forming substance or substances to enhance the porous nature of the substructure of the membrane. These pore-forming substances are, generally, poor solvents for the polymer and are usually dissolved out in the quench bath at the time the polymer is precipitated.

The dry process also provides an asymmetric membrane and utilizes a solvent system for the polymer and a pore-forming substance, which is a non-solvent for the polymer. As in the wet process the device is coated with a solution of polymer and pore-forming substance; however, in the dry process the solvent is allowed to evaporate completely. The successful formation of an asymmetric membrane using the dry process requires that the solvent or solvents evaporate more rapidly than the pore-forming substance. In addition, the pore-forming substance must not be a solvent for the polymer.

As mentioned above, pore-forming substances are employed to control the porosity of the substructure of the asymmetric membrane. The porous channels in the substructure of the polymer can extend through the dense skin, resulting in macropores or a series of holes on the exterior skin of the device. Thus, by increasing the pore-forming substance it is possible to progress from a device having a porous substructure and an imperforate skin to one having a highly perforate skin (FIGS. 8, 9, 10 and 11—Example 11).

Figure 20:
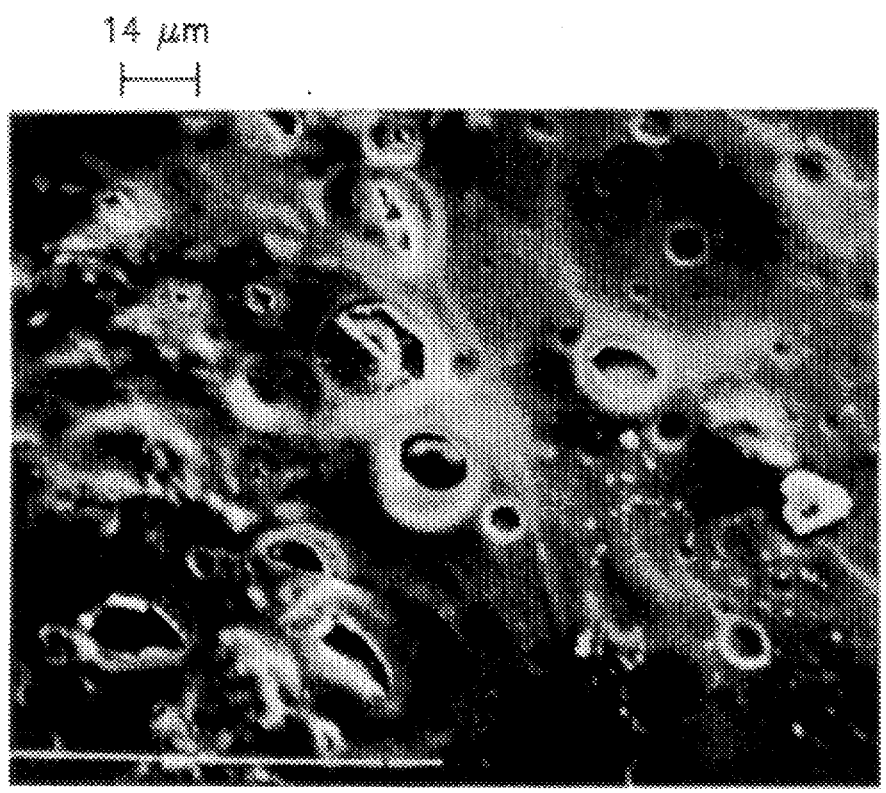
FIG. 20 shows an SEM of the surface, with macro-pores, of a bead surrounded with an asymmetric membrane prepared by a phase inversion dry process as described in Example 23.

Pore-forming substances in the wet process include formamide, acetic acid, glycerol, an alkanol of one to four carbon atoms, 10% aqueous hydrogen peroxide and polyvinylpyrrolidone or combinations thereof. Sodium acetate, or other inorganic salts, can be employed as pore-forming agents as they do not dissolve in the polymer solvents and are dissolved out of the precipitated polymer when the quench is an aqueous quench, leaving macropores in the dense membrane or skin. Suitable pore-forming substances for the dry process include glycerol, water, alkanols, oils, surfactants, glycols or combinations thereof. Rapid drops in pressure during the precipitation of the polymer can also result in enhanced macropore formation when the dry process is employed. For example, spray drying beads coated with a polymer solution under pressure into a chamber at a lower pressure can result in macro-pore formation (FIG. 20—Example 23). When the device of this invention is intended for human or veterinary use, the pore-forming agent should be pharmaceutically acceptable. It should be noted that in the case of some polymer coating materials little or no pore-forming substances may be required to give the desired asymmetric membrane.

Asymmetric-membrane coatings with macropores through the outer skin (perforate membrane coatings) can also be made by adjusting the quench-bath conditions. Raising the temperature of the quench bath to temperatures near the boiling point of the solvent used in the polymer coating solution causes rapid evaporation of the solvent and macropore formation upon precipitation of the polymer in the quench bath. Other nonsolvents, such as ethanol, can be added to the quench bath to cause macropores to form in the membrane coatings. Thus, either perforate or imperforate membranes can be formed depending on the quench-bath temperature and composition.

Figure 24:
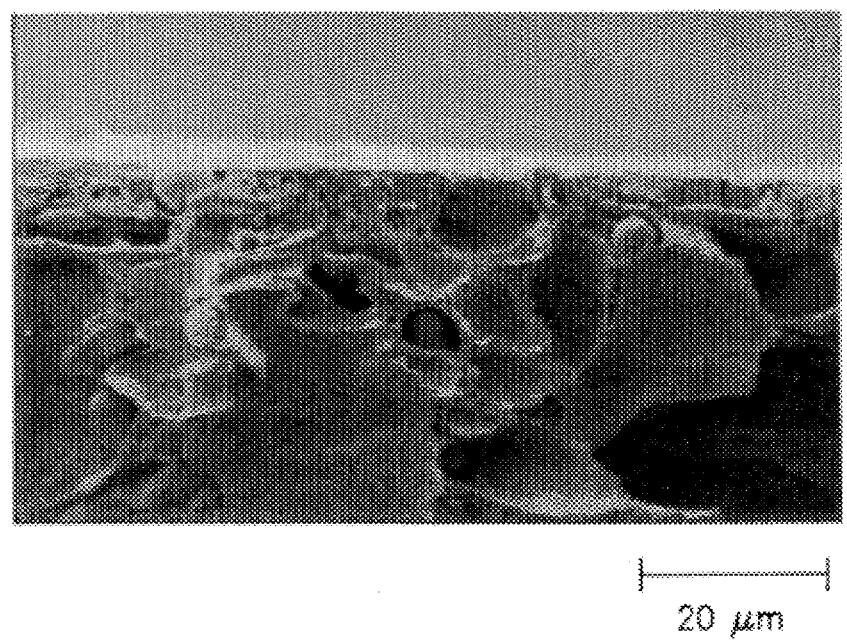
FIG. 24 shows the SEM of a cross section of a capsule wall made of a blend ethylcellulose and cellulose acetate asymmetric membrane (Example 29).

Asymmetric-membrane coatings that have macropores through the outer skin can also be made by making membrane coatings using two or more incompatible polymers. The quantity of macropores through the surface can be controlled by the relative concentrations of the incompatible polymers. Thus, the structure of the outer surface of the membrane coatings can be made either perforate or imperforate depending on the polymers used and their concentrations in the coating solution (FIG. 24—Example 29).

Macropores can also develop in situ by the rupturing of the dense skin located directly over a channel in the substructure. Thus, an imperforate membrane becomes perforate during use.

Figure 5:
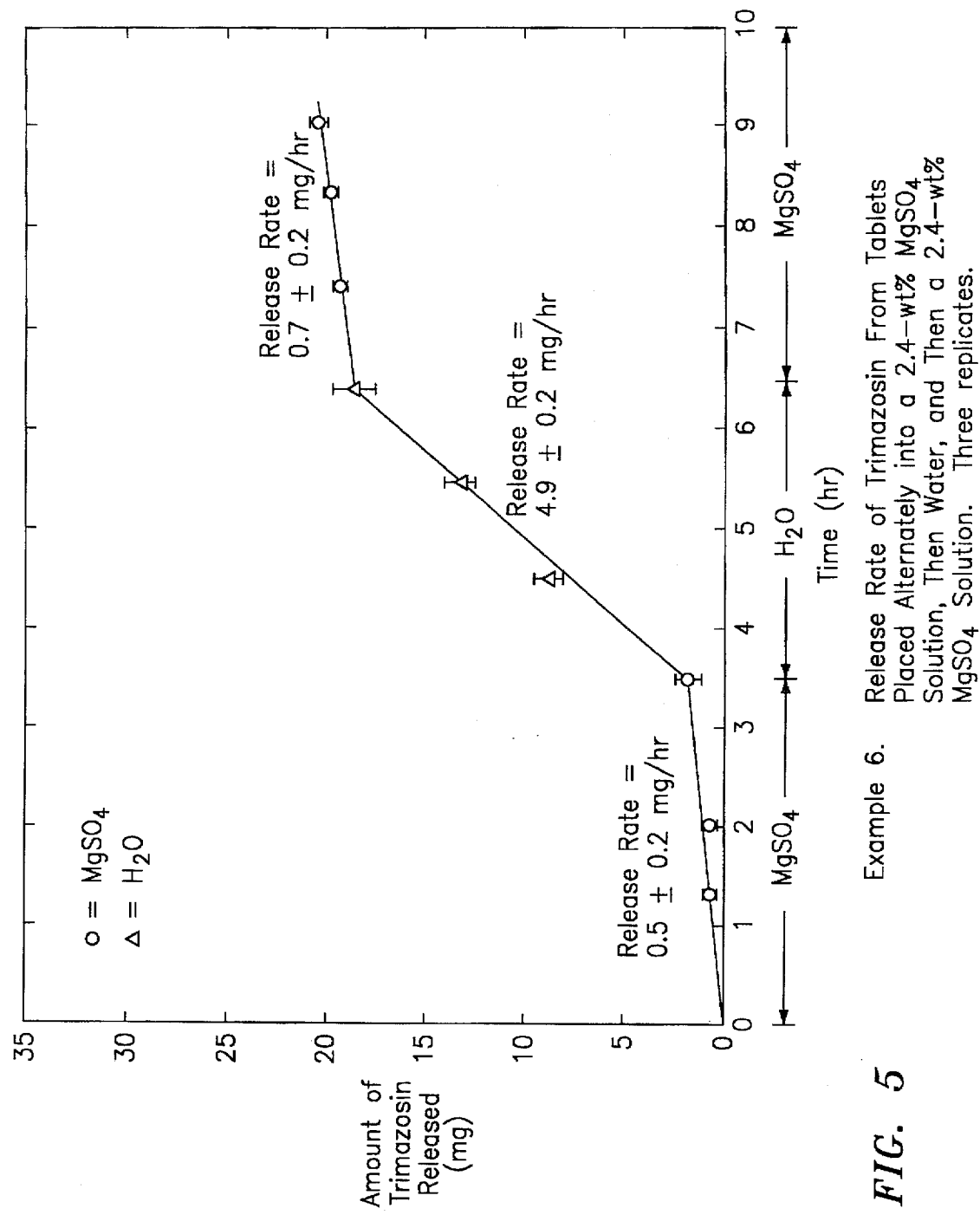
FIG. 5 shows the osmotic release rate of the antihypertensive agent, trimazosin, from an asymmetric membrane coated tablet prepared by the procedure of Example 1.

The active substances and excipients are released from the device of the present invention by either diffusion or osmotic pumping or a combination of both (FIG. 5—Example 6). Release by diffusion is a passive phenomenon in which the active substance moves from a region of high concentration (the interior of the device) to a region of lower concentration (the exterior of the device). Release by osmotic pumping makes use of various osmotically effective compounds in the core of the device. These osmotically effective compounds are the driving force of the device and provide a higher osmotic pressure inside the device than that of the exterior environment, which in the case of a medicinal agent being given orally to a human, would be aqueous. Such osmotically effective substances include sugars such as sucrose, lactose, fructose, mannitol and the like; water soluble salts, such as sodium chloride, sodium carbonate, potassium chloride, calcium chloride and sodium sulfate, water soluble acids, alcohols, surfactants and the like. When the device of this invention is intended for human or veterinary use, the osmotic enhancing agents should be pharmaceutically acceptable.

Other excipients present in the devices of this invention include such water soluble binders as polyethylene glycol, gelatin, agar, carboxycellulose, ethylmethylcellulose, polyvinyl alcohol, water soluble starch, polyvinylpyrrolidone and the like; water insoluble binders include cellulose acetate, polyurethane, epoxides and the like. Excipients can include lubricating agents such as magnesium stearate, sodium lauryl sulfate and talc, as well as organic acids and inorganic and organic bases to help solubilize the active substances when released.

The environments of use can vary considerably and include human and animal bodies, soil, plant surfaces, air, aqueous medium and foods and beverages.

Concerning the active substances, these can vary widely in nature; they can be drugs, nutrients, plant growth regulators, fertilizers, biocides, insecticides, pesticides, pheromones, germicides, and such common uses as room deodorizers, pool chlorinators, flavors, fragrances and insect repellents.

When the active substance is a drug, it can be an antihypertensive antianxiety, bronchodilator, hypoglycemic, a cough or cold agent, antihistamine, decongestant, neoplastic, anti-ulcer, antiinflammatory, hypnotic, sedative, tranquilizer, anesthetic, muscle relaxant, anticonvulsant, antidepressant, antibiotic, analgesic, antiviral, etc. Further such drugs can be in the form of a solution, dispersion, paste, cream, particle, granule, emulsion, suspension or powder.

The shape of the devices of the present invention can also vary greatly. They can be in the form of a tablet, capsule or bead which can be used for the adminstration of a medicinal agent to a human, or in the case of a capsule, can be sufficiently large enough to be used as a bolus in administering medicinal agents to ruminants. Further, the tablet can be of sufficient size that it can be used to chlorinate pool water over a sustained period of time, or to deliver large quantities of other active substances.

In summarizing the nature of the membrane of the present devices and the methods for releasing active substances from the core of said device, the membrane can be permeable, meaning that both solvent and active material can pass through the membrane, and imperforate, meaning there are no visible macropores in the dense thin skin. If the skin is sufficiently strong or the osmotic core pressure sufficiently low, the release from this device may be substantially by diffusion (the term "substantially" implies that most, i.e., over 50% of the release is by this release mechanism). If the thin skin forms macropores in situ, the device would continue to release by diffusion. If the core of the device contains osmotically effective compounds or substances, the osmotic pressure could rupture the skin over the channels of the substructure and the release will be substantially by osmotic pumping.

The membrane can also be permeable and perforate. The delivery or release without osmotic substances will be substantially by diffusion unless the active substance itself is osmotically active. With osmotic enhancing substances in the core of the device the release can be substantially osmotic pumping.

The membrane can also be semipermeable, meaning that only the solvent can pass through the membrane, and imperforate. If the pressure within the core of the device is sufficiently high, macropores can develop in situ, as mentioned previously, and the release will be substantially by osmotic pumping.

Figure 18:
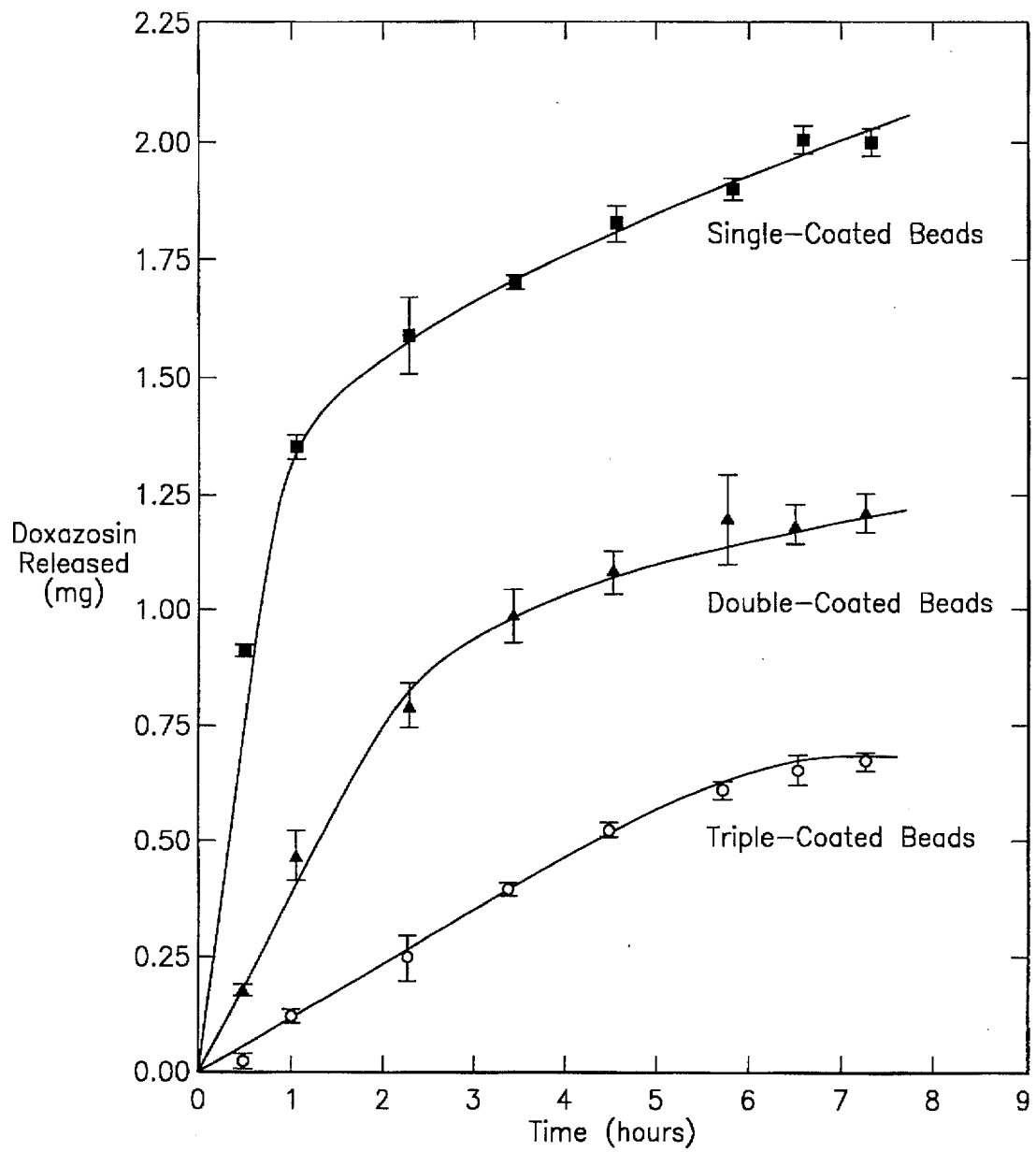
FIG. 18 shows the release rate of doxazosin from asymmetric membrane coated beads having from one to three coats of an asymmetric membrane.
Figure 44:
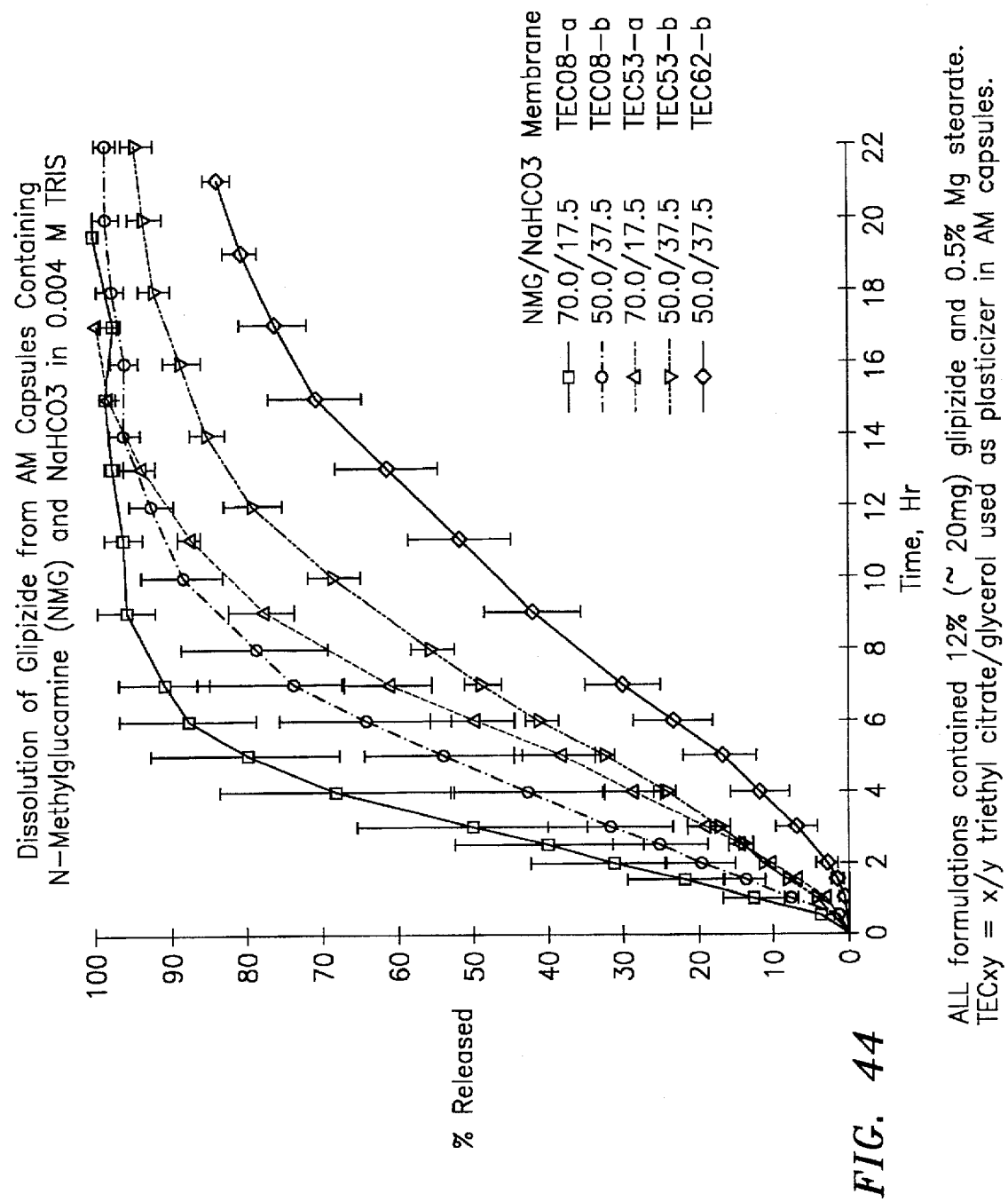
FIG. 44 shows release rate of an active substance from capsules made of an asymmetric membrane using different ratios of plasticizers as in Example 52.

The rate of release of the active substances from the devices of the present invention can be controlled by the release mechanism, the membrane permeability, the nature of the excipients, the size of the device and the size and number of macropores present in the skin of the membrane. In general, release by osmotic pumping releases the active substances faster than diffusion, all other factors being the same. Excipients which aid in solubilizing the active substance enhance release from the device. Also large and numerous macropores aid in rapid diffusional release of the active substances. Another factor which can influence the rate of release is the thickness of the membrane and the number of coats of membrane on the device. In the case of beads the use of multiple coats of membranes will slow the release of active substances (FIG. 18—Example 21). The presence of one or more plasticizers in the material used in making the asymmetric membrane can affect the permeability of said membrane and hence the rate of release of the active substance. In general, hydrophilic plasticizers, such a glycerine, will increase permeability and release rate while hydropholic plasticizers, such as triethylcitrate will reduce permeability and rate of release (FIG. 44—Example 52).

The process for preparing a tablet device surrounded by an asymmetric membrane, wherein the phase inversion is a wet process, consists of dip coating a standard tablet containing the appropriate active substances and desired inert excipients in a solution consisting of about 10–20% by weight of a cellulose derivative or other polymer material and, optionally, 0–35% by weight of one or more pore-forming substances in a solvent consisting of ethyl acetate, methyl ethyl ketone, dimethylformamide, acetone, dioxane or combinations thereof. The pore-forming substances, if used, should meet the criteria previously discussed. The coated tablet is then immersed in an aqueous quench bath, removed and the tablet dried. Alternately, the tablet, after being removed from the aqueous quench bath can be freed of water by using a subsequent immersion in a water soluble, polymer-nonsolubilizing solvent such as isopropanol. The tablet can be dried at this point or it can be put in a bath of an even more volatile solvent than isopropanol, such as hexane, pentane or cyclohexane. These baths employed subsequent to the water bath must be polymer nonsolubilizing. The purpose of baths subsequent to the aqueous quench is to facilitate drying while retaining the membrane structure.

The process for the preparation of a tablet device surrounded by an asymmetric membrane, wherein the phase inversion is a dry process comprises dip coating the said standard tablet with a solution consisting of 10–20% by weight of the cellulose derivative or other polymer material and 20–40% by weight of one or more pore-forming substances in a solvent selected from acetone, methylene chloride or dioxane. The coated tablet is then removed and dried.

As indicated previously, beads can have multiple coats of asymmetric membranes. This requires a repeat of one of the processes mentioned above.

The preparation of capsule shells made of an asymmetric membrane consists of dipping a capsule form into a solution of 10–20% by weight of a cellulose derivative or other polymer material and, optionally, 0–40% by weight of one or more pore-forming substances in a solvent such as acetone or dioxane. The coated capsule forms can be immersed in an aqueous quench bath (phase inversion-wet process) and dried, or they can be air dried without immersing in an aqueous quench bath. Alternately, as with the tablets the coated capsule forms can go through a series of baths as previously described.

The dried capsules are removed from the forms, filled with the desired core material and a capsule top put on the filled bottom section and sealed by some appropriate method, such as applying overlapping tape around the joint of the capsule top and bottom.

As previously indicated, capsules having either the top or bottom made of an asymmetric membrane and the remaining part of an impermeable or semipermeable material is also contemplated by this invention.

The preparation of beads or multiparticulates surrounded by an asymmetric membrane can be carried out using a phase inversion dry or wet process. Using the dry process, a slurry of active substances and inert excipients in the form of beads in a solution consisting of 10–20% by weight of a cellulose derivative or other polymer material and 20–40% by weight of a pore-forming substance in acetone, dioxane or methylene chloride is spray dried into a room or chamber maintained at about 25°–90° C. The separation of the dry coated beads from polymer flakes can be achieved by sieving or by the use of conventional cyclones.

The spray drying can be carried out by a conventional spinning disc or by spraying a slurry of coated beads from a conventional nozzle into a room or chamber. The formation of macropores in the asymmetric membrane coated beads is enhanced by the nozzle spray drying at a pressure 10–100 psi greater than the pressure in the chamber or room.

Beads coated with an asymmetric membrane can also be prepared by the phase inversion wet process which comprises immersing beads coated with a solution of 10–20% by weight of a cellulose derivative or other polymer material and, optionally, 0–40% by weight of one or more pore-forming substances in acetone or dioxane into an aqueous quench bath followed by removal of the beads and drying.

The coated beads of the present invention can be further packaged as a delivery system. For example, the asymmetric membrane coated beads can be placed in conventional gelatin capsules or in a capsule composed of an asymmetric membrane if used in human or veterinary medicine.

Figure 43:
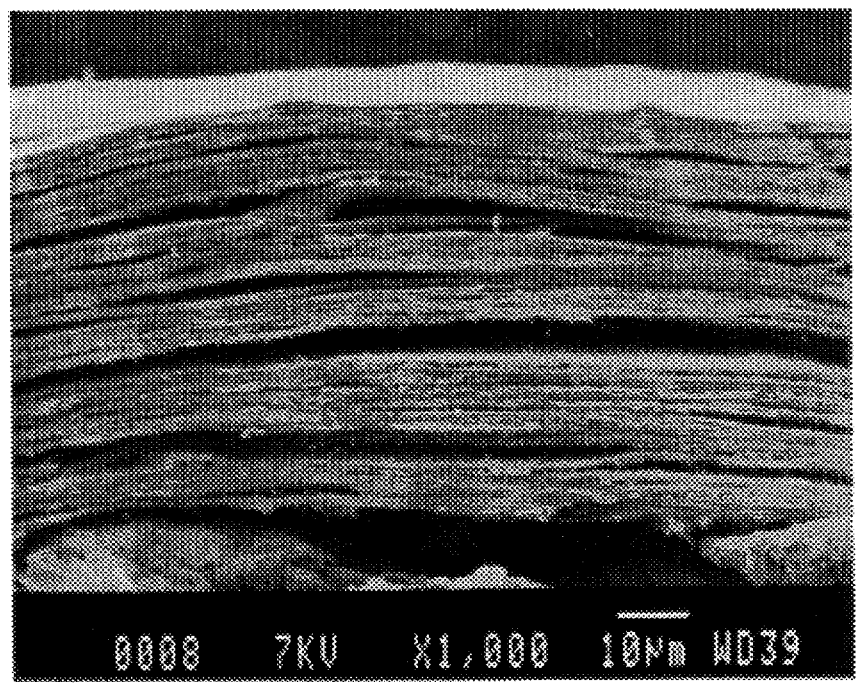
FIG. 43 shows the SEM of the cross section of multiple layers of asymmetric membranes made of cellulose acetate on beads according to Example 49.

It has also been found that the devices of the present invention can be made with multiple asymmetric membranes (FIG. 43—Example 49) by the dry process, which comprises coating beads, capsules or tablets in a Wurster-type fluidized bed coating system. The devices to be coated can be beads, tablets or filled capsules prepared with the appropriate active substances as previously defined. In the case of capsules, the shell thereof can be made of an asymmetric membrane or a conventional shell, such as a gelatin shell. The devices to be coated are circulated in the fluidizer bed coating system mentioned above until the desired number of multiple coats of asymmetric membrane have been applied. Air flow velocity, air temperature and nozzle velocity of the coating spray are obvious parameters which can control the length of time necessary to apply the desired number of asymmetric membrane coats.

In addition to using a fluidized bed coating system to making beads, capsules and tablets having multiple asymmetric membranes, a conventional spray coating technique using a rotating pan coater can also be used.

The following examples illustrate the invention but are not to be construed as limiting the same.

EXAMPLE 1

Formation of Asymmetric Membrane Tablet Coating-Wet Process

A coating solution was made of 15 wt % cellulose acetate 398-10 (Eastman Chemical Products, Inc.) and 14 wt % formamide, dissolved in acetone, and the solution stored in a sealed container at room temperature until used.

Trimazosin tablets made by standard direct-compression techniques and consisting of 40 wt % trimazosin, 58 wt % Avicel PH102 (FMC Corp.), and 2 wt % magnesium stearate (total weight of 280 mg) were dip-coated by immersing them in the coating solution and withdrawing them slowly (about three seconds to completely withdraw a tablet). The tablets were then air-dried at room temperature for five seconds and then immersed in a water quench bath for three minutes. Immediately after the tablets were withdrawn from the water quench bath, they were immersed into an isopropyl alcohol solvent-exchange bath for 3 minutes and subsequently into a hexane solvent-exchange bath, also for 3 minutes. The tablets were then allowed to completely air-dry for at least 12 hours at room temperature.

The coatings formed in the manner described above were asymmetric in appearance, as shown in FIG. 1. The coating consisted of a porous layer adjacent to the tablet, extending through almost the entire coating thickness; on the outside surface a dense skin was formed that was imperforate prior to use. The overall thickness of the membrane coating was approximately 200 µm, and the thickness of the dense outer skin was less than 1 µm.

EXAMPLE 2

Formation of Asymmetric Membrane Tablet Coating-Wet Process

A coating solution was made of 15 wt % cellulose acetate 398-10 (Eastman Chemical Products, Inc.) and 14 wt % formamide, dissolved in acetone, and the solution stored in a sealed container at room temperature until used.

Trimazosin tablets were dip-coated and quenched in a water bath as described in Example 1. The tablets were then allowed to completely air-dry at room temperature for at least 12 hours.

Figure 2:
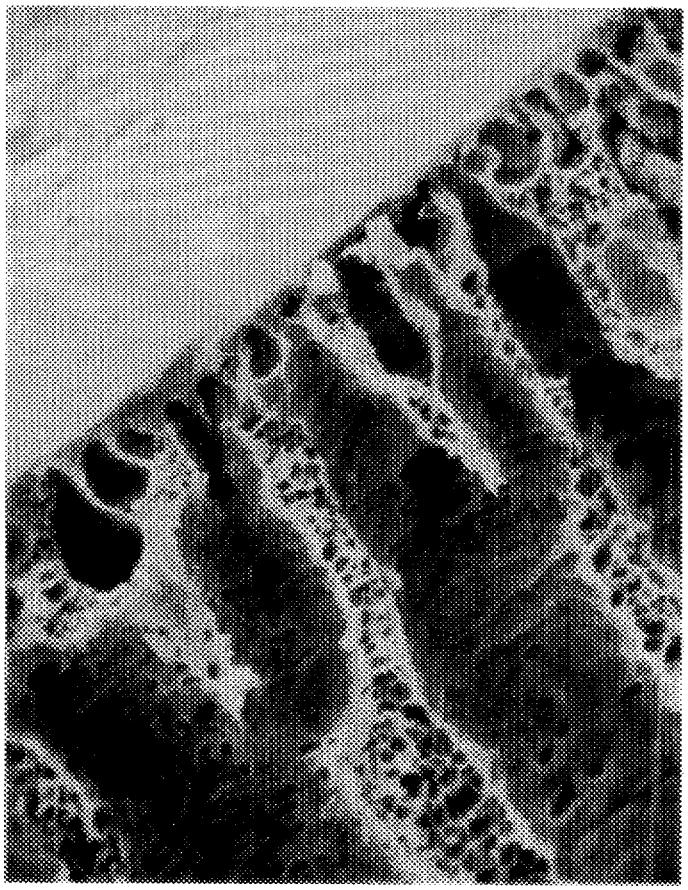
FIG. 2 shows the SEM cross section of an asymmetric membrane tablet coating having an imperforate dense skin. The tablet membrane was prepared according to the procedure of Example 2, utilizing a phase inversion wet process wherein the coated tablet was immersed in an aqueous quench bath.

The coatings formed in the manner described were asymmetric in appearance, as shown in FIG. 2. The coating consisted of a porous layer adjacent to the tablet, extending through almost the entire coating thickness; on the outside surface a dense skin was formed that was imperforate prior to use. The overall thickness of the membrane coatings was approximately 200 µm, and the thickness of the dense outer skin was less than 1 µm.

EXAMPLE 3

Formation of Asymmetric Membrane Tablet Coating-Dry Process

A coating solution was made of 15 wt % cellulose acetate 398-10 (Eastman Chemical Products, Inc.), 1.9 wt % glycerol, 2.7 wt % water, 11.7 wt % butanol, and 21.7 wt % ethanol dissolved in acetone, and the solution stored in a sealed container at room temperature until used.

Figure 3:
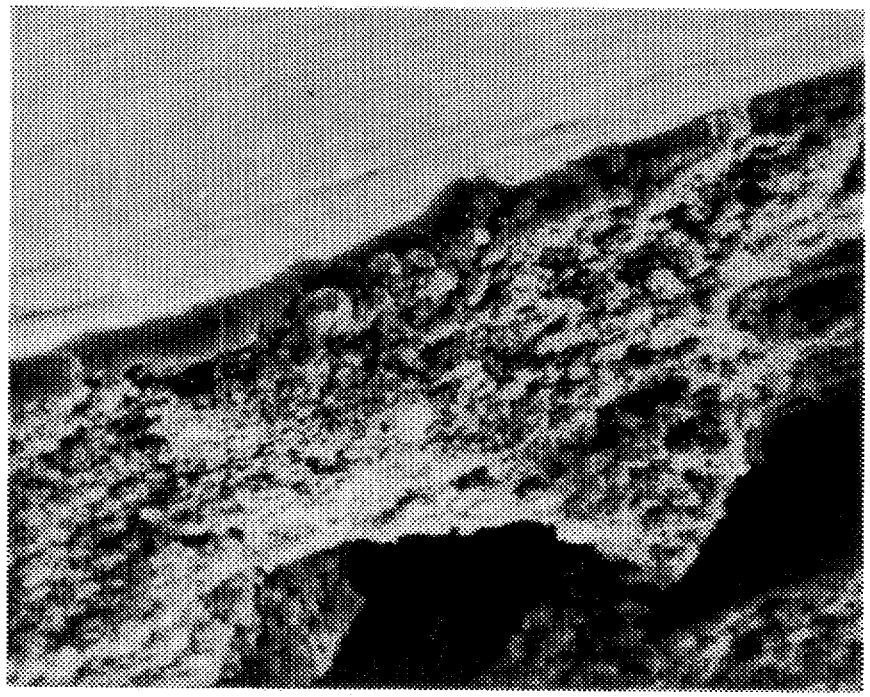
FIG. 3 shows SEM of an imperforate asymmetric membrane coated tablet prepared by the procedure of Example 3, using a phase inversion dry process.

Trimazosin tablets were dip-coated as described in Example 1. The coatings were then dried to completion at room temperature in quiescent air. A cross-section of these coatings is shown in FIG. 3. As described in Examples 1 and 2, the membrane coating consists mostly of a porous sublayer with a thin, dense outer skin. The overall thickness of the membrane was about 125 µm and the thickness of the outer skin was about 1 µm. The outer skin was imperforate prior to use.

EXAMPLE 4

Osmotic Release from Tablets Coated With Asymmetric Membrane Coating and Dense Membrane Coating Individual trimazosin tablets having a weight of 265 mg and containing 64 wt % trimazosin, 21 wt % microcrystalline cellulose, 13 wt % starch, and 5 wt % lubricant were coated with an asymmetric cellulose acetate membrane coating similar to the coating described in Example 1 and with a dense cellulose acetate membrane coating.

The coating solution for the asymmetric membrane was made of 15 wt % cellulose acetate 398-10 (Eastman Chemical Products, Inc.), 27 wt % formamide, dissolved in acetone at room temperature. After dip coating, the tablets were air-dried for 30 seconds before they were immersed in the water quench bath for 3 minutes. As in Example 1, the tablets were then immersed in an isopropyl alcohol solvent-exchange bath for 3 minutes, followed by immersion in a hexane solvent-exchange bath for 3 minutes before being allowed to dry to completion at room temperature. The average weight of these coatings was 13.3±2.5 mg. Based on measurements of coatings made previously in exactly the same manner, the overall thickness of the coating on these tablets was assumed to be approximately 250 µm. A 340-µm diameter hole was mechanically drilled through the asymmetric membrane coating to function as a drug-delivery port.

The coating solution for the dense-membrane coatings was made of 15 wt % cellulose acetate 398-10 dissolved in acetone at room temperature. The tablets were dip-coated, then allowed to air dry before they were dip-coated a second time to increase the coating thickness. The average weight of these coatings was 25.0±2.2 mg—almost twice the coating weight of the asymmetric-membrane coatings. The thickness of these dense coatings, approximately 100 µm (less than half the thickness of the asymmetric-membrane coating), was calculated from the average coating weight, measured surface area, and the reported density for cellulose acetate 398-10. The dense-membrane coatings had about twice as much cellulose acetate in the coatings and were much thinner than are the asymmetric-membrane coatings. Because the dense membranes were relatively thin, more coating material was required to form a durable coating. A 340-µm diameter hole was mechanically drilled through the dense coating to function as a drug-delivery port.

Figure 4:
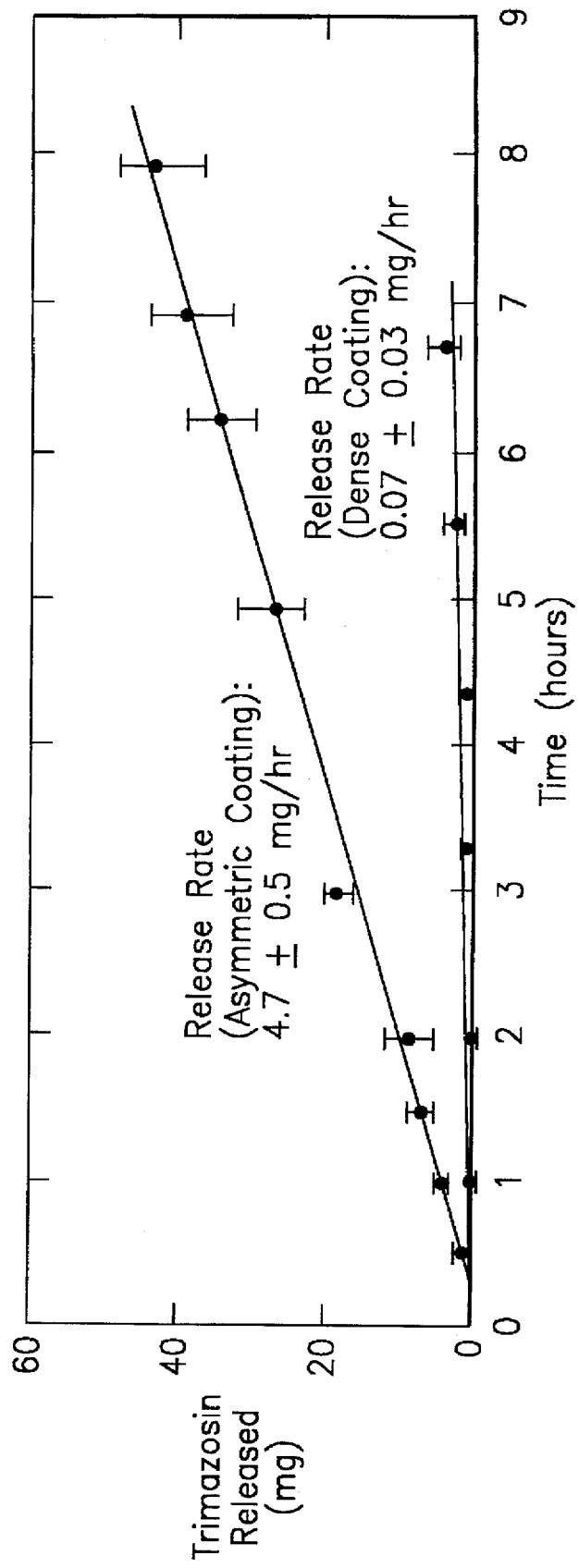
FIG. 4 shows the release rate of the antihypertensive agent, trimazosin, from an asymmetric-membrane-coated tablet, as prepared in Example 1, and a similar tablet coated with a dense membrane with a hole drilled through the membrane.

Release-rate tests were conducted by placing the tablets with the asymmetric- and dense-membrane coatings in water at 37° C. The release profiles for both types of coated tablets are shown in FIG. 4. Both types of coated tablets exhibit steady-state constant release rates, as expected from osmotic delivery systems. The steady-state release rate from the tablets coated with the asymmetric-membrane coatings were about 65 times higher than those from the same tablets coated with dense membranes. This demonstrates higher water permeability through asymmetric membrane coatings and subsequently higher release rates compared with dense coatings made of the same material. The higher release rates possible with the asymmetric coatings are advantageous when higher drug release rates are desired.

EXAMPLE 5

Osmotic Tablets with Asymmetric Membrane Coating—With and Without Hole Drilled Through Coating Trimazosin tablets containing 40 wt % trimazosin, 58 wt % Avicel PH102 (FMC Corp.), and 2 wt % magnesium stearate, with a total weight of 350 mg, were coated with asymmetric cellulose acetate membrane coatings in the same manner as described in Example 1. A 340-µm diameter hole was mechanically drilled through the coating on some of these tablets. The outer skin of the coatings was continuous except for the drilled holes.

These tablets were release-rate tested in water at 37° C. The release-rate results were essentially the same for tablets with and without a hole drilled through the coatings. The average release rate from the tablets with a hole drilled through the coatings was 4.4±0.1 mg/hr compared with 4.7±0.4 mg from the tablets without a hole drilled through the asymmetric-membrane coatings. The time lag before drug delivery began was less than an hour for all the tablets. Tablets with a hole drilled through the coating had a time lag about half that observed for the tablets without a hole drilled through the coating. These results indicate that drug was pumped out pores in the asymmetric membrane coating and that drug-delivery ports do not need to be incorporated into asymmetric coatings in a separate processing step, as is required in commercially available osmotic tablets that utilize dense coatings.

EXAMPLE 6

Osmotic Release From Tablets Coated With Asymmetric Membrane

Tablets containing 40 wt % trimazosin, 58 wt % Avicel PH102, and 2 wt % magnesium stearate (total weight of 350 mg) were coated with an asymmetric cellulose acetate membrane coating as described in Example 1.

Release rates were determined from these coated tablets immersed in a 2.4-wt % magnesium sulfate solution and water. The osmotic pressure of the magnesium sulfate solution was about 6 atm, whereas the osmotic pressure of a saturated solution of trimazosin and the other tablet excipients was about 3 atm. Thus, there was no osmotic driving force for trimazosin delivery from these tablets into the magnesium sulfate solution. The solubility of trimazosin in the magnesium sulfate solution is the same as the trimazosin solubility in water, so any difference in release rates from the tablets placed in magnesium sulfate solution and water cannot be attributed to different concentration gradients across the membrane. Initially the tablets were placed in a stirred solution of 2.4 wt % magnesium sulfate at 37° C. After approximately 3.5 hours the tablets were removed from the magnesium sulfate solution and placed in water (which has an osmotic pressure of 0 atm) for approximately 3 hours and then placed back in fresh 2.4-wt % magnesium sulfate solution. Trimazosin release rates into the two solutions vary by approximately an order of magnitude, as shown in FIG. 1. As expected, the release rate was very low into the magnesium sulfate solution, since trimazosin could only be released into the magnesium sulfate solution by diffusion; the release rate was much higher into water due to osmotic pumping of the trimazosin from the tablet. As soon as the osmotic driving force was removed (placing the tablets back in a magnesium sulfate solution) the release rate dropped, convincingly demonstrating osmotic release from these coated tablets. If the release rates had been controlled by diffusion, then the release rates into water and the magnesium sulfate solution would have been the same.

EXAMPLE 7

Osmotic Release From Tablets Coated With Asymmetric Membrane

Doxazosin tablets containing 0.5 wt % doxazosin, 10 wt % adipic acid, 10 wt % PEG 3350, and 79.5 wt % lactose (total weight of 500 mg) were coated with asymetric-membrane coatings and released into stirred and "unstirred" gastric buffer, and "unstirred" intestinal buffer (both "unstirred" solutions were stirred for 20 seconds each hour before the sample was taken).

The asymmetric coatings were applied in a manner similar to that described in Example 2. The coating solution consisted of 15 wt % cellulose acetate 398-10 (Eastman Chemical Products, Inc.) and 33 wt % ethanol dissolved in acetone at room temperature. The tablets were dip-coated, air-dried for five seconds, then immersed in a water quench bath for four minutes and finally allowed to dry to completion at room temperature. All solutions and the entire coating process were conducted at room temperature.

Release-rate tests were conducted in gastric and intestinal buffers at 37° C. One release-rate test was conducted with stirred (about 150 rpms) gastric buffer and two other release rate tests were conducted in mostly unstirred gastric and intestinal buffers. The "unstirred" solutions were not stirred during the release-rate test except for 20 seconds each hour prior to sampling. The gastric buffer contained sodium chloride, hydrochloric acid, and sodium hydroxide, and had a pH of 1.5 and an osmotic pressure of 7 atm. The intestinal buffer contained potassium phosphate, mono-basic, and sodium hydroxide, and had a pH of 7.5 and an osmotic pressure of 7 atm. Doxazosin solubility in the gastric buffer was about 250 ppm and in the intestinal buffer was less than 10 ppm. The release rate from the tablets placed in stirred (about 150 rpms) gastric buffer is 0.17±0.01 mg/hr. The release rate from the tablets placed in the "unstirred" gastric buffer is 0.17±0.02 mg/hr, and the release rate from the tablets placed in the "unstirred" intestinal buffer was 0.17±0.01 mg/hr. There was virtually no time lag before drug delivery from any of the tablets and all exhibited constant release rates for the duration of the tests (8 hours). Release from osmotic devices is theoretically supposed to be independent of the drug solubility in the receptor solution and of the stirring rate as long as boundary layers outside of the osmotic device do not develop. The same release rates from these doxazosin tablets placed in different receptor solutions demonstrate osmotic delivery using asymmetric-membrane coatings.

EXAMPLE 8

Demonstration of Variations of the Permeability of Asymmetric Membranes on Coated Tablets Trimazosin tablets containing 40 wt % trimazosin, 58 wt % Avicel PH102 (FMC Corp.), and 2 wt % magnesium stearate with a total weight of 350 mg were dip-coated and quenched in a water quench bath, then placed in solvent-exchange baths as described in Example 1. The coating solutions consisted of 15 wt % cellulose acetate 398-10 (Eastman Chemical Products, Inc.) and 7 to 35 wt % formamide, dissolved in acetone. The asymmetric membrane coatings made with these solutions were 150 μm to 250 μm thick. The thickness of the membrane coatings was proportional to the quantity of formamide in the coating solution.

Figure 6:
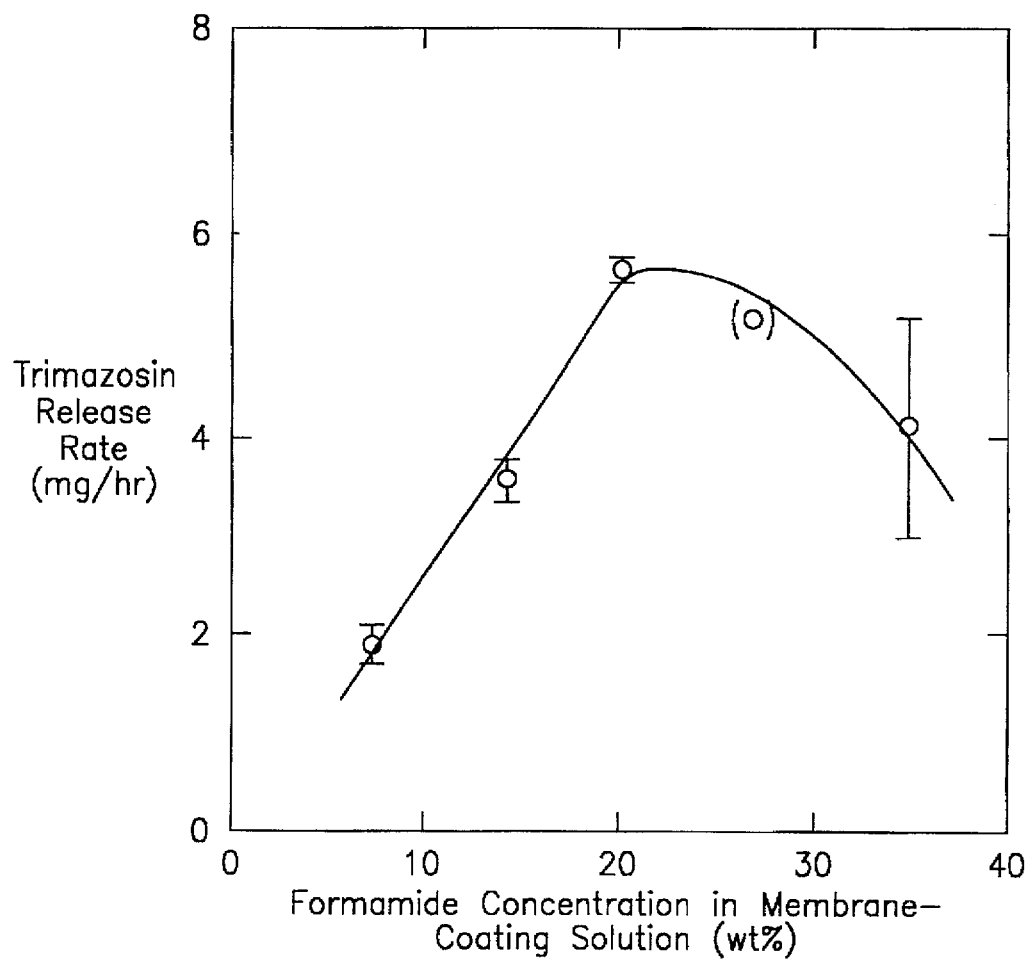
FIG. 6 shows the effect of various levels of the pore-forming substance formamide on the release rate of an asymmetric membrane coated tablet prepared by the procedure of Example 8.

Release-rate tests were conducted, comparing relative permeabilities of the coatings made with coating solutions with different formamide contents. The coated tablets were placed in water at 37° C. Steady-state release rates with respect to the formamide content in the coating solution are shown in FIG. 6. The release rates increase as the formamide content increases up to a maximum at a formamide concentration of about 20 wt %. At higher formamide concentrations the release rates are lower and less consistent from tablet to tablet. The point on the graph corresponding to 27 wt % formamide was actually from 280 mg trimazosin tablets and was normalized with respect to the surface area of the 350 mg tablets. The increasing release rates indicate that the membrane coatings are becoming more permeable to water with increasing amounts of formamide and subsequently higher release rates are achieved. The membrane coatings with formamide concentrations higher than 20 wt % are evidently less permeable than some of the coatings made with coating solutions containing less formamide. This phenomenon has been reported in literature describing reverse-osmosis membranes. The ability to vary the membrane permeability and subsequently the release rate by altering the coating formulation provides added flexibility when designing osmotic delivery systems.

EXAMPLE 9

Enhancement of Osmotic Release Rate from Asymmetric Membrane Coated Tablets

Two types of trimazosin tablets were dip-coated in the same manner as described in Example 1. One type of trimazosin tablet was the same as described in Example 1 except that the total weight was 350 mg rather than 280 mg. The other type of trimazosin tablet contained 40 wt % trimazosin, 40 wt % calcium lactate, 18 wt % Avicel PH102 (FMC Corp.), and 2 wt % magnesium stearate (total weight of 350 mg). The osmotic pressure of a saturated trimazosin solution at 37° C. is about 3 atm, and the osmotic pressure of a saturated trimazosin and lactose solution at 37° C. is about 15 atm. Trimazosin solubility is about 40% lower in a saturated calcium lactate solution than it is in water.

The tablets were placed in water at 37° C. and release rates were determined. The release rates from the trimazosin and the trimazosin/calcium lactate tablets were 4.2±0.05 mg/hr and 7.6±0.42 mg/hr, respectively. As expected, the release rate from the trimazosin/calcium lactate tablets was higher than that from the tablets that contained trimazosin as the only soluble component. Release rates from osmotic delivery systems are theoretically proportional to the difference in osmotic pressures of the solution inside the tablet and the receptor solution. The release rate from the trimazosin/calcium lactate tablets was similar to the theoretical release rate determined from the release rate of the tablets containing only trimazosin, the difference in osmotic pressures between the two tablet materials, the solubility of the trimazosin in water and saturated calcium lactate, and theoretical boundary layers developed in the asymmetric-membrane coatings.

EXAMPLE 10

Control of Osmotic Release Rate from Assymetric Membrane Coated Tablets

Doxazosin tablets made with different soluble fillers were released into gastric buffer (osmotic pressure of 7 atm) to demonstrate that the osmotic release rate can be varied by using fillers with different osmotic pressures. Four different types of doxazosin tablets were made with soluble fillers that have different osmotic pressures in solution.

1) Doxazosin/ascorbic acid tablets were made with 1 wt % doxazosin, 85 wt % ascorbic acid, 13 wt % Avicel PH102 (FMC Corp.), and 1 wt % magnesium stearate. The osmotic pressure of a saturated solution of these tablet excipients was about 54 atm (47 atm osmotic driving force in gastric buffer), and the doxazosin solubility in a saturated solution of the tablet excipients was about 26 mg/ml.

2) Doxazosin/succinic acid/lactose tablets were made with 1 wt % doxazosin, 49.5 wt % succinic acid, and 49.5 wt % lactose. The osmotic pressure of a saturated solution of these tablet excipients was about 47 atm (40 atm osmotic driving force in gastric buffer), and the doxazosin solubility in a saturated solution of the tablet excipients was about 27 mg/ml.

3) Doxazosin/succinic acid tablets were made with 1 wt % doxazosin, 97 wt % succinic acid, and 2 wt % PEG 1000. The osmotic pressure of a saturated solution of these tablet excipients was about 29 atm (22 atm osmotic driving force in gastric buffer), and the doxazosin solubility in a saturated solution of the tablet excipients was about 27 mg/ml.

4) Doxazosin/adipic acid/lactose tablets were made with 1 wt % doxazosin, 10 wt % adipic acid, 79 wt % lactose, and 10 wt % PEG 1000. The osmotic pressure of a saturated solution of these tablet excipients was about 25 atm (18 atm osmotic driving force in gastric buffer), and the doxazosin solubility in a saturated solution of the tablet excipients was about 20 mg/ml. All of the tablets had a total weight of 500 mg and contained 5 mg of doxazosin. All of the tablets were coated with an asymmetric-membrane coating as described in Example 2.

Figure 7:
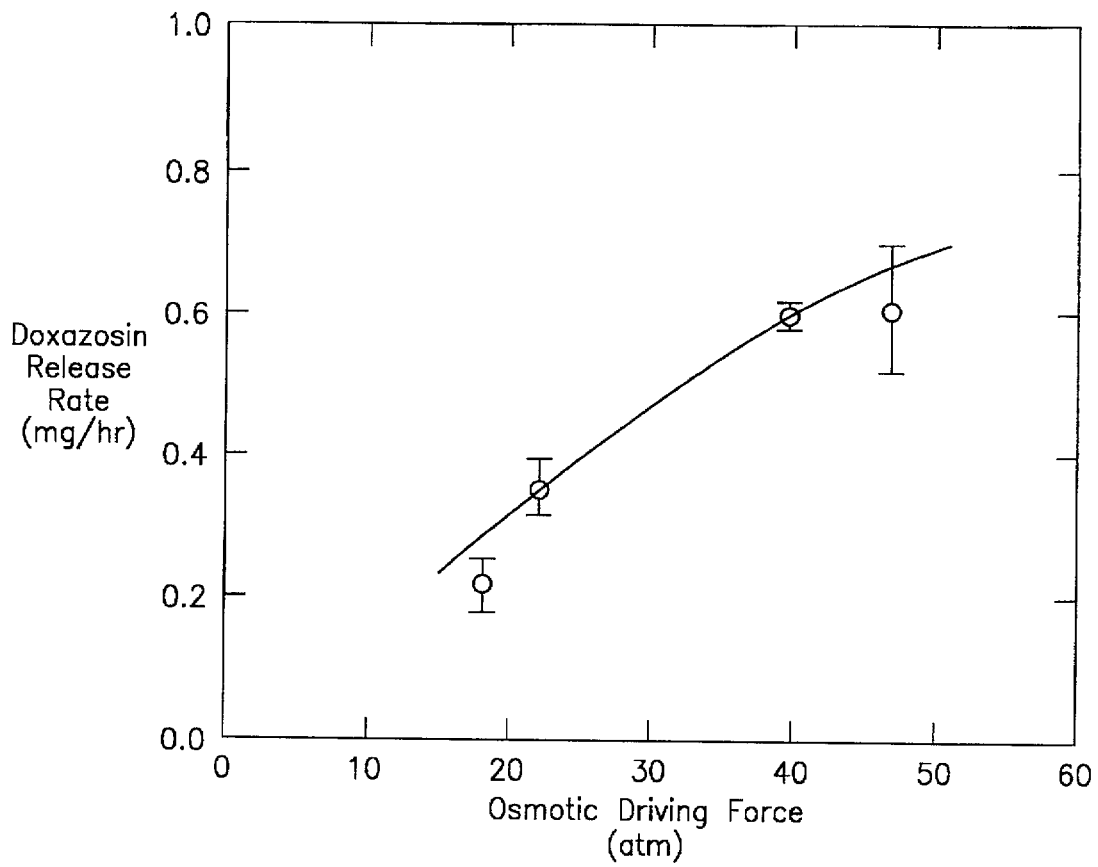
FIG. 7 is a plot showing the change in release rates of the antihypertensive agent doxazosin with changes in the osmotic pressure of the core matrix from an asymmetric membrane coated tablet.
Figure 8:
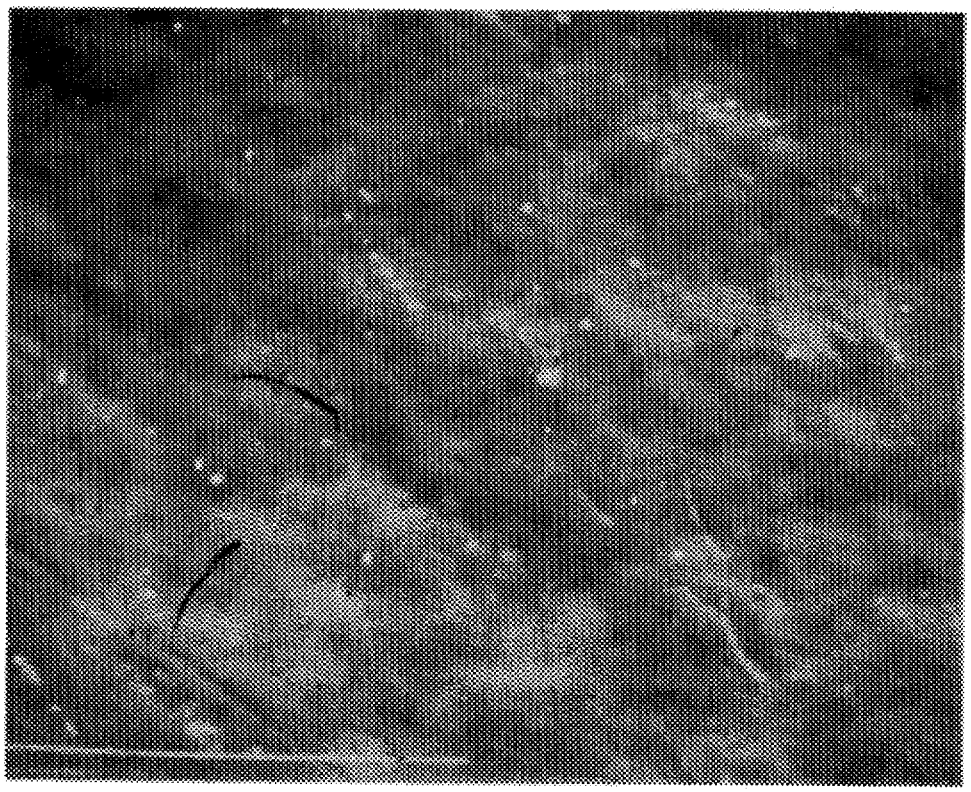
FIGS. 8, 9, 10 and 11 are SEM which show the effects of increasing amounts of the pore-forming substance glycerol on the size of holes or ports in the dense membrane of an asymmetric membrane coated tablet, prepared in Example 11.
Figure 9:
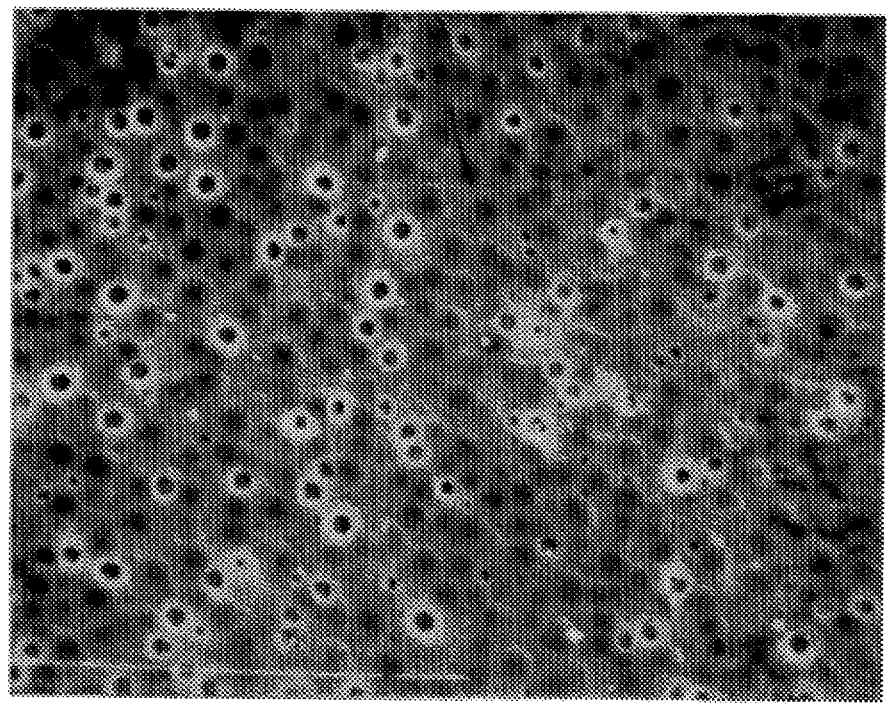
Figure 10:
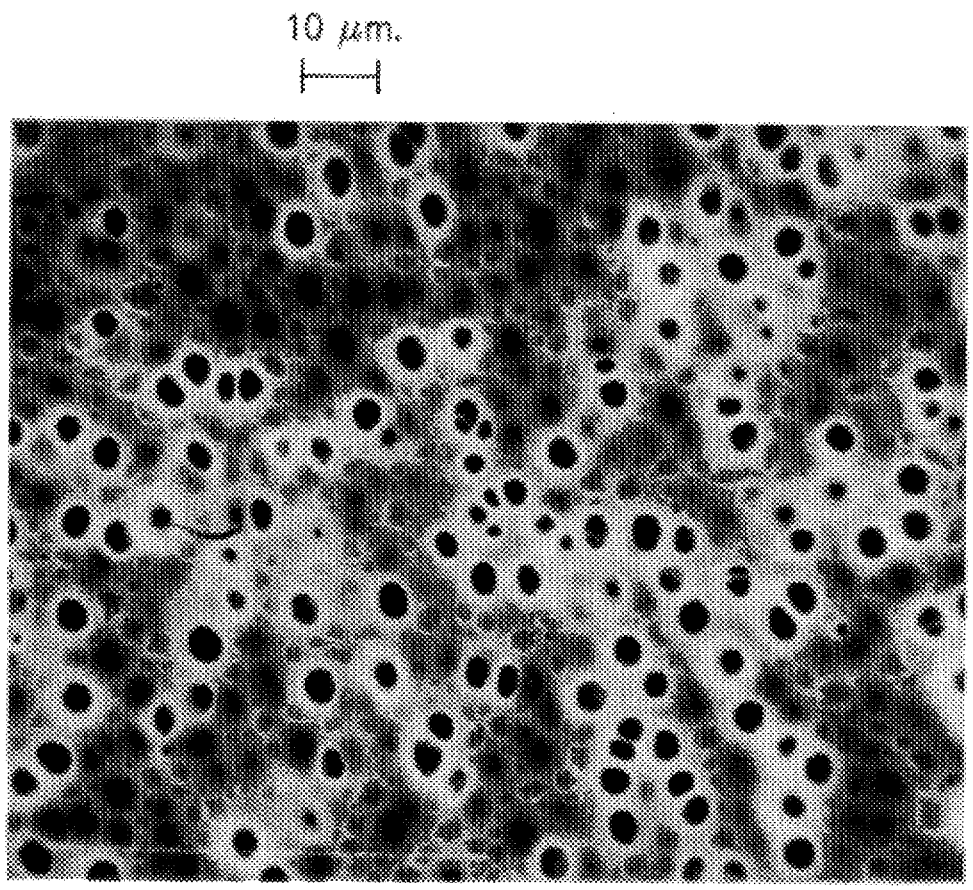
Figure 11:
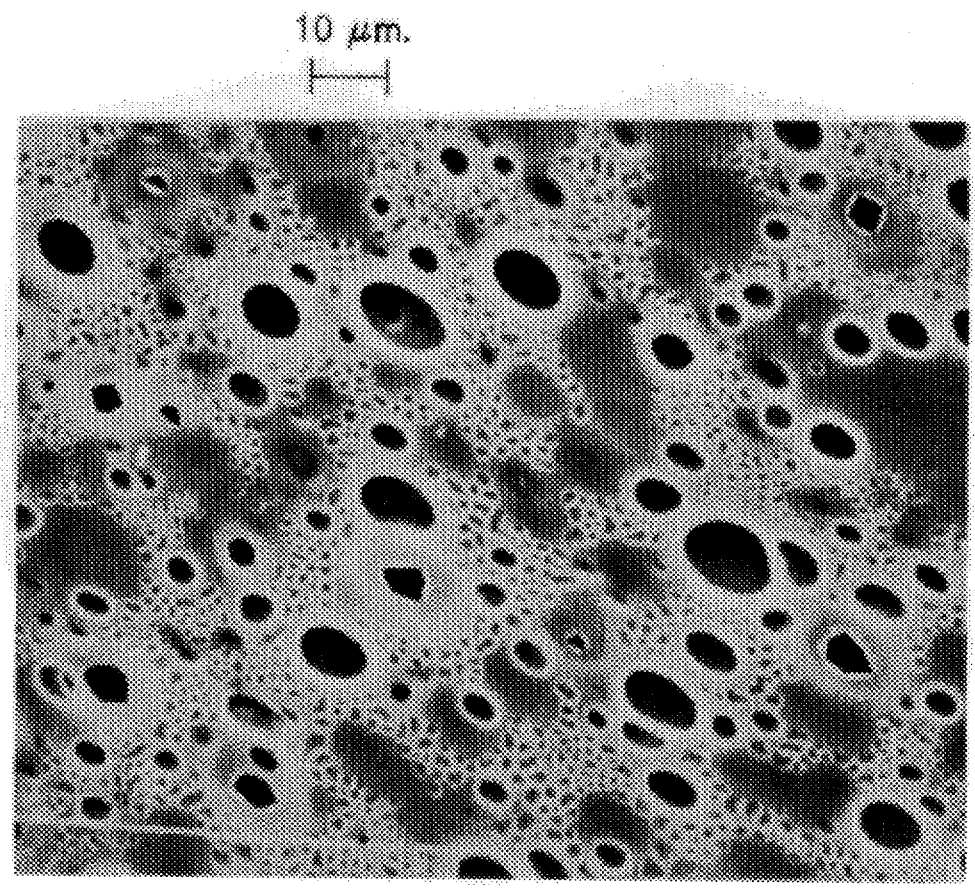

Release rates from these tablets into gastric buffer vary from approximately 0.2 mg/hr to 0.6 mg/hr, as shown in FIG. 7. The release rates increased with an increase in the osmotic driving force as is characteristic of osmotic delivery systems. The release rate from the doxazosin/adipic acid/lactose tablets was lower than theoretically predicted, because the doxazosin solubility was lower than that in the other tablets. Tablets with higher osmotic driving forces will build up larger boundary layers within the asymmetric membrane, and the release rates will not be directly proportional to osmotic driving force. These data illustrate that the doxazosin release rates can be controlled by selecting certain soluble fillers for the tablets.

EXAMPLE 11

Formation of Macropores in Asymmetric Membrane

Trimazosin tablets containing 40 wt % trimazosin, 59 wt % Avicel PH102 (FMC Corp.), and 1 wt % magnesium stearate with a total weight of 500 mg were dip-coated as described in Example 2. The coating solutions contained 1 wt %, 5 wt %, 10 wt %, and 20 wt % glycerol as a pore-former in place of formamide. All of the coating solutions contained 15 wt % cellulose acetate 398-10 (Eastman Chemical Products, Inc.) and were dissolved in acetone.

The coatings made with these coating solutions were asymmetric in structure and similar to the coatings described in Example 2, but instead of having a continuous outer skin, macropores were formed through the skin. More and slightly larger macropores were formed as the glycerol concentration in the coating solution was increased (FIGS. 9–12). Coatings made from coating solutions containing 1 wt % glycerol do not form macropores through the outer skin, but macropores were formed on the outer skin as the concentration of glycerol was increased to 5 wt % glycerol and greater. These macropores, formed during the coating process, presumably serve as drug-delivery ports.

Trimazosin release rates into water and a 2.4 wt % magnesium sulfate solution were determined from tablets coated with solutions containing 1 wt %, 10 wt %, and 20 wt % glycerol. Higher release rates into water than those into the magnesium sulfate solution indicate osmotic release, as was described in Example 6. The release rates into the two receptor solutions are shown in Table I. The coatings made with 1 wt % and 10 wt % glycerol appeared to deliver trimazosin osmotically (higher release rates in water than in the magnesium sulfate solution). The release rates from the tablets coated with the solution containing 20 wt % glycerol were the same into the two receptor solutions, which is characteristic of diffusional release. Thus, by controlling the glycerol concentration in the coating solution, tablet coatings can be made that facilitate osmotic and/or diffusional release of the drug.

TABLE I

| Tablet Coating | Released Into 2.4-wt % MgSO$_4$ | Released Into H$_2$O |
| --- | --- | --- |
| 1) 15 wt % CA/1 wt % glycerol/84 wt % acetone | 2.41 ± 0.43 | 6.30 ± 0.27 |
| 2) 15 wt % CA/10 wt % glycerol/75 wt % acetone | 4.62 ± 0.54 | 7.65 ± 1.05 |
| 3) 15 wt % CA/20 wt % glycerol/65 wt % acetone | 3.03 ± 2.22 | 3.39 ± 0.35 |

EXAMPLE 12

Formation of Macropores in Asymmetric Membrane

Figure 12:
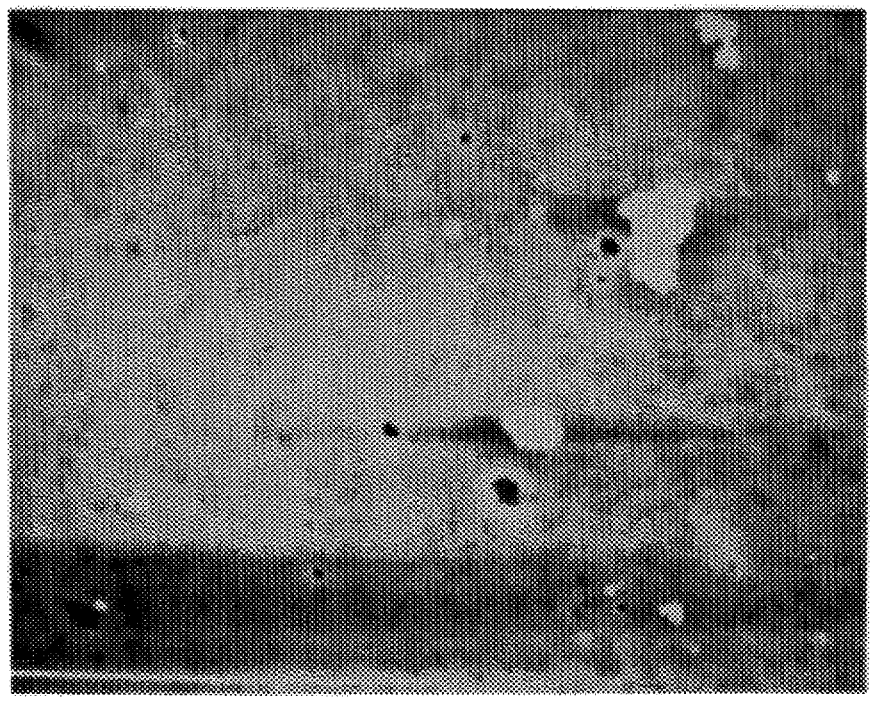
FIG. 12 shows the SEM of dense skin of an asymmetric membrane coated tablet prepared by a wet phase inversion process, as described in Example 12, where sodium acetate was employed as a pore-forming substance.

Trimazosin tablets as described in Example 11 were coated with a coating suspension consisting of 15 wt % cellulose acetate 398-10 (Eastman Chemical Products, Inc.), 5 wt % sodium acetate and 80 wt % acetone. (The sodium acetate did not dissolve in the coating solution, thus this coating solution was a suspension.) The tablets were dip-coated in the stirred coating suspension as described in Example 2. The membrane coatings formed on the tablets were asymmetric and the outer skin had many macropores through the surface. These macropores were about 1 μm to 5 μm in diameter, as can be seen in FIG. 12. These macropores were formed during the coating process and could serve as drug delivery ports for osmotic release.

EXAMPLE 13

Asymmetric Membrane Polymers

Trimazosin tablets containing 40 wt % trimazosin, 58 wt % Ethocel M50 (Dow Chemical Co.), and 2 wt % magnesium stearate with a total weight of 500 mg were coated with asymmetric membranes made of cellulose acetate 398-10 (Eastman Chemical Products, Inc.), Ethocel M50 (Dow Chemical Co.), and cellulose acetate butyrate 171-15 (FMC Corp.). The tablets were dip-coated in the same manner as described in Example 2. The three coating solutions contained 1) 15 wt % cellulose acetate 398-10, and 33 wt % ethanol dissolved in acetone; 2) 12 wt % Ethocel M50, 16 wt % formamide, and 24 wt % methanol dissolved in methyl acetate; and 3) 20 wt % cellulose acetate butyrate 171-15, 9 wt % acetic acid, and 20 wt % formamide dissolved in acetone.

The trimazosin release rates from all three coated tablets were constant, or zero order, for the duration of the tests (7.5 hours), which is typical for osmotic delivery systems. The release rates from tablets coated with asymmetric cellulose acetate, Ethocel M50, and cellulose acetate butyrate coatings were 3.6±0.2 mg/ml, 0.47±0.11 mg/ml, and 0.22±0.11 mg/ml, respectively. Thus, asymmetric-membrane coatings that have different water permeabilities and correspondingly different drug release rates.

EXAMPLE 14

Release Rates of Asymmetric Membrane Coated Tablets Prepared by Dry and Wet Processes Trimazosin release rates into water at 37° C. from the coated tablets described in Example 3 were compared with those reported in Example 5. The asymmetric cellulose acetate coatings described in Example 3 were formed by the dry process, that is, a water quench bath was not used. By comparison, the tablet coatings described in Example 5 were formed by immersing the coated tablets in a water quench bath. Trimazosin release rates from the tablets coated by the dry process were 1.3±0.0 mg/hr compared with release rates of 4.7±0.4 mg/hr from tablets coated by the quench process. The trimazosin tablets coated by the quench process were larger (350 mg) than those coated by the dry process (280 mg). Normalizing the release rates with respect to tablet surface areas, the release rate from the tablets coated by the dry process was 3.9±0.4 mg/hr. Thus, the release rate from tablets coated by the dry-process membranes was about one third that from tablets coated by the quench process. The dry process coatings are evidently less permeable to water than are those made by the quench process.

EXAMPLE 15

Asymmetric Membrane Capsules

Capsules have been made with asymmetric-membrane walls. A solution of 15 wt % cellulose acetate 398-10 (Eastman Chemical Products, Inc.), and 33 wt % ethanol dissolved in acetone was used to make the capsules. The solution was kept at room temperature.

Mandrels were made of glass tubes (9 mm and 10 mm outside diameter) fired at one end until they were rounded and had a small hole (about 1 mm diameter) in the end. A lactose slurry (2 parts lactose and 1 part water) was coated on the glass rods then dried to completion.

The mandrels were immersed in the coating solution and withdrawn slowly (5 seconds to completely withdraw the mandrels). The coated mandrels were inverted and allowed to dry in room-temperature air for 5 seconds and then were immersed in a water quench bath, also at room temperature. The coated mandrels were removed from the water quench bath after 20 minutes and the capsules were removed from the mandrels by sliding a tightly fitting collar down each mandrel and sliding the capsules off. The capsules were then dried for at least 12 hours in room-temperature air. The dry capsules were trimmed to size with a razor blade.

Figure 13:
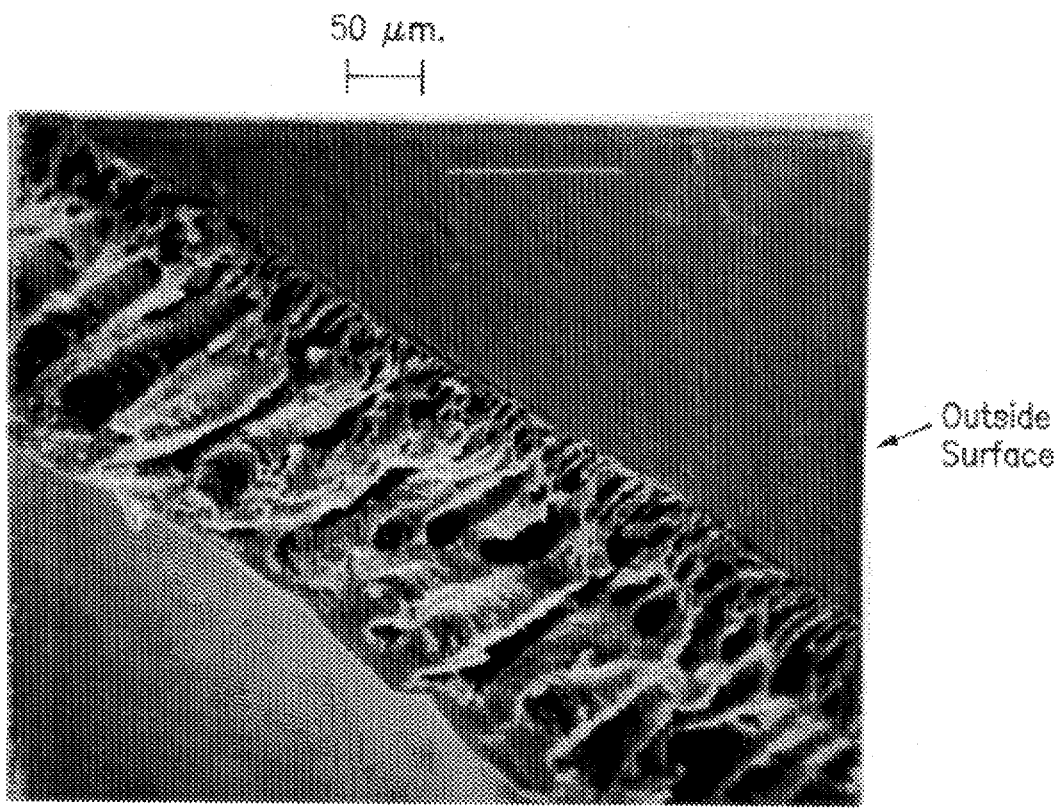
FIG. 13 shows an SEM cross section of capsule wall formed from an asymmetric membrane prepared by the procedure of Example 15.

Capsules formed by the process described above had walls asymmetric in structure with an overall thickness of about 150 μm. The inside surface of the capsules and essentially the entire thickness of the capsule wall were porous. The dense outer skin was about 1 μm thick, as shown in FIG. 13, and was continuous and imperforate.

EXAMPLE 16

Osmotic and Diffusional Release from Asymmetric Membrane Capsules

Asymmetric-membrane capsules were made in the same manner as described in Example 15. The polymer solution used to make these capsules consisted of 17 wt % cellulose acetate 398-10 (Eastman Chemical Products, Inc.), and 30 wt % ethanol dissolved in acetone. The capsules were soaked in a 20-wt % glycerol solution for at least 12 hours after they were removed from the mandrels. The capsules were then allowed to dry at room temperature for at least 12 hours. Soaking the capsules in the glycerol solution plasticized the capsules. Once plasticized, the capsules remained flexible and resilient for at least six weeks.

The capsules were loaded with 250 mg of a powdered-drug mixture. The drug mixture consisted of 1 wt % doxazosin, 10 wt % adipic acid, and 89 wt % lactose. The powder was loaded into the body of the capsule, then a thin band of adhesive solution was placed around the capsule body such that when the cap of the capsule was placed on the body it would cover the adhesive band. Another band of the adhesive solution was then placed around the capsule at the joint between the cap and the body. The adhesive solution was 10 wt % cellulose acetate in ethyl acetate. The adhesive was allowed to dry for at least two hours before the capsules were tested.

The capsules were placed in solutions with different osmotic pressures. The receptor solutions were dextrose solutions of various concentrations and gastric buffer (described in Example 7). The pH of the dextrose solutions was adjusted to a pH of 4 by adding tartaric acid. The doxazosin solubility in all the dextrose solutions was about 10 mg/ml, and the doxazosin solubility in gastric buffer was about 250 ppm. Release rates from osmotic delivery systems are not dependent on the solubility of the receptor solution.

Figure 14:
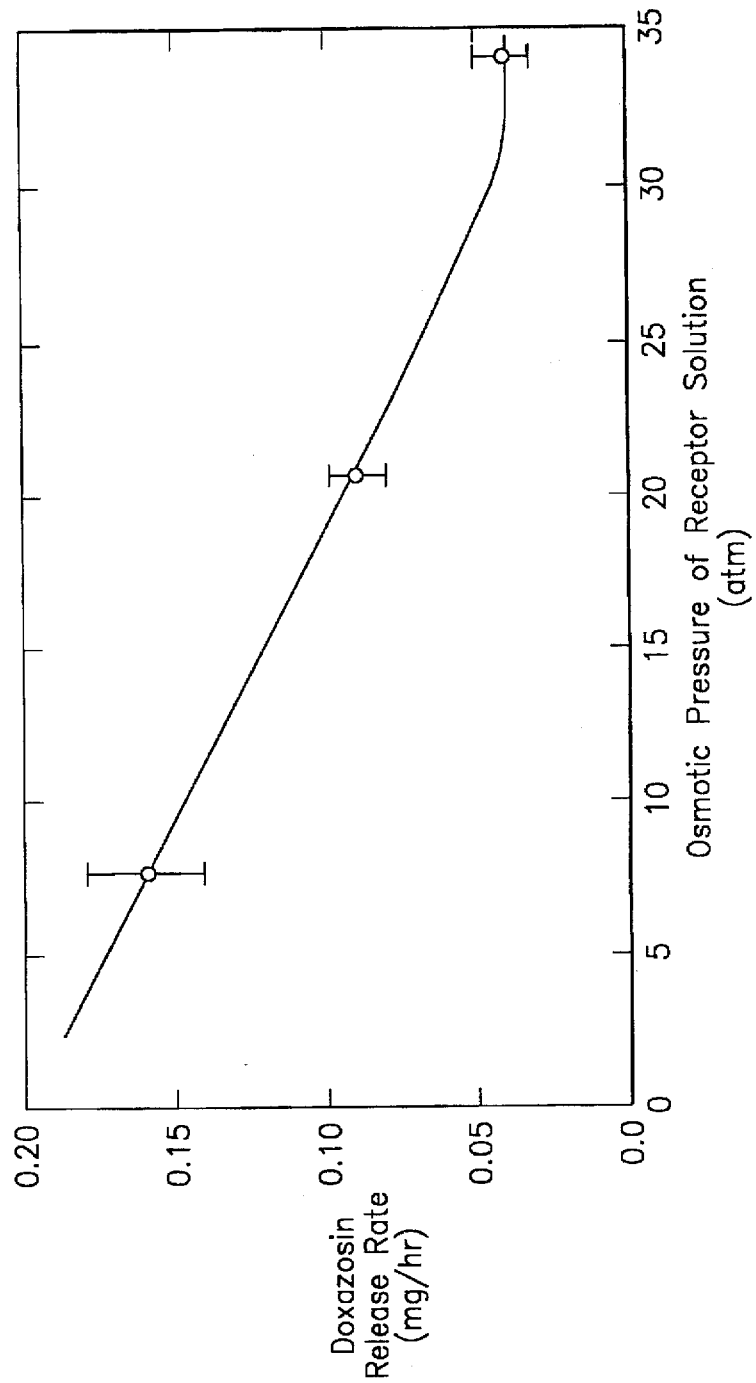
FIG. 14 shows the release rate of doxazosin from capsules, made of an asymmetric membrane, into media at varying osmotic pressures.

The doxazosin release rates from these capsules were higher in solutions having lower osmotic pressure, as shown in FIG. 14. The difference in osmotic pressure between the solution inside the capsule and the receptor solution outside the capsule is the osmotic driving force. Consequently, the osmotic release rates were inversely proportional to the osmotic pressure of the receptor solution. The osmotic pressure inside the capsule was about 25 atm, so the doxazosin released into the 34-atm solution was diffusional rather than osmotic delivery. These data verify that asymmetric capsules can osmotically deliver drugs and that there is a much smaller but significant diffusional contribution to the overall release of doxazosin.

EXAMPLE 17

Control of Time Lag Before Release from Asymmetric Membrane Capsules

Asymmetric-membrane capsules were made as described in Example 15. The only exception to the procedure described in Example 15 was that the mandrels used to make the capsules were hard gelatin capsules in place of glass rods coated with lactose.

The capsules were loaded with three different drug formulations: 1) 300 mg of a 40 wt % trimazosin and 60 wt % calcium lactate powder mixture, 2) 600 mg slurry of 30 wt % trimazosin in PEG 900 (PEG 900 is a liquid at 37° C. and a solid at room temperature), and 3) 260 mg of a 70 wt % trimazosin and 30 wt % tartaric acid powder mixture. Significantly more of the trimazosin/PEG 900 slurry could be loaded in the capsules since it was a liquid suspension rather than a powder. The capsules were sealed with an epoxy adhesive in the same manner as described in Example 16.

These capsules were placed in water at 37° C., and the release of trimazosin was monitored. Time lags before trimazosin delivery began were 7.5 hours, 3 hours, and 0 hours from the capsules loaded with, trimazosin/calcium lactate powder, trimazosin/tartaric acid powder, and trimazosin/PEG 900 slurry, respectively. A saturated solution of trimazosin and calcium lactate has a lower osmotic pressure than a saturated solution of trimazosin and tartaric acid, thus a longer time lag from the capsules loaded with trimazosin and calcium lactate would be expected. The rate of water inbibition into the capsules is theoretically proportional to the osmotic pressure within the capsule. The even shorter time lag from capsules loaded with a trimazosin in PEG 900 slurry was probably due to a combination of the reduction of the interstitial volume between the powder particles, better initial contact with the inside surface of the capsule, and plasticization by the PEG 900, which may facilitate quicker wetting of the membrane and a higher water permeability. The ability to control the time lag before drug delivery begins may be advantageous for designing drug-delivery systems that must be released in the intestines or for other specialized drug-delivery profiles.

EXAMPLE 18

Macropores in Asymmetric Membrane Capsules

Figure 15:
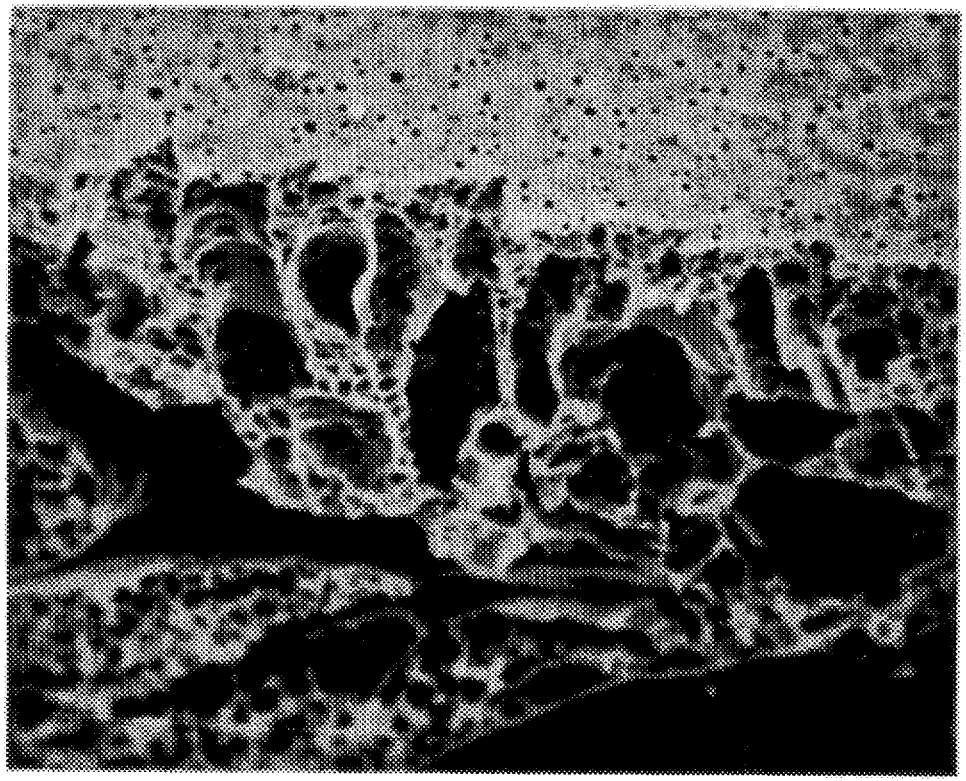
FIG. 15 depicts SEM of the outer surface and cross section of a capsule made of an asymmetric membrane in which glycerol was employed as the pore-forming substance.

Asymmetric-membrane capsules have been made that have macropores through the outer skin of the capsules. These macropores function as drug delivery ports through which the drug solution is pumped from the capsules. The capsules were made by the same method as described in Example 15. Gycerol was added to the polymer solution and the ethanol was removed. The polymer solution consisted of 17 wt % cellulose acetate 398-10 (Eastman Chemical Products, Inc.) and 1 wt % to 20 wt % glycerol dissolved in acetone. The macropores were more numerous and slightly larger as more glycerol was used in the polymer solution and were similar in appearance to the macropores in the tablet coatings described in Example 11. The cross section and surface of a capsule wall made with a 17 wt % cellulose acetate and 3 wt % glycerol solution in acetone is shown in FIG. 15. The macropores through the surface and the interconnecting pathways through the capsule wall are apparent in the SEM.

Capsules with macropores (such as the formulation described above) have been loaded with dextran blue and lactose, then placed in water. Dextran blue delivery from the capsules began within the first hour and was pumped out at a constant rate for several hours. Although the dextran blue cannot actually be seen exiting each macropore, the blue color aggregates around the exterior of the capsule, and a steady stream flows to the bottom of the container. In capsules that do not have macropores through the surface, the dextran blue is pumped out discrete delivery ports formed in the asymmetric capsule walls, sometimes with such force that a stream of dextran blue is ejected horizontally for more than a centimeter through the water before it flows to the bottom of the container. Thus, macropores can be formed through the outer skin of asymmetric membrane capsules and appear to function as drug-delivery ports for osmotic drug delivery.

EXAMPLE 19

Asymmetric Membrane Polymers

Asymmetric-membrane capsules have been made with cellulose acetate 398-10 (Eastman Chemical Products, Inc.), Ethocel M50 (Dow Chemical Co.), and cellulose acetate butyrate 171-15 (FMC Corp.). The cellulose acetate capsules were the same as described in Example 15, and the Ethocel and cellulose acetate butyrate capsules were made in the same mannner as described in Example 15. The Ethocel polymer solution consisted of 12 wt % Ethocel M50, 16 wt % formamide, and 24 wt % methanol dissolved in methyl acetate, and the cellulose acetate butyrate polymer solution consisted of 20 wt % cellulose acetate butyrate, 9 wt % acetic acid, and 20 wt % formamide dissolved in acetone. The average wall thicknesses of the Ethocel and the cellulose acetate butyrate capsules were approximately 300 µm and 450 µm, respectively. The thickness of the dense outer skin for both these capsules was about 1 µm. All of the capsules were loaded with a 30 wt % trimazosin in PEG 900 slurry at about 37° C. (PEG 900 is a solid at room temperature.) The capsules were sealed with an epoxy adhesive as described in Example 16.

Trimazosin release rates into water at 37° C. were 7.7±0.2 mg/hr, 2.2±0.4 mg/hr, and 0.65±0.4 mg/hr from the capsules made of cellulose acetate, Ethocel, and cellulose acetate butyrate, respectively. These data illustrate the different water permeabilities in the polymers investigated and how these properties can be utilized to formulate osmotic capsules with different release kinetics.

EXAMPLE 20

Asymmetric Membrane Coated Beads

Asymmetric membrane coatings were applied to nonpareil beads (20- to 25-mesh, or about 1 mm in diameter) with a spray-coating process. The beads were mixed with the polymer coating solution, then sprayed through an external-mixing air-atomizing nozzle (Model 100150) available from Spraying Systems Co., Wheaton, Ill.

The polymer coating solution consisted of 15 wt % cellulose acetate 398-10 (CA, Eastman Chemical Products, Inc.) and a 38-wt % nonsolvent mixture dissolved in acetone. The nonsolvent mixture consisted of 57 wt % ethanol, 31 wt % butanol, 7 wt % water, and 5 wt % glycerol.

Figure 16:
FIG. 16 shows an SEM of the surface and cross section of a bead covered with an asymmetric membrane and made by the procedure described in Example 20.

The beads and polymer solution were mixed just upstream from the spray nozzle, and the mixture of beads and polymer solution was sprayed into a room kept at about 40° C. As the beads were sprayed into the room, the solvent evaporated from the beads and an asymmetric-membrane coating was formed around the beads. Thus, asymmetric-membrane coatings were formed on the beads by a dry process; that is, a quench bath was not required to form the asymmetric-membrane coatings. Excess polymer precipitated in flakes, and the beads were separated from the polymer flakes by sieving. Typically, a 7-wt % coating was applied to the beads. The asymmetric coatings on beads (FIG. 16) were similar in appearance to the dry-process asymmetric-membrane tablet coatings described in Example 3. The asymmetric-membrane coatings on beads were much thinner than the dry-process coatings on tablets. The overall thickness of the coatings on beads was about 10 µm to 20 µm, compared with a thickness of about 200 µm on tablets. Coatings formed on both tablets and beads were porous through essentially the entire thickness and had a dense outer skin that was approximately 1 µm thick.

EXAMPLE 21

Multiple Coatings of Asymmetric Membrane on Beads

Figure 17:
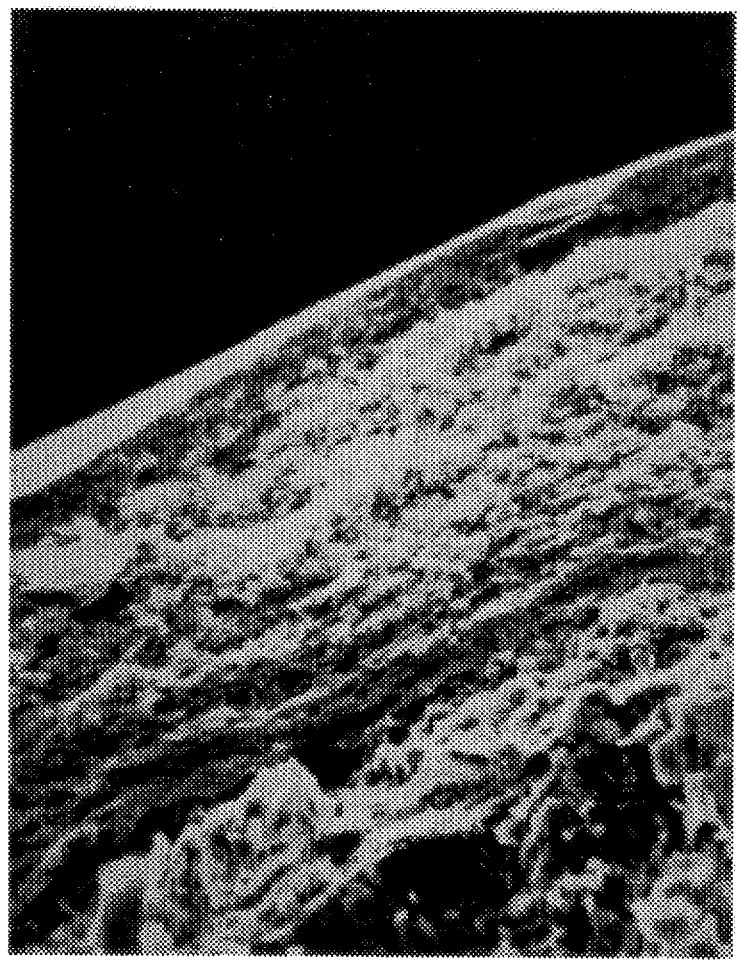
FIG. 17 shows an SEM of the surface and cross section of a bead triple coated with an asymmetric membrane layer, prepared as described in Example 21. Note that only one dense skin is visible.

Doxazosin beads (20- to 25-mesh) containing 5 wt % doxazosin, 15 wt % Avicel PH101 (FMC Corp.), 9 wt % adipic acid, and 71 wt % lactose were prepared. In addition, a 2-wt % precoat of 9 parts sucrose and 1 part hydroxypropylmethylcellulose was also applied to these beads. The beads were coated as described in Example 20 with the polymer solution heated to 34° C. The coating process was repeated three times, and after each coating a quantity of beads were set aside; thus, beads were obtained with single, double, and triple coatings. The overall coating thickness varied from 5 µm to 15 µm for the single-coated beads, from 10 µm to 25 µm for the double-coated beads, and 20 µm to 30 µm for the triple-coated beads, as determined by SEM observation. The outer skin of the coatings was dissolved by the subsequent coatings, leaving a homogeneous porous layer through the entire coating except for an outer skin that was approximately 1 µm thick, as shown by the example in FIG. 17. The outside skin was the same for single, double, and triple coatings.

Release rates were determined from these beads (65 mg) into a lactose solution with an osmotic pressure of 7 atm. The pH of the lactose solution was lowered to 4 with tartaric acid so the doxazosin solubility would be the same as in water (10 mg/ml). Release rates were lower from beads that were coated more times, as shown in FIG. 18. This was probably due to the increase in overall thickness of the asymmetric coating as additional coatings were applied.

EXAMPLE 22

Osmotic Release from Asymmetric Membrane Coated Beads

Figure 19:
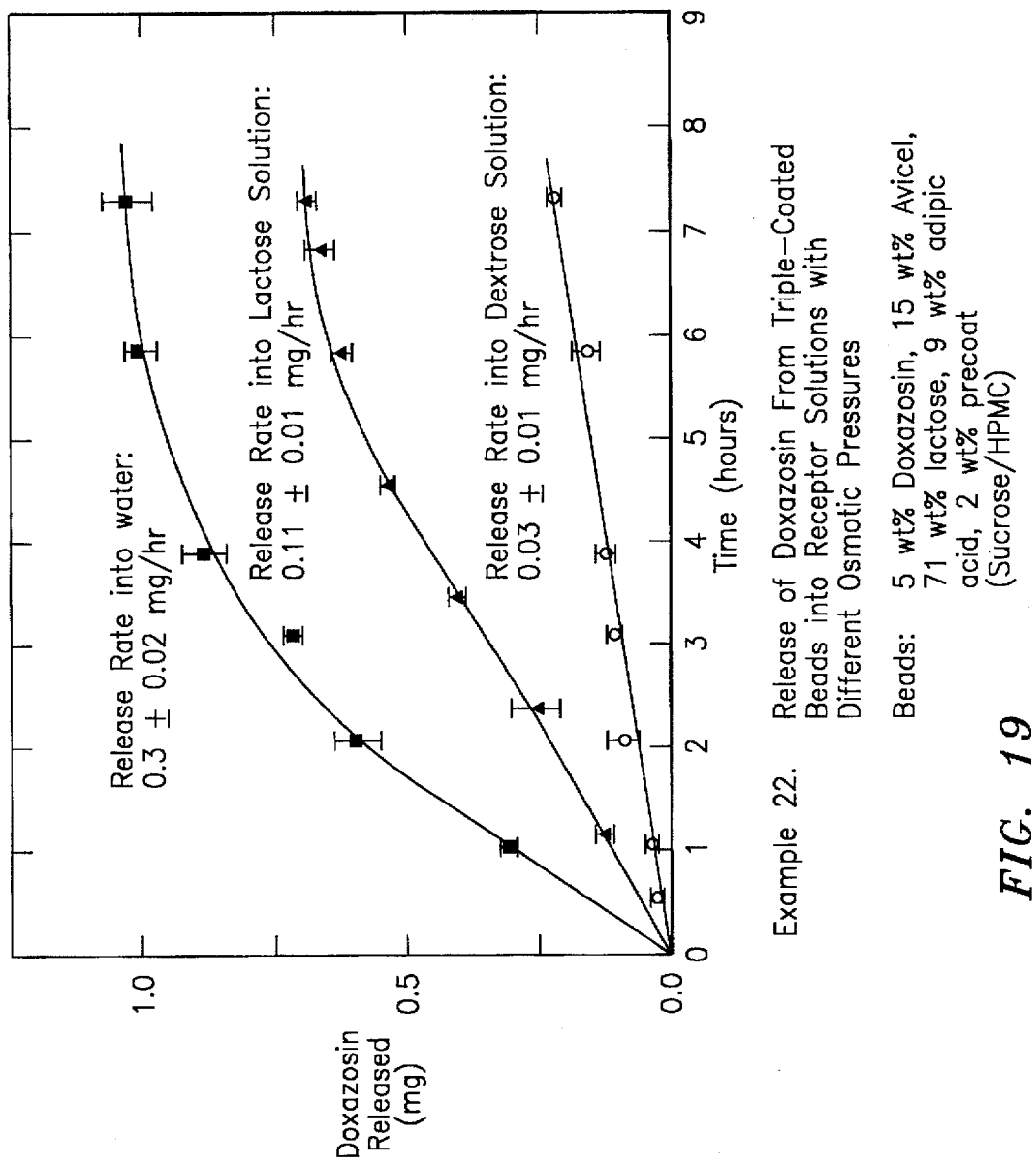
FIG. 19 depicts the release rate of doxazosin from triple asymmetric membrane coated beads into solutions of different osmotic pressures.

Triple-coated doxazosin beads, as described in Example 21, were released into receptor solutions of differing osmotic pressures. The beads were released into water (osmotic pressure of 0 atm), a lactose solution with an osmotic pressure of 7 atm, and a dextrose solution with an osmotic pressure of 20 atm. Tartaric acid was added to the lactose and dextrose solutions to adjust the pH to 4 so that the doxazosin solubility, 10 mg/ml, would be the same in these sugar solutions as it was in water. Thus, any differences in release rates from the beads into the different receptor solutions will not be due to different concentration gradients across the membrane coatings, and the diffusional contribution to the drug release from the beads is the same in all cases. The doxazosin-release rates into these three receptor solutions are shown in FIG. 19. Approximately 0.6 mg of doxazosin was released at different, constant rates from 65 mg of beads placed in each of the receptor solutions. Presumably, the soluble fillers were almost completely released at the point when 0.6 mg of doxazosin had been released, decreasing the osmotic driving force and the doxazosin-release rate. The dependence of the release rates on the osmotic pressure, or more precisely, the difference in osmotic pressure between the solution inside of the beads and the receptor solution is characteristic of osmotic release.

EXAMPLE 23

Formation of Macropores in Assymmetric Membrane Coated Beads

Asymmetric-membrane coatings have been applied to non-pareils by mixing the beads (20- to 25-mesh) in a polymer coating solution at room temperature (same polymer coating solution as that described in Example 20). The beads and coating solution were placed in a pressure vessel, and 40 psi was applied to the vessel. The beads and polymer solution were sprayed out an airless nozzle (a hose connector with a 3-mm diameter oriface) into room-temperature air. The sudden pressure drop as the beads and the coating were sprayed out the nozzle caused bubbles to form in the coating solution, thus forming macropores through the outer skin as the coating precipitates (FIG. 20). The same coating solution (and conditions) but applied without a pressure drop forms a continuous, dense outer skin, as described in Example 3.

EXAMPLE 24

Formation of Asymmetric Membrane Coated Beads-Wet Process

Figure 21:
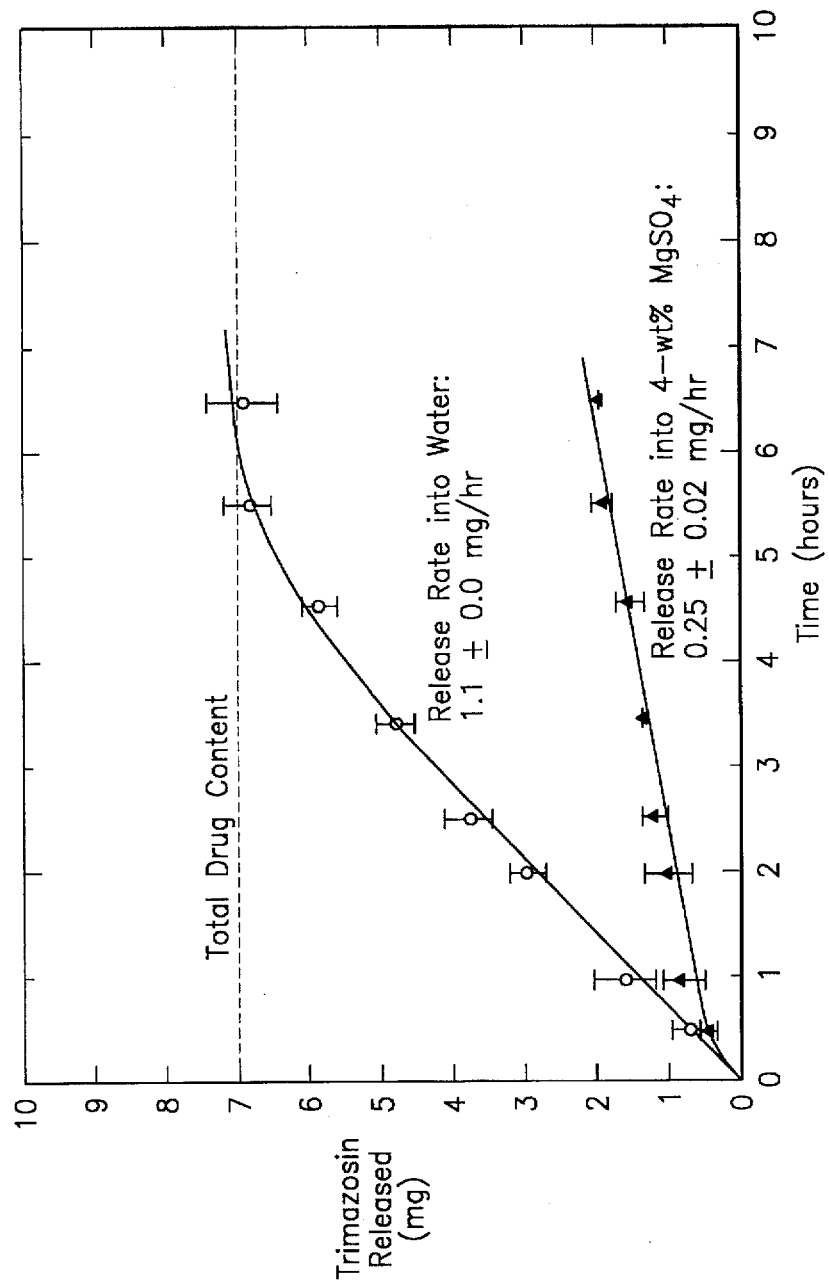
FIG. 21 shows the release of trimazosin from beads covered with an asymmetric membrane into water and into a magnesium sulfate solution. The membrane was prepared according to a phase inversion wet process as described in Example 24.

Trimazosin beads (18- to 20-mesh), containing 30 wt % trimazosin and 70 wt % Avicel PH101 (FMC Corp.) were mixed with a polymer coating solution and dripped into a water quench bath to form asymmetric osmotic beads. The polymer coating solution was made of 15 wt % cellulose acetate 398-10 (Eastman Chemical Products, Inc.), and 33 wt % ethanol dissolved in acetone and was used at room temperature. A mixture of beads and coating solution was dripped into a water quench bath at room temperature from a disposable pipet tip, forming large, spherical asymmetric beads that could contain from none to several smaller trimazosin beads. The beads were kept in the water quench bath for about a minute then removed and allowed to air-dry at room temperature for at least 12 hours. These asymmetric beads had diameters of 2 to 3 mm and a skinned outer surface. Inside the particles was a porous cellulose acetate network. Any trimazosin beads present were dispersed in the porous cellulose acetate network. Osmotic release of trimazosin from these beads was demonstrated by submerging these beads in water and in a 4 wt % magnesium sulfate solution. The results are shown in FIG. 21. The solubility of trimazosin is the same in both solutions; thus, the 75% decrease in release rate into the magnesium sulfate solution was due to reduction of the osmotic driving force across the membrane coating, demonstrating osmotic release.

EXAMPLE 25

Formation of Macropores in Asymmetric Membranes

Doxazosin tablets containing 1.7 wt % doxazosin, 10 wt % adipic acid, 10 wt % PEG 3350, and 78.3 wt % lactose (total weight of 150 mg) were dip-coated with a solution consisting of 15 wt % CA 398-10, 30 wt % ethanol, and 55 wt % acetone. The coated tablets were air-dried for 5 seconds and then immersed in a 60° C. water quench bath for 5 minutes. After the coated tablets were removed from the quench bath, they were air-dried for at least 12 hours at ambient temperature and humidity. These membrane coatings were asymmetric and had macropores in the outer surface of the coating. Small bubbles could be seen forming on the surface of the membrane coating as it precipitated in the quench bath. Several of these bubbles ruptured the skin of the membrane coating forming macropores that could serve as drug-delivery ports.

EXAMPLE 26

Formation of Macropores in Asymmetric Membranes

Doxazosin tablets as described in Example 25 were dip-coated with a solution consisting of 15 wt % CA 398-10, 30 wt % ethanol, and 55 wt % acetone. The coated tablets were air-dried for 5 seconds and then immersed in an ethanol quench bath at ambient temperature for 5 minutes. After the tablets were removed from the quench bath, they were air-dried for at least 12 hours at ambient conditions. The membrane coatings were asymmetric and the outer skin had many macropores through the surface. These macropores were about 1 µm in diameter. The macropores were formed during the coating process and could serve as drug delivery ports.

EXAMPLE 27

Formation of Asymmetric-Membrane Capsules Made With Ethylcellulose

Capsules with asymmetric-membrane walls were made from a coating solution of 15 wt % ethylcellulose (Ethocel std-45, Dow Chemical, Midland, Mich.), 25 wt % acetic acid, and 5 wt % glycerol dissolved in acetone.

Capsules were made using two sizes of mandrels—one size for the capsule cap and one size for the capsule body. The mandrels were immersed in 40° C. coating solution and were withdrawn slowly, taking 7 seconds to completely withdraw the mandrels. The coated mandrels were exposed to room-temperature air for 30 seconds and then immersed in a 45° C. quench bath that contained 5 wt % glycerol in water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 22:
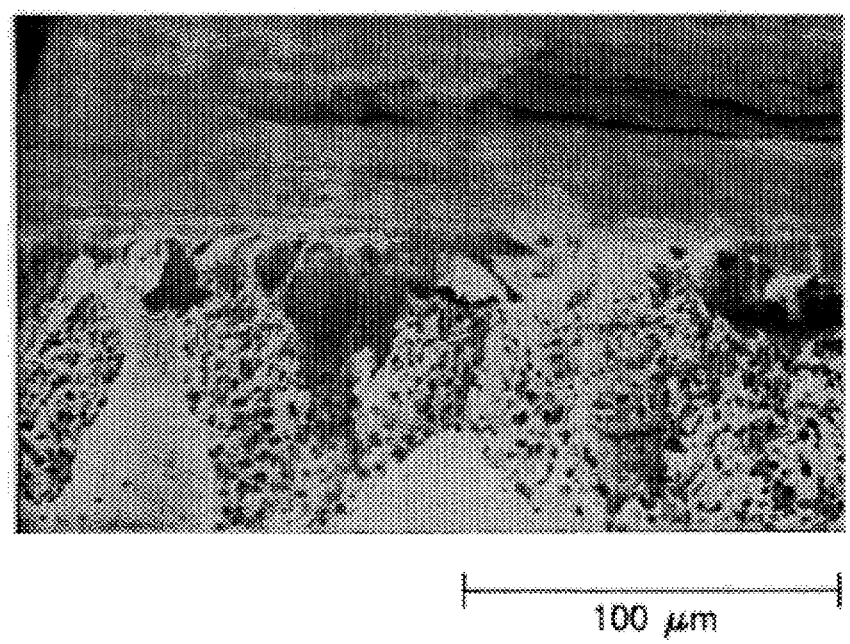
FIG. 22 shows an SEM of the cross section of a capsule wall made of a asymmetric membrane comprised of ethylcellulose and prepared in Example 27.

Capsules formed by the process described above had walls about 200 µm thick that were asymmetric in structure. Essentially the entire thickness of the capsule wall, including the inside surface of the capsule, was porous. The dense outer skin was less than 1 µm thick and, as shown in FIG. 22, was continuous and imperforate.

These capsules were loaded with 200 mg of a powder mixture that contained 5 wt % glipizide (a diabetes drug) and 95 wt % tromethamine. The loaded capsules were sealed at the junction of the trimmed end of the cap and the capsule body with a narrow band of solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, the loaded capsules were placed in a stirred solution of simulated intestinal buffer (osmotic pressure of 7 atm and pH of 7.5) at 37° C. About 70% of the glipizide was released at a constant rate—a release pattern that is typical of osmotic-delivery systems. The steady-state release rate of glipizide (during the period of constant release) was 0.63±0.08 mg/hr.

EXAMPLE 28

Formation of Asymmetric-Membrane Capsules Made With Cellulose Acetate Butyrate

Capsules with asymmetric-membrane walls were made from a coating solution of 15 wt % cellulose acetate butyrate (CAB 381-20, Eastman Chemicals, Kingsport, Tenn.), 30 wt % ethanol, and 5 wt % glycerol dissolved in acetone.

Capsules were made using two sizes of mandrels—one size for the capsule cap and one size for the capsule body. The mandrels were immersed in room-temperature coating solution and were withdrawn slowly, taking 9 seconds to completely withdraw the mandrels. The coated mandrels were exposed to room-temperature air for 7 seconds and then immersed in a room-temperature quench bath that contained 5 wt % glycerol in water. The coated mandrels were removed from the quench bath after 30 minutes, and the capsule caps and bodies removed from the mandrels by sliding a tight collar down each mandrel to force the caps and bodies off the mandrels. The capsule caps and bodies were dried in room-temperature air for at least 12 hours and then trimmed to the desired lengths.

Figure 23:
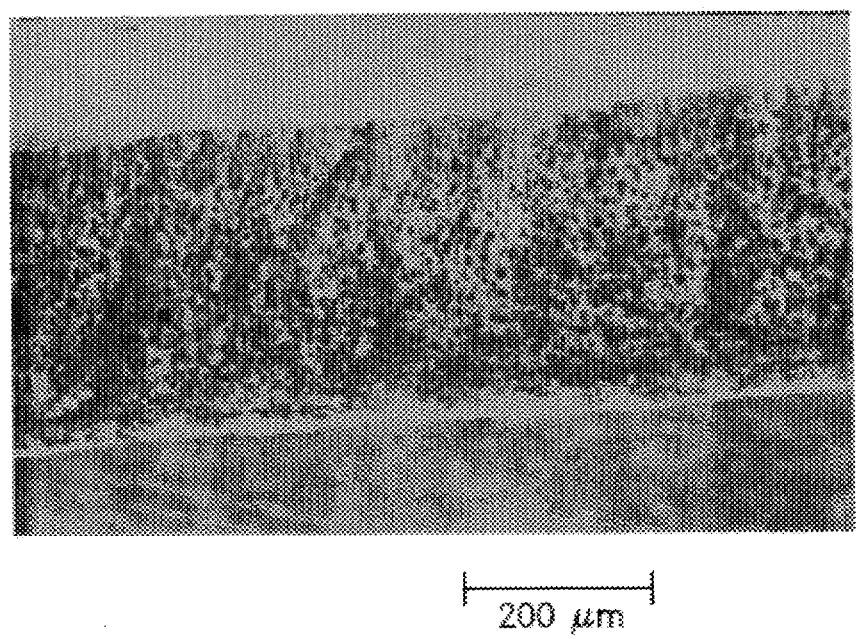
FIG. 23 shows the SEM of a cross section capsule wall made of a cellulose acetate butyrate asymmetric membrane as prepared in Example 28.

Capsules formed by the process described above had walls about 250 µm thick that were asymmetric in structure. Essentially the entire thickness of the capsule wall, including the inside surface of the capsules, was porous. The dense outer skin was less than 1 µm thick and, as shown in FIG. 23, was continuous and imperforate.

These capsules were loaded with 200 mg of a powder mixture that contained 10 wt % glipizide (a diabetes drug) and 90 wt % tromethamine. The loaded capsules were sealed at the junction of the trimmed end of the cap and the capsule body with a narrow band of a solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, the loaded capsules were placed in a stirred solution of simulated intestinal buffer (osmotic pressure of 7 atm and pH of 7.5) at 37° C. About 70% of the glipizide was released at a constant rate—a release pattern typical of osmotic-delivery systems. The steady-state release rate of glipizide (during the period of constant release) was 1.60±0.15 mg/hr.

EXAMPLE 29

Formation of Asymmetric-Membrane Capsules Made With A Blend of Ethylcellulose and Cellulose Acetate Capsules with asymmetric-membrane walls were made from a coating solution of 10 wt % ethylcellulose (Ethocel std-100, Dow Chemical, Midland, Mich.), 2 wt % cellulose acetate (CA 398-10, Eastman Chemicals, Kingsport, Tenn.), 30 wt % ethanol, and 10 wt % glycerol dissolved in acetone.

Capsules were made using two sizes of mandrels—one size for the capsule cap and one size for the capsule body. The mandrels were immersed in room-temperature coating solution and were withdrawn slowly, taking 9 seconds to completely withdraw the mandrels. The coated mandrels were exposed to room-temperature air for 7 seconds and then immersed in a room-temperature quench bath that contained 5 wt % glycerol in water. The coated mandrels were removed from the quench bath after 30 minutes, and the capsule caps and bodies removed from the mandrels by sliding a tight collar down each mandrel to force the caps and bodies off the mandrels. The capsule caps and bodies were dried in room-temperature air for at least 12 hours and then trimmed to the desired lengths.

Capsules formed by the process described above had walls about 200 µm thick that were-asymmetric in structure. Scanning electron microphotographs (SEMs) showed that in some areas CA had separated from the Ethocel, forming dispersed spheres throughout the membrane, as shown in FIG. 24. The incompatibility between the two polymers also caused macropores to form in the surface of the membrane. These macropores can function as drug-delivery ports. Thus, blending two incompatible polymers can be used to form asymmetric-membrane capsules or coatings that contain macropores in the surface.

These capsules were loaded with 200 mg of a powder mixture that contained 10 wt % glipizide (a diabetes drug) and 90 wt % N-methylglucamine. The loaded capsules were sealed at the junction of the trimmed end of the cap and capsule body with a narrow band of a solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, the loaded capsules were placed in a stirred solution of simulated intestinal buffer (osmotic pressure of 7 atm and pH of 7.5) at 37° C. About 70% of the glipizide was released at a constant rate—a release pattern that is typical of osmotic-delivery systems. The steady-state release rate of glipizide (during the period of constant release) was 2.2±0.2 mg/hr.

EXAMPLE 30

Formation of Asymmetric-Membrane Capsules Made With A Blend of Cellulose Acetate Butyrate Ethylcellulose Capsules with asymmetric-membrane walls were made from a coating solution of 13 wt % cellulose acetate butyrate (CAB 381-20, Eastman Chemicals, Kingsport, Tenn.), 2 wt % ethylcellulose (Ethocel std-100, Dow Chemical, Midland, Mich.), 30 wt % ethanol, and 5 wt % glycerol dissolved in acetone.

Capsules were made using two sizes of mandrels—one size for the capsule cap and one size for the capsule body. The mandrels were immersed in room-temperature coating solution and were then withdrawn slowly, taking 7 seconds to completely withdraw the mandrels. The coated mandrels were exposed to room-temperature air for 7 seconds and then immersed in a room-temperature quench bath that contained 5 wt % glycerol in water. The coated mandrels were removed from the quench bath after 30 minutes, and the capsule bodies and caps were removed from the mandrels by sliding a tight collar down each mandrel to force the caps and bodies off the mandrels. The capsule bodies and caps were dried in room-temperature air for at least 12 hours and then trimmed to the desired lengths.

Figure 25:
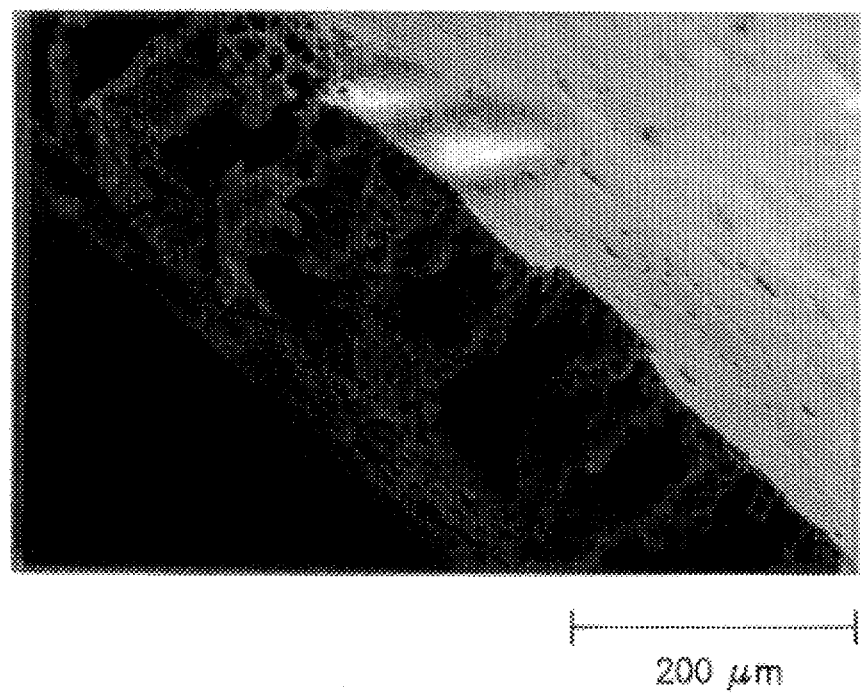
FIG. 25 shows the SEM of a cross section of a capsule wall made of a blend cellulose acetate butyrate and ethylcellulose asymmetric membrane (Example 30).

Capsule bodies and caps formed by the process described above had walls about 200 µm thick that were asymmetric in structure. Essentially the entire thickness of the capsule wall, including the inside surface of the capsule, was porous. The dense outer skin was less than 1 µm thick and had many dimples, as shown in FIG. 25. The dimples appear to contain macropores in the outer skin, which could serve as drug-delivery ports.

The capsules were loaded with 200 mg of a powder mixture that contained 10 wt % glipizide (a diabetes drug) and 90 wt % N-methylglucamine. The loaded capsules were sealed at the junction of the end of the cap and the capsule body with a narrow band of a solution containing 15 wt % cellulose acetate (CA 398-10, Eastman Chemical, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 37° C. About 70% of the glipizide was release at a constant rate—a release pattern that is typical of osmotic-delivery systems. The steady-state release rate of glipizide (during the period of constant release) was 1.25±0.05 mg/hr.

EXAMPLE 31

Formation of Asymmetric-Membrane Capsules Made With A Blend of Cellulose Acetate Butyrate and Cellulose Acetate Capsules with asymmetric-membrane walls were made from a coating solution of 12 wt % cellulose acetate butyrate (CAB 381-20, Eastman Chemicals, Kingsport, Tenn.), 3 wt % cellulose acetate (CA 398-10, Eastman Chemicals, Kingsport, Tenn.), 30 wt % ethanol, and 5 wt % glycerol dissolved in acetone.

Capsules were made using two sizes of mandrels—one size for the capsule cap and one size for the capsule body. The mandrels were immersed in 12° C. coating solution and were withdrawn slowly, taking 7 seconds to completely withdraw the mandrels. The coated mandrels were exposed to room-temperature air for 7 seconds and then immersed in a 42° C. quench bath that contained 5 wt % glycerol in water. The coated mandrels were removed from the quench bath after 30 minutes, and the capsule caps and bodies removed from the mandrels by sliding a tight collar down each mandrel to force the caps and bodies off the mandrels. The capsule caps and bodies were dried in room-temperature air for at least 12 hours and then trimmed to the desired lengths.

Figure 26:
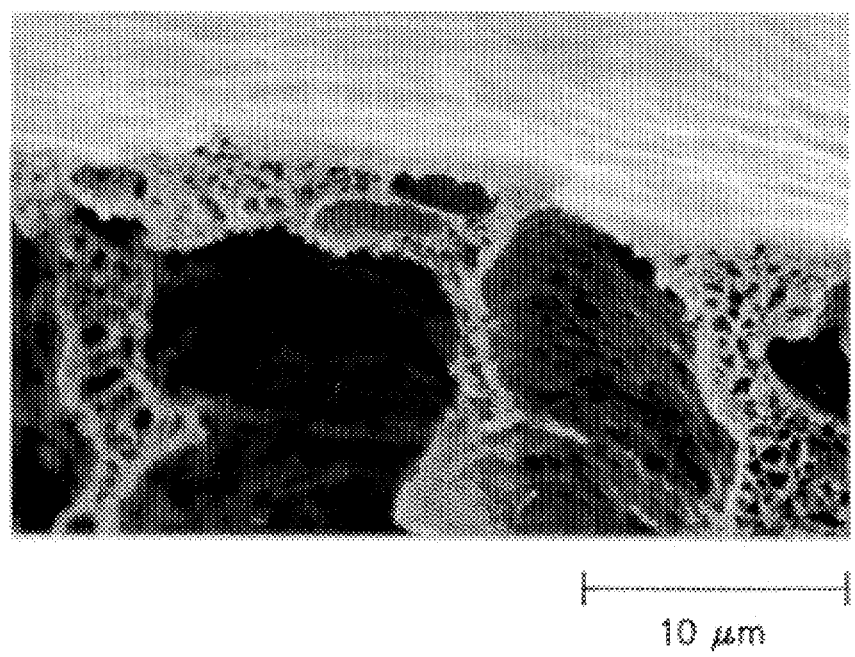
FIG. 26 shows the SEM of a cross section of an asymmetric membrane capsule wall made of a blend of cellulose acetate butyrate and cellulose acetate (Example 31).

Capsule bodies and caps formed by the process described above had walls about 300 μm thick that were asymmetric in structure. Essentially the entire thickness of the capsule wall, including the inside surface of the capsule, was porous. The dense outer skin was less than 1 μm thick and, as shown in FIG. 26, was continuous and imperforate.

The capsules were loaded with 200 mg of a powder mixture that contained of 10 wt % glipizide (an anti-diabetes drug) and 90 wt % N-methylglucamine. The loaded capsules were sealed at the junction of the trimmed end of the cap and the capsule body with a narrow band of a solution containing 15 wt % cellulose acetate (CA 398-10, Eastman Chemicals, Kingsport, Tenn.), 8 wt % glycerol, and 25% ethanol dissolved in acetate. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 7° C. About 70% of the glipizide was released at a constant rate—a release pattern that is typical of osmotic-delivery systems. The steady-state release rate of glipizide (during the period of constant release) was 2.91±0.22 mg/hr.

EXAMPLE 32

Formation of Asymmetric-Membrane Capsules Made With Cellulose Acetate Propionate Capsules with asymmetric-membrane walls were made from a solution of 34 wt % cellulose acetate propionate (CAP 482-0.5, Eastman Chemicals, Kingsport, Tenn.), and 10 wt % glycerol dissolved in acetone.

Capsules were made using two sizes of mandrels—one size for the capsule cap and one size for the capsule body. The mandrels were immersed in room-temperature coating solution and were withdrawn slowly, taking 9 seconds to completely withdraw the mandrels. The coated mandrels were exposed to room-temperature air for 3 seconds and then immersed in a room-temperature quench bath that contained 15 wt % glycerol in water. The coated mandrels were removed from the quench bath after 30 minutes, and the capsule caps and bodies were removed from the mandrels by sliding a tight collar down each mandrel to force the caps and bodies off the mandrels. The capsule caps and bodies were trimmed to the desired lengths and then dried in room-temperature air for at least 12 hours.

Figure 27:
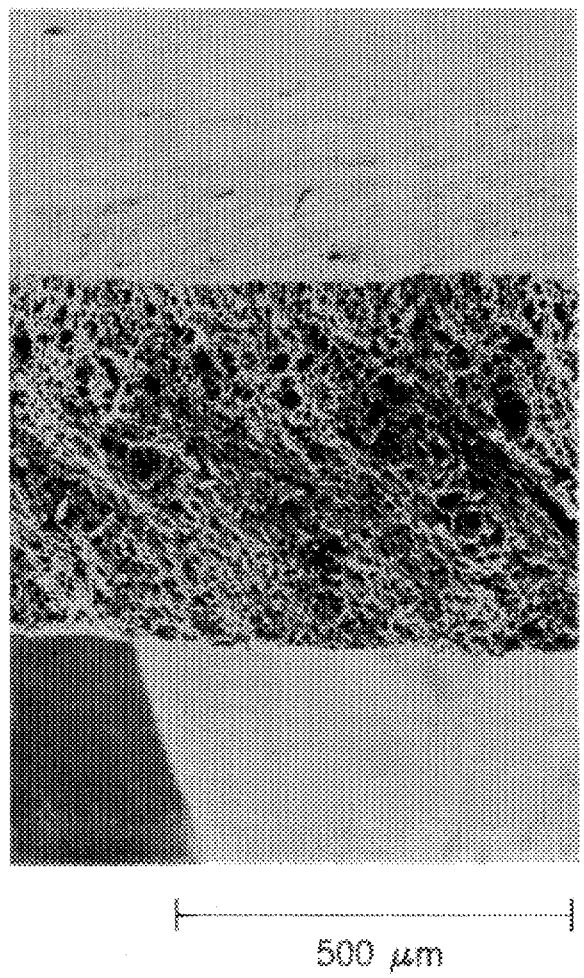
FIG. 27 shows the SEM of a cross section of an asymmetric membrane capsule wall made of cellulose acetate propionate, prepared according to Example 32.

Capsules formed by the process described above had walls about 450 μm thick that were asymmetric in structure. Essentially the entire thickness of the capsule walls, including the inside surface of the capsules, was porous, as shown in FIG. 27. The dense outer skin was less than 1 μm thick and contained many macro-pores, which would function as drug-delivery ports.

EXAMPLE 33

Formation of Asymmetric-Membrane Capsules Made With Nitrocellulose

Capsules with asymmetric-membrane walls were made from a solution of 36.5 wt % nitrocellulose (nitrocellulose RS 18-25, Hercules, Inc., Wilmington, Del.), 13.5 wt % isopropanol, and 15 wt % glycerol dissolved in acetone.

Capsules were made using two sizes of mandrels—one size for the capsule cap and one size for the capsule body. The mandrels were immersed in room-temperature coating solution and were then withdrawn slowly, taking 10 seconds to completely withdraw the mandrels. The coated mandrels were exposed to room-temperature air for 7 seconds and then immersed in a room-temperature quench bath that contained 15 wt % glycerol in water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 28:
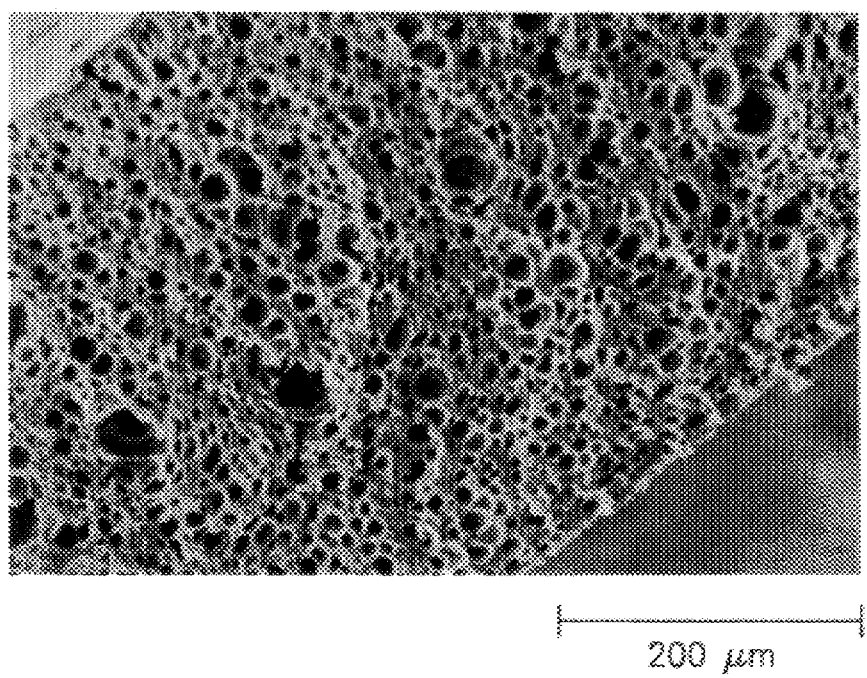
FIG. 28 shows the SEM of a cross section of an asymmetric membrane capsule wall made of nitro-cellulose, prepared by the procedure of Example 33.

Capsules formed by the process described above had walls about 400 μm thick that were asymmetric in structure. Essentially the entire thickness of the capsule walls, including the inside surface of the capsules, was porous, as shown in FIG. 28. The dense outer skin was less than 1 μm thick.

EXAMPLE 34

Formation of Asymmetric-Membrane Capsules Made With Cellulose Acetate Phthalate

Capsules with asymmetric-membrane walls were made from a solution of 23.6 wt % cellulose acetate phthalate (CAPh, Eastman Chemicals, Kingsport, Tenn.), 25.5 wt % ethanol, and 7.3 wt % glycerol dissolved in acetone.

Capsules were made using two sizes of mandrels—one size for the capsule cap and one size for the capsule body. The mandrels were immersed in room-temperature coating solution and were withdrawn slowly, taking 7 seconds to completely withdraw the mandrels. The coated mandrels were exposed to room-temperature air for 7 seconds and then immersed in a room-temperature quench bath that contained water acidified with a few drops of sulfuric acid. The coated mandrels were removed from the quench bath after 30 minutes, and the capsule caps and bodies were removed from the mandrels by sliding a tight collar down each mandrel to force the caps and bodies off the mandrels.

The capsule caps and bodies were dried in room-temperature air for at least 12 hours and then trimmed to the desired lengths.

Figure 29:
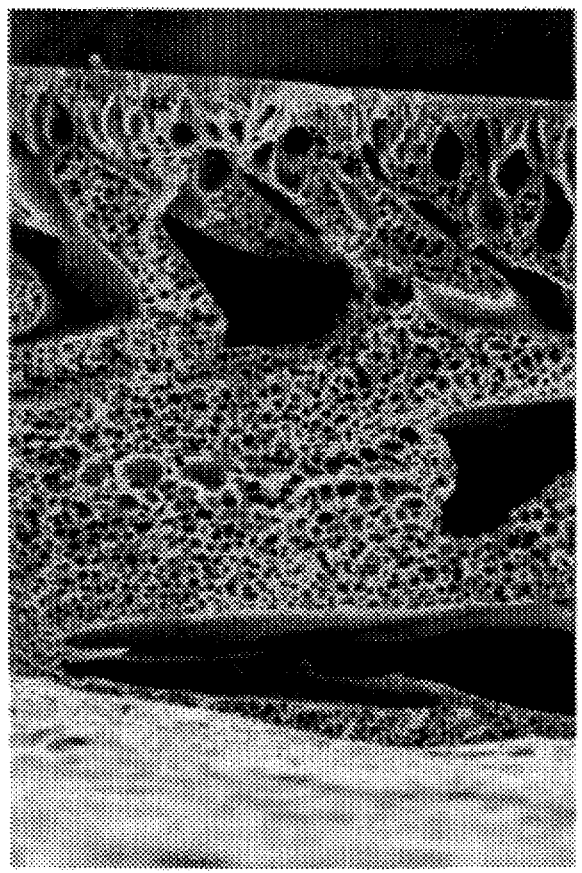
FIG. 29 shows the SEM of a cross section of an asymmetric membrane capsule wall made of cellulose acetate phthalate, prepared according to Example 34.
Figure 30:
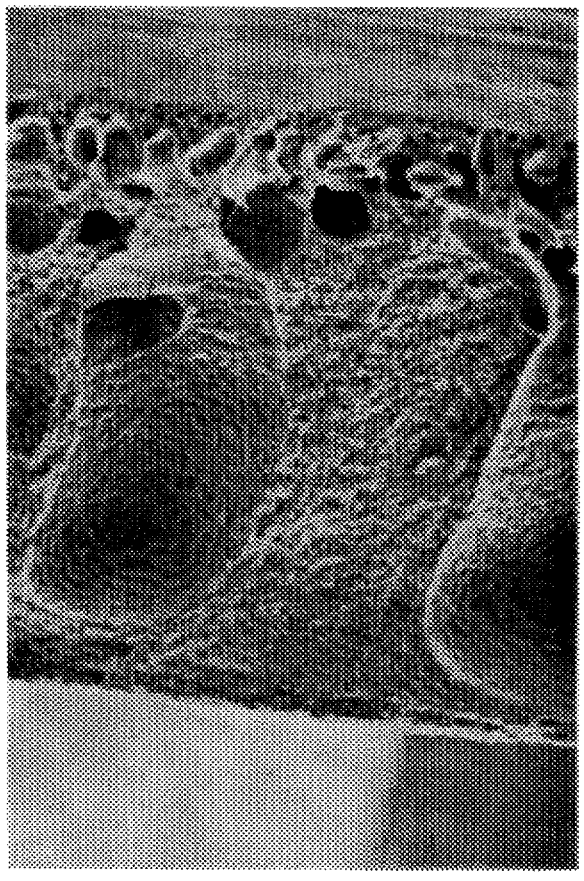
FIG. 30 shows the SEM of a cross section of an asymmetric membrane capsule wall made of cellulose acetate trimellitate, prepared by the procedure of Example 35.

Capsules formed by the process described above had walls about 200 μm thick that were asymmetric in structure. Essentially the entire thickness of the capsule walls, including the inside surface of the capsules, was porous, as shown in FIG. 29. The dense outer skin was less than 1 μm thick and was continuous and imperforate.

EXAMPLE 36

Formation of Asymmetric-Membrane Capsules Made With Polyvinyl Alcohol

Capsules with asymmetric-membrane walls were made from a coating solution of 15 wt % polyvinyl alcohol (Elvanol 71-30, Dupont, Wilmington, Del.), and 20 wt % ethanol dissolved in water.

Capsules were made using two sizes of mandrels—one size for the capsule cap and one size for the capsule body. The mandrels were immersed in 70° C. coating solution and were withdrawn slowly, taking 10 seconds to completely withdraw the mandrels. The coated mandrels were exposed to room-temperature air for 7 seconds and then immersed in a room-temperature quench bath that contained 70 wt % acetone and 30 wt % water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 31:
FIG. 31 shows the SEM of a cross section of an asymmetric membrane capsule wall made of polyvinyl alcohol by the procedure of Example 36.

Capsules formed by the process described above had walls about 350 μm thick that were asymmetric in structure. Most of the thickness of the capsule walls, including the inside surface of the capsules, was porous, as shown in FIG. 31. The dense outer skin was approximately 50 μm thick and continuous and imperforate.

These capsules were loaded with 200 mg of a powder mixture that contained 10 wt % glipizide (a diabetes drug) and 90 wt % N-methylglucamine. The loaded capsules were sealed at the junction of the trimmed end of the cap and the capsule body with a narrow band of a solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 37° C. About 90% of the glipizide was released at a constant rate—a release pattern typical of osmotic-delivery systems. The steady-state release rate of glipizide (during the period of constant release) was 6.04±0.48 mg/hr.

EXAMPLE 37

Formation of Asymmetric-Membrane Capsules Made With Ethylenevinyl Alcohol

Capsules with asymmetric-membrane walls were made from a coating solution of 15 wt % ethylenevinyl alcohol (EVAL F-101, EVAL Co. of America, Omaha, Nebr.), 55 wt % ethanol, and 30 wt % water.

Capsules were made using two sizes of mandrels—one size for the capsule cap and one size for the capsule body. The mandrels were immersed in 40° C. coating solution and were withdrawn slowly, taking 7 seconds to completely withdraw the mandrels. The coated mandrels were exposed to room-temperature air for 7 seconds and then immersed in a room-temperature quench bath that contained water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 32:
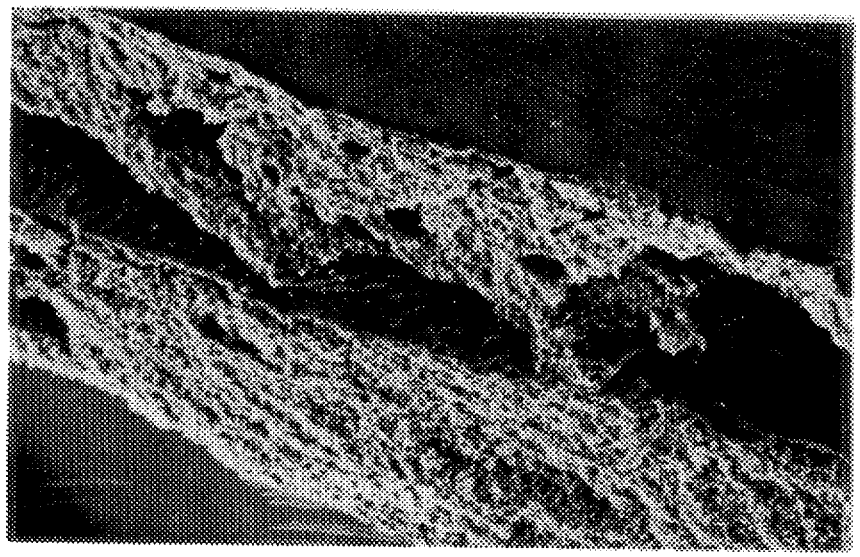
FIG. 32 shows the SEM of a cross section of an asymmetric membrane capsule wall made of ethylenevinyl alcohol, prepared according to Example 37.

Capsules formed by the process described above had walls about 200 μm thick that were asymmetric in structure. Essentially the entire thickness of the capsule walls, including the inside surface of the capsules, was porous, as shown in FIG. 32. The dense outer skin was less than 1 μm thick and was continuous and imperforate.

These capsules were loaded with 200 mg of a powder mixture that contained 10 wt % glipizide (a diabetes drug) and 90 wt % tromethamine. The loaded capsules were sealed at the junction of the trimmed end of the cap and the capsule body with a narrow band of a solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 37° C. About 70% of the glipizide was released at a constant rate—a release pattern that is typical of osmotic-delivery systems. The steady-state release rate of glipizide (during the period of constant release) was 6.47±0.31 mg/hr.

EXAMPLE 38

Formation of Asymmetric-Membrane Capsules Made With Polyurethane

Capsules with asymmetric-membrane walls were made from a coating solution of 24.5 wt % polyurethane (Tuftane 310, Lord Corp, Erie, Pa.) dissolved in dimethylformamide.

Capsules were made using two sizes of mandrels—one size for the capsule cap and one size for the capsule body. The mandrels were immersed in room-temperature coating solution and were withdrawn slowly, taking 11 seconds to completely withdraw the mandrels. The coated mandrels were exposed to room-temperature air for 7 seconds and then immersed in a room-temperature quench bath that contained water. The coated mandrels were removed from the quench bath after 30 minutes, and the capsule caps and bodies were removed from the mandrels by sliding a tight collar down each mandrel to force the caps and bodies of the mandrels. The capsule caps and bodies were dried in room-temperature air for at least 12 hours and then trimmed to the desired lengths.

Figure 33:
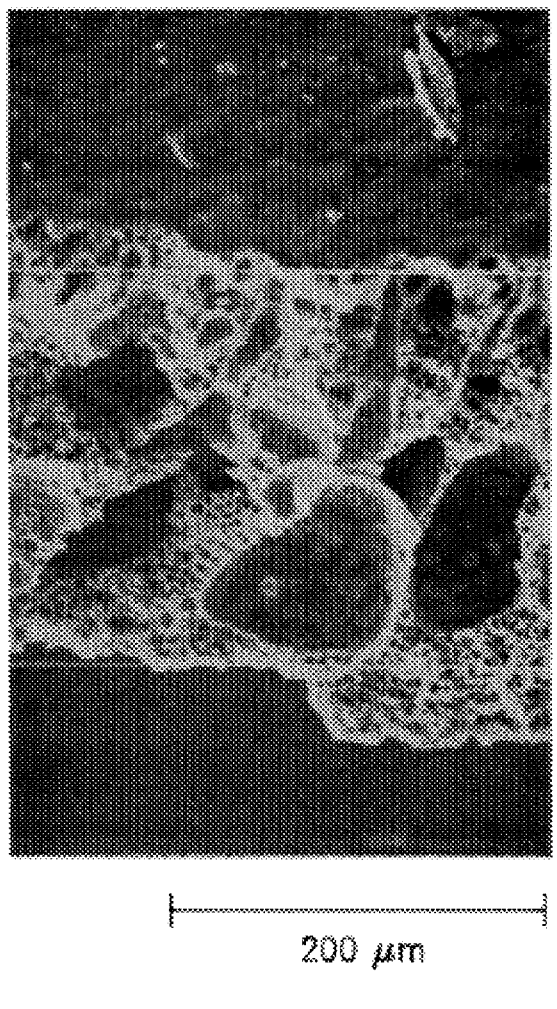
FIG. 33 shows an SEM of a cross section of an asymmetric membrane capsule wall made of polyurethane by the prcedure of Example 38.

Capsules formed by the process described above had walls about 200 μm thick that were asymmetric in structure. Essentially the entire thickness of the capsule walls, including the inside surface of the capsules, was porous, as shown in FIG. 33. The dense outer skin was less than 1 μm thick and was continuous and imperforate.

These capsules were loaded with 200 mg of a powder mixture that contained 10 wt % glipizide (a diabetes drug) and 90 wt % N-methylglucamine. The loaded capsules were sealed at the junction of the trimmed end of the cap and the capsule body with a narrow band of a solution containing 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 37° C. About 70% of the glipizide was released at a constant rate—a release pattern that is typical of osmotic-delivery systems. The steady-state release rate of glipizide (during the period of constant release) was 0.62±0.04 mg/hr.

EXAMPLE 39

Formation of Asymmetric-Membrane Capsules Made With Polyvinylidene Fluoride

Capsules with asymmetric-membrane walls were made from a coating solution of 15 wt % polyvinylidene fluoride (Kynar 460, Pennwalt Corp., Philadelphia, Pa.) dissolved in dimethylformamide.

Capsules were made using two sizes of mandrels—one size for the capsule cap and one size for the capsule body. The mandrels were immersed in room temperature coating solution and were withdrawn slowly, taking 7 seconds to completely withdraw the mandrels. The coated mandrels were exposed to room-temperature air for 7 seconds and then immersed in a room-temperature quench bath that contained water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 34:
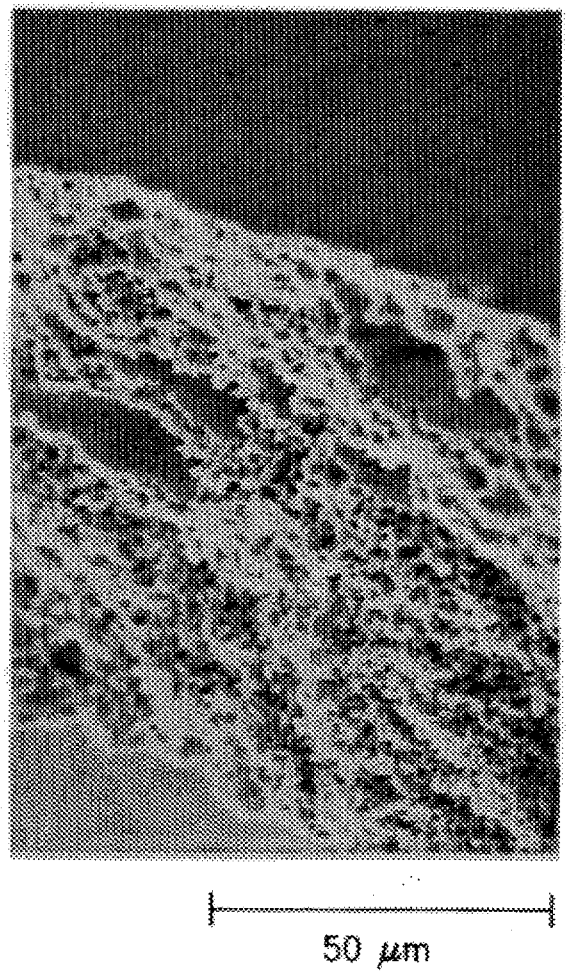
FIG. 34 shows the SEM of a cross section of an asymmetric membrane capsule wall made of polyvinylidene fluoride, prepared by the procedure of Example 39.

Capsules formed by the process described above had walls about 100 μm thick that were asymmetric in structure. Essentially the entire thickness of the capsule walls, including the inner surface of the capsules, was porous, as shown in FIG. 34. The outer skin was covered with many pores less than 1 μm in diameter.

These capsules were loaded with 200 mg of a powder mixture that contained 10 wt % glipizide (a diabetes drug) and 90 wt % N-methylglucamine. The loaded capsules were sealed at the junction of the trimmed end of the cap and the capsule body with a narrow band of a solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 37° C. About 70% of the glipizide was released at a constant rate—a release pattern that is typical of osmotic-delivery systems. The steady-state release rate of glipizide (during the period of constant release) was 0.67±0.06 mg/hr.

EXAMPLE 40

Formation of Asymmetric-Membrane Capsules Made With Polysulfone

Capsules with asymmetric-membrane walls were made from a coating solution of 21.4 wt % polysulfone (Udel 1700, Union Carbide, Danbury, Conn.) dissolved in dimethylformamide.

Capsules were made using two sizes of mandrels—one size for the capsule cap and one size for the capsule body. The mandrels were immersed in room-temperature coating solution and were withdrawn slowly, taking 4 seconds to completely withdraw the mandrels. The coated mandrels were exposed to room-temperature air for 7 seconds and then immersed in a room-temperature quench bath that contained water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 35:
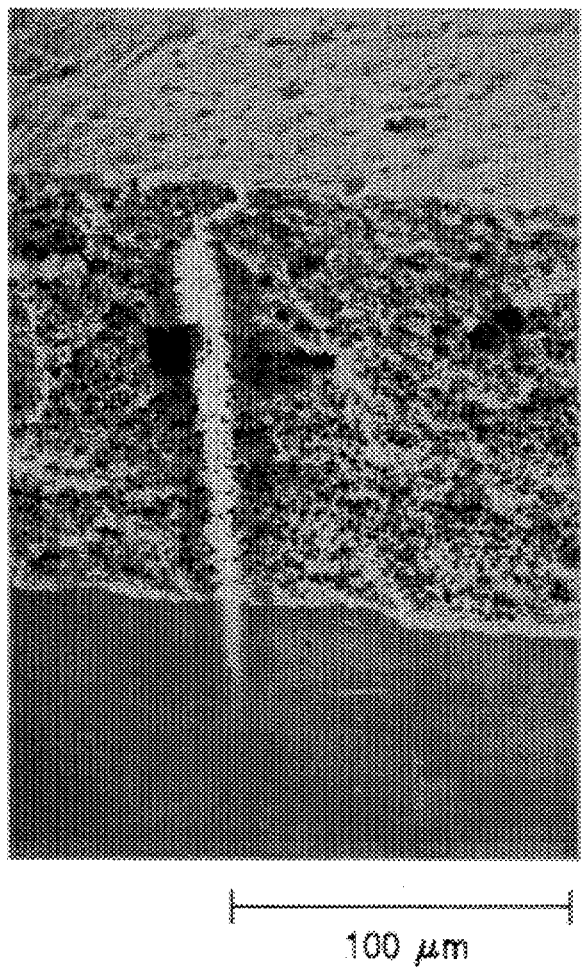
FIG. 35 shows the SEM of a cross section of an asymmetric membrane capsule wall made of polysulfone, prepared according to Example 40.

Capsules formed by the process described above had walls about 150 μm thick that were asymmetric in structure. Essentially the entire thickness of the capsule walls, including the inside surface of the capsule, was porous, as shown in FIG. 35. The dense outer skin was less than 1 μm thick and was continuous and imperforate.

These capsules were loaded with 200 mg of a powder mixture that contained 10 wt % glipizide (a diabetes drug) and 90 wt % N-methylglucamine. The loaded capsules were sealed at the junction of the trimmed end of the cap and the capsule body with a narrow band of a solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 37° C. The steady-state release rate of glipizide (during the period of constant release) was 0.42±0.03 mg/hr.

EXAMPLE 41

Formation of Asymmetric-Membrane Capsules Made With Polymethyl Methacrylate

Capsules with asymmetric-membrane walls were made from a coating solution of 25 wt % polymethyl methacrylate (PMMA V-920, Rohm and Haas, Philadelphia, Pa.), and 10 wt % polyethylene glycol dissolved in acetone.

Capsules were made using two sizes of mandrels—one size for the capsule cap and one size for the capsule body. The mandrels were immersed in room-temperature coating solution and were withdrawn slowly, taking 7 seconds to completely withdraw the mandrels. The coated mandrels were exposed to room-temperature air for 10 seconds and then immersed in a room-temperature quench bath that contained water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 36:
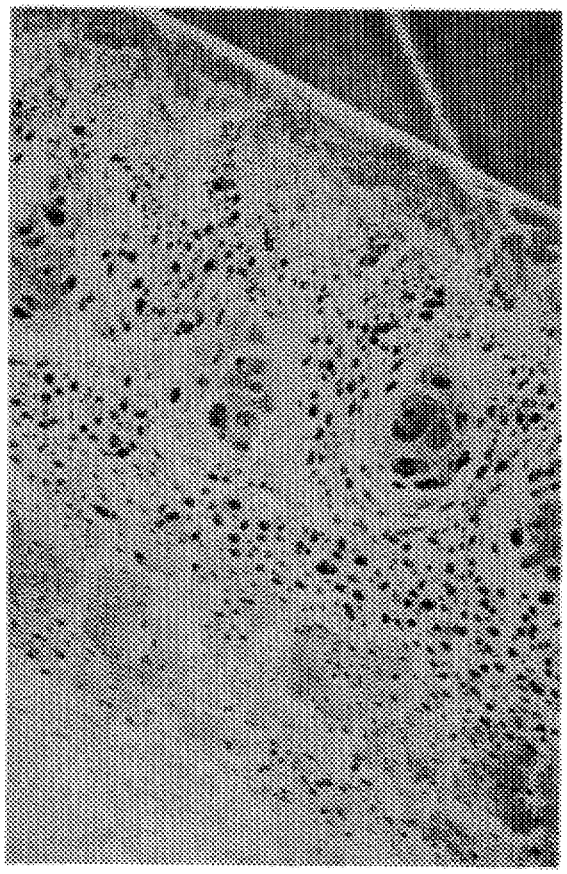
FIG. 36 shows the SEM of the cross section of an asymmetric membrane capsule wall made of polymethyl methacrylate by the procedure of Example 41.

Capsules formed by the process described above had walls about 200 μm thick that were asymmetric in structure. Most of the thickness of the capsule walls, including the inside surface of the capsules, was porous, as shown in FIG. 36. The dense outer skin was about 5 μm thick and was continuous and imperforate.

EXAMPLE 42

Formation of Asymmetric-Membrane Capsules Made With Polyamide

Capsules with asymmetric-membrane walls were made from a coating solution of 25 wt % polyamide (Elvamide 8063, Dupont, Wilmington, Del.), 19 wt % water, and 56 wt % ethanol.

Capsules were made using two sizes of mandrels—one size for the capsule cap and one size for the capsule body. The mandrels were immersed in room-temperature coating solution and were withdrawn slowly, taking 20 seconds to completely withdraw the mandrels. The coated mandrels were exposed to room-temperature air for 7 seconds and then immersed in a room-temperature quench bath that contained water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 37:
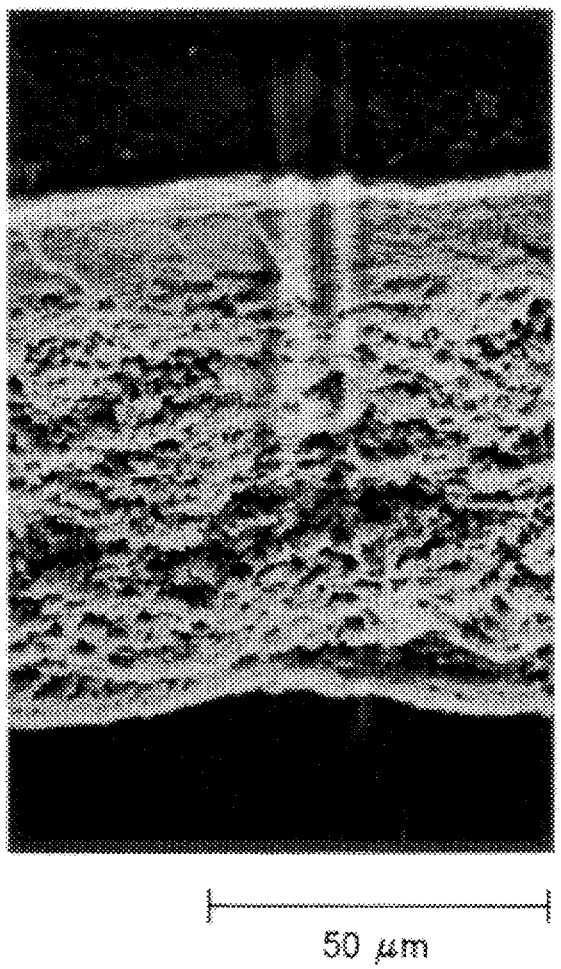
FIG. 37 shows the SEM of a cross section of an asymmetric membrane capsule wall made of polyamide by the procedure of Example 42.

Capsules formed by the process described above had walls about 100 μm thick that were asymmetric in structure. Most of the thickness of the capsule walls, including the inside surface of the capsules, was porous, as shown in FIG. 37. The dense outer skin was about 11 μm thick and was continuous and imperforate.

These capsules were loaded with 200 mg of a powder mixture that contained 10 wt % glipizide (a diabetes drug) and 90 wt % N-methylglucamine. The loaded capsules were sealed at the junction of the trimmed end of the cap and the capsule body with a narrow band of a solution that contained 15 wt % cellulose acetate (CA 398-10, Eastman Chemicals, Kingsport, Tenn.), 8 wt % glycerol, and 25 wt % ethanol dissolved in acetone. The volatile solvents were evaporated, leaving a cellulose acetate seal that prevented the capsule cap and body from separating during release-rate tests.

For release-rate tests, loaded capsules were placed in a stirred solution of simulated intestinal buffer (osmotic pressure of 7 atm and pH of 7.5) at 37° C. The steady-state release rate of glipizide (during the period of constant release) was 0.10±0.03 mg/hr.

EXAMPLE 43

Formation of Asymmetric-Membrane Capsules Made With A Blend of Ethylcellulose and Cellulose Acetate Phthalate Capsules with asymmetric-membrane walls were made from a coating solution of 10 wt % ethylcellulose (Ethocel std-100, Dow Chemicals, Midland, Mich.), 2 wt % cellulose acetate phthalate (CAPh, Eastman Chemicals, Kingsport, Tenn.), 30 wt % ethanol, and 10 wt % glycerol dissolved in acetone.

Capsules were made using two sizes of mandrels—one size for the capsule cap and one size for the capsule body. The mandrels were immersed in room-temperature coating solution and were withdrawn slowly, taking 9 seconds to completely withdraw the mandrels. The coated mandrels were exposed to room-temperature air for 7 seconds and then immersed in a room-temperature quench bath that contained 5 wt % glycerol in water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 38:
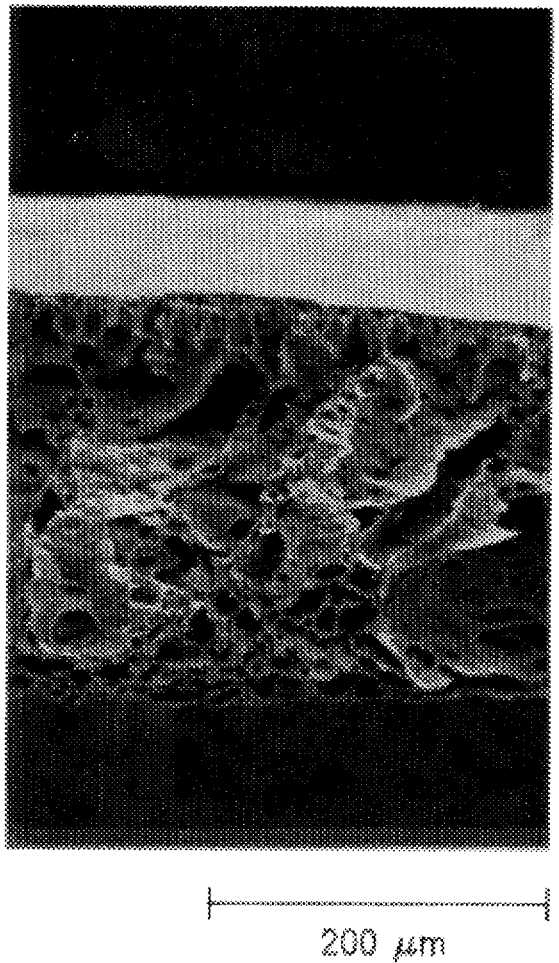
FIG. 38 shows the SEM of a cross section of an asymmetric membrane capsule wall made of a blend of ethylcellulose and cellulose acetate phthalate by the procedure of Example 43.

Capsules formed by the process described above had walls about 250 μm thick that were asymmetric in structure. Essentially the entire thickness of the capsule walls, including the inner surface of the capsules, was porous, as shown in FIG. 38. The dense outer skin had macropores on the surface, which could serve as drug-delivery ports. The macropores were typically less than 1 μm in diameter.

EXAMPLE 44

Formation of Asymmetric-Membrane Capsules Made With A Blend of Ethylcellulose and Cellulose Acetate Trimellitate Capsules with asymmetric-membrane walls were made from a coating solution of 10 wt % ethylcellulose (Ethocel std-100, Dow Chemicals, Midland, Mich.), 2 wt % cellulose acetate trimellitate (CAT, Eastman Chemicals, Kingsport, Tenn.), 30 wt % ethanol, and 10 wt % glycerol dissolved in acetone.

Capsules were made using two sizes of mandrels—one size for the capsule cap and one size for the capsule body. The mandrels were immersed in room-temperature coating solution and were withdrawn slowly, taking 9.seconds to completely withdraw the mandrels. The coated mandrels were exposed to room-temperature air for 7 seconds and then immersed in a room-temperature quench bath that contained 5 wt % glycerol in water. The coated mandrels were removed from the quench bath after 30 minutes, and the capsule caps and bodies were removed from the mandrels by sliding a tight collar down each mandrel to force the caps and bodies off the mandrels. The capsule caps and bodies were dried in room-temperature air for at least 12 hours and then trimmed to the desired lengths.

Figure 39:
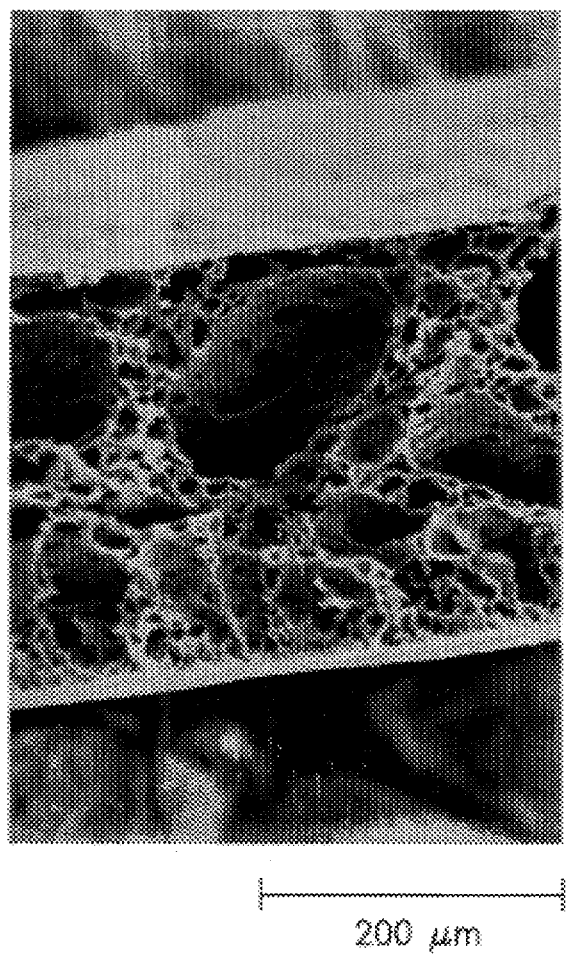
FIG. 39 shows the SEM of a cross section of an asymmetric membrane capsule wall made of a blend of ethylcellulose and cellulose acetate trimellitate by the procedure of Example 44.

Capsules formed by the process described above had walls about 250 μm thick that were asymmetric in structure. Essentially the entire thickness of the capsule walls, including the inside surface of the capsules, was porous, as shown in FIG. 39. The dense outer skin appeared to have macropores through the surface, which could serve as drug-delivery ports. The macropores were typically less than 1 μm in diameter.

EXAMPLE 45

Asymmetric-Membrane Coatings Made Of Ethylcellulose On Drug-Containing Beads

Asymmetric-membrane coatings were applied to drug-containing beads (30 to 35 mesh, less than 1 mm in diameter) with the spray-coating process described in Examples 20 and 21 from the original patent application. The beads consisted of 11 wt % glipizide (a diabetes drug), 36 wt % sodium bicarbonate, 48 wt % N-methylglucamine and 5 wt % carboxymethyl cellulose.

The polymer solution contained 11 wt % ethylcellulose (Ethocel std-100, Dow Chemicals, Midland, Mich.), 14 wt % water, and 75 wt % acetone. The polymer solution was kept at 40° C. and the drying chamber was kept at 70° C. The beads were mixed with the polymer solution just upstream from the spray nozzle and the mixture was sprayed into the drying chamber to evaporate the solvent and to form the asymmetric coatings. The coating process was repeated (as described in Example 21) to apply a second asymmetric-membrane coating to the beads.

Figure 40:
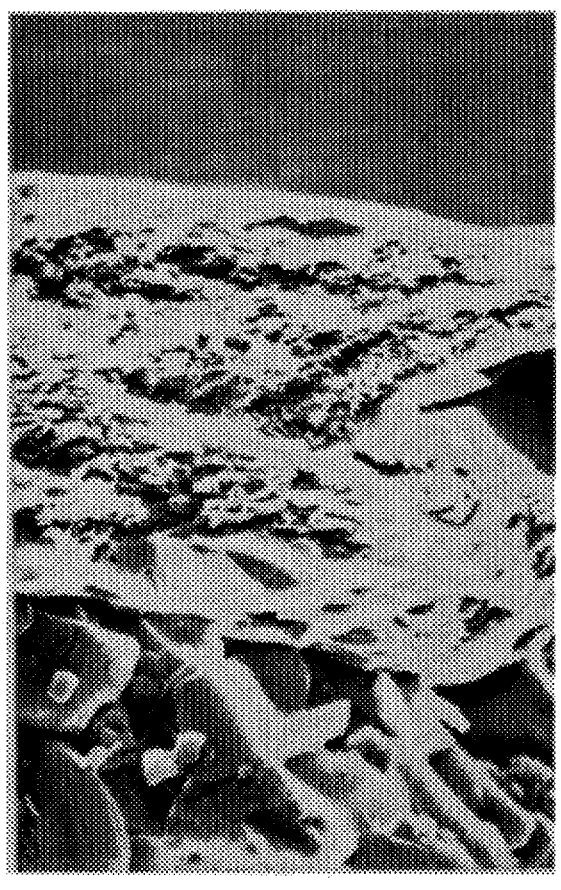
FIG. 40 shows the SEM of a cross section of an asymmetric membrane wall made of ethylcellulose on a drug containing bead, prepared by the procedure of Example 45.

The double-coated beads were covered with an asymmetric-membrane coating that was approximately 15 μm thick. The entire thickness of the coating was porous except for a dense outer skin, as shown in FIG. 40. The dense outer skin was less than 1 μm thick and was continuous and imperforate over the entire surface of the beads.

EXAMPLE 46

Asymmetric-Membrane Coatings Made of Cellulose Acetate Butyrate On Drug-Containing Beads Asymmetric-membrane coatings were applied to drug-containing beads (30 to 40 mesh, less than 1 mm in diameter) using the spray-coating process described in Examples 20 and 21. The beads were made using 11 wt % glipizide (a diabetes drug), 35 wt % lactose, 35 wt % cornstarch, 11 wt % N-methylglucamine, 5 wt % carboxymethyl cellulose and 3 wt % microcrystalline cellulose.

The polymer solution consisted of 31 wt % cellulose acetate butyrate (CAB 500-1, FMC Corp., Newark, Del.), 14 wt % methyl ethyl ketone, 3 wt % water and 52 wt % acetone. The polymer solution was kept at 45° C. and the drying chamber was kept at 80° C. The beads were mixed with the polymer solution just upstream from the spray nozzle and the mixture was sprayed into the drying chamber to evaporate the solvent and form the asymmetric coatings. The coating process (as described in Example 21) was repeated to apply a second asymmetric-membrane coating to the beads.

Figure 41:
FIG. 41 shows the SEM of a cross section of an asymmetric membrane wall made of cellulose acetate butyrate on a drug containing bead, and prepared according to Example 46.

The double-coated beads were covered with an asymmetric-membrane coating that was approximately 20 μm thick. Except for a dense outer skin, the entire thickness of the coating was porous, as shown in FIG. 41. The dense outer skin was less than 1 μm thick and was continuous and imperforate over the entire surface of the beads.

EXAMPLE 47

Water Fluxes Through Asymmetric-Membrane Capsule Walls Correspond to Drug-Release Rates Capsules with asymmetric-membrane walls were made with several different polymers, including polyvinyl alcohol (PVA), polyvinylidene fluoride (PVDF), and blends of cellulose acetate butyrate (CAB) and cellulose acetate; CAB and ethylcellulose (Ethocel); and Ethocel and CA. The capsules were made as described in Examples 29, 30, 31, 36 and 39.

To determine water fluxes for each type of asymmetric-membrane capsule, the capsule bodies were loaded with a powder mixture that contained 10 wt % glipizide (a diabetes drug) and 90 wt % N-methylglucamine. About half the uncapped capsule body was submerged in simulated intestinal buffer, with the open end of the capsule above the surface of the buffer. Due to the osmotic driving force, water was imbibed into the capsule bodies. The water imbibed into the capsule bodies was measured by weight gain until the solution inside the capsule body filled the capsule body and overflowed into the intestinal buffer.

Figure 42:
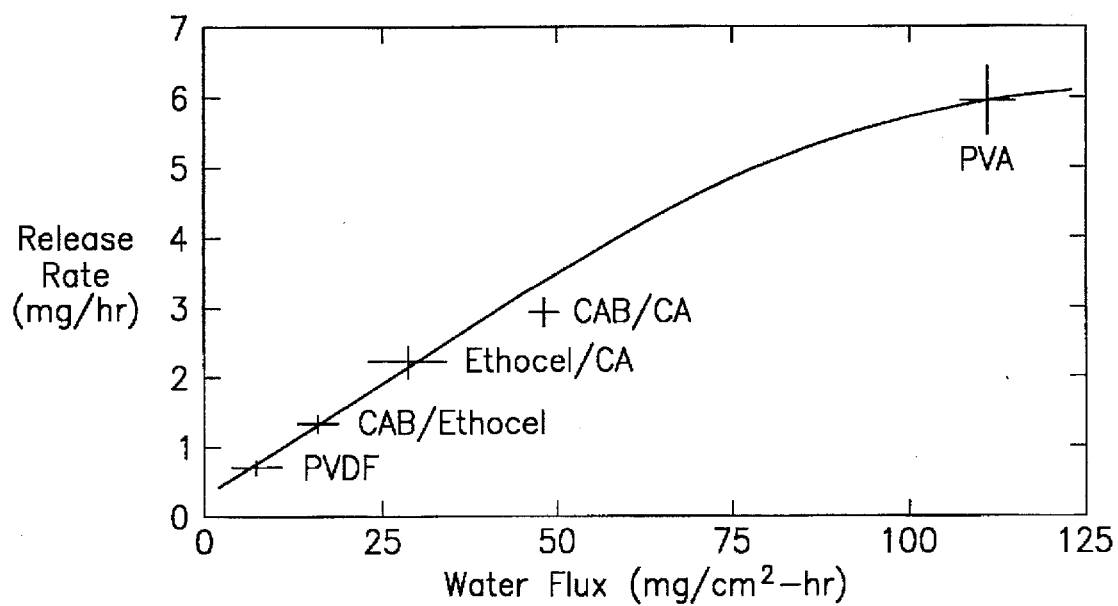
FIG. 42 shows water fluxes and corresponding release rates from various asymmetric membrane capsules prepared according to Example 47.

Release-rate tests, such as those described in Examples 29, 30, 31, 36 and 39, were conducted. The capsules were loaded with the same powder mixture as that used to load the capsule bodies for the water-flux tests. About 70% of the glipizide was released from all of the capsules at a constant rate. The steady-state release rate of glipizide (during the period of constant release) and the corresponding water flux is shown in FIG. 42 for each type of capsule. The release rates increase as the water fluxes through the asymmetric-membrane capsule walls increase, as predicted by osmotic theory. Thus, by using the asymmetric-membrane capsules with the proper permeability to water, the desired release rate can be achieved without changing the composition of the material loaded in the capsules.

EXAMPLE 48

Using standard techniques well known in the pharmaceutical industry, ⅜ inch modified ball shape tablets were prepared to contain:

| | |
|---|---|
| glipizide | 20.0 mg |
| N-methyl glucamine | 246.2 mg |
| microcrystalline cellulose | 69.2 mg |
| spray-dried lactose | 69.2 mg |
| hydroxypropyl cellulose | 8.5 mg |
| magnesium stearate | 10.9 mg |
| Total | 424.0 mg |

The tablets were coated in a commercial perforated pan coating machine (Freund Hi-Coater model HCT 30) using a coating solution of the following composition:

| | |
|---|---|
| acetone | 50.0 wt % |
| ethanol | 22.8 wt % |
| n-butanol | 12.4 wt % |
| water | 2.8 wt % |
| glycerol | 2.0 wt % |
| cellulose acetate 398-10 | 10.0 wt % |

The coating process was stopped after the tablets had received a coating equivalent to 42.4 mg cellulose acetate per tablet.

Upon examination with the scanning electron microscope, the tablet coating was seen to consist of a largely porous layer which accounted for most of the coating thickness, surmounted by a skin which was perforated by numerous pores, but which was much less porous in appearance than the substructure. When placed in a standard USP-II dissolution apparatus in USP simulated intestinal fluid, the tablets released glipizide at a controlled rate, with 50% of the total dose delivered in 3.5 hours and 90% delivered in 10–12 hours. When the tablets were dosed to fasted dogs, the plasma glipizide levels exhibited a broad sustained delivery over ~14 hours, attaining peak value in 11±2.8 hours. The tablets were recovered from the feces and assayed for remaining drug. The drug remaining in the tablets was 10±2% of the original dose. The bioavailability of the formulation relative to an oral sodium glipizide solution was 84%.

EXAMPLE 49

Non-pareil seeds (18–20 mesh) were placed in a 6 inch Wurster-type fluidized bed coating system (Lakso) and coated with a solution having the composition:

| | |
|---|---|
| cellulose acetate 398-10 | 5% |
| acetone | 55% |
| ethanol 95% USP | 40% |

After the beads had received coating equivalent to 4.7 wt % cellulose acetate, the batch was discharged and passed through a 16 mesh sieve. The 4.7% coated beads were returned to the coating equipment and additional coating was applied until the beads had received a total of 9.71% coating. The batch was discharged and the partition in the coating chamber was readjusted to obtain good fluidization. The batch was returned to the coating unit and coating resumed until the beads had received a total of 25% coating. Upon examination by scanning electron microscopy, the coating on the beads was observed to consist of several concentric layers of asymmetric membranes. The total thickness of the coating was ~55 μm. The external surface of the coating appeared smooth and imperforate at a magnification of 4000×.

EXAMPLE 50

The following pseudoephedrine formulation was prepared as 1 mm beads by the technique of extrusion/spheronization:

| | |
|---|---|
| pseudoephedrine | 50.0% |
| N-methyl glucamine | 20.0% |
| lactose | 15.0% |
| microcrystalline cellulose | 7.5% |
| starch 1500 | 7.5% |

The drug-containing beads were coated in the Wurster coater as in Example 49. Samples of coated beads were withdrawn from the coating equipment after they had received coatings of 15%, 30% and 45%. Upon microscopic examination, the coatings were found to consist of concentric layers (FIG. 43) of asymmetric membranes, as in the previous example. The overall thickness of the coating was 40 µm for the 15% coating weight, 60 µm for the 30% coating, and 70 µm for the 45% coating. When tested in a USP dissolution tester in water at 37° C., the 15% coated beads released 80% of their drug load in ~2 hours, while the 45% coated beads released 50% of their drug load in 4 hours and 80% of their drug load in 21 hours.

EXAMPLE 51

Capsules with asymmetric membranes were prepared by a semiautomated robotic process using a customized laboratory robot (Zymate II, Zymark, Hopkinton, Mass.). Six dip-fixtures each fitted with a stripping plate and fourteen aluminum moldpins were lubricated with silicone oil and dipped into a coating solution. The fixtures were withdrawn slowly over 8 seconds, rotated twice in order to evenly distribute the coating solution over the entire surface, and then lowered into a quench bath. After 15 minutes in the quench bath, the coated mandrels were withdrawn and dried at room temperature for about 30 minutes. After the drying step, the capsule shells were stripped off the pins using the stripping plate, trimmed to size using a trimmer, and joined manually. Half of the fixtures had mold-pins corresponding to capsule bodies and the other half had pins corresponding to capsule caps. The capsule dosage form was assembled by filling the capsule body with a powder composition consisting of an active agent and other excipients, and sealing the interface between the capsule body and cap (Quali-seal, Elanco, Ind.) using a sealing solution. The compositions of the coating, quench, and sealing solutions for capsules made from cellulose acetate (Form A) and from a mixture of ethylcellulose acetate and ethylcellulose (Form B) are given below in Table I.

The capsules were observed microscopically with a scanning electron microscope (SEM). The membrane was asymmetric with a relatively thin (6 µm) dense skin formed on the surface of the capsule that was away from the mold pin and a thick (100 µm) porous substrate on the inner surface which was in contact with the mold pin.

TABLE I

Composition of CA and EC/CA Capsules
Lubricant Polydimethyl Siloxane/Isopropyl Alcohol
Methylene Chloride

| | Coating | Quench | Sealing |
|---|---|---|---|
| FORM A (CA CAPSULES) | | | |
| Cellulose acetate | 15.0 | | 15.0 |
| Acetone | 49.0 | | 56.9 |
| Alcohol | 28.0 | | 28.0 |

TABLE I-continued

Composition of CA and EC/CA Capsules
Lubricant Polydimethyl Siloxane/Isopropyl Alcohol
Methylene Chloride

| | Coating | Quench | Sealing |
|---|---|---|---|
| Glycerol | 3.0 | 10.0 | |
| Triethylcitrate | 5.0 | | |
| Water | | 90.0 | |
| Dye | | | 0.1 |
| | 100.0 | 100.0 | 100.0 |
| FORM B (EC/CA CAPSULES) | | | |
| Cellulose acetate | 4.0 | | 15.0 |
| Ethylcellulose | 11.0 | | |
| Acetone | 49.0 | | 56.9 |
| Alcohol | 28.0 | | 28.0 |
| Glycerol | 3.0 | 10.0 | |
| Triethylcitrate | 5.0 | | |
| Water | | 90.0 | |
| Dye | | | 0.1 |
| | 100.0 | 100.0 | 100.0 |

EXAMPLE 52

Capsules were made from cellulose acetate as in Example 51 but with different ratios of glycerol/triethylcitrate. They were filled with a mixture of glipizide, meglumine, and sodium bicarbonate, and sealed according to the procedure described in Example 51. The formulation designations for the fill composition and membrane combinations are given in Table II. The release profile of glipizide from these formulations into 0.04 M TRIS are shown in FIG. 44.

TABLE II

MEMBRANE AND CORE FORMULATIONS - PLASTICIZER STUDY

A. MEMBRANE

Lubricant Polydimethyl Siloxane/Isopropyl Alcohol
Methylene Chloride

| Designation → | TEC08 | TEC53 | TEC62 |
|---|---|---|---|
| Cellulose acetate | 15.0 | 15.0 | 15.0 |
| Acetone | 49.0 | 49.0 | 49.0 |
| Alcohol | 28.0 | 28.0 | 28.0 |
| Glycerol | 8.0 | 3.0 | 2.0 |
| Triethylcitrate | 0.0 | 5.0 | 6.0 |
| | 100.0 | 100.0 | 100.0 |

B. CORE

| | a | b |
|---|---|---|
| Glipizide | 12.0 | 12.0 |
| Meglumine | 70.0 | 50.0 |
| Sodium Bicarbonate | 17.5 | 37.5 |
| Magnesium stearate | 0.5 | 0.5 |

C. FORMULATION

| Designation | Membrane | Core |
|---|---|---|
| TEC08 - a | TEC08 | a |
| TEC08 - b | TEC08 | b |
| TEC53 - a | TEC53 | a |
| TEC53 - b | TEC53 | b |
| TEC62 - b | TEC62 | b |

We claim:

1. A device for the controlled release of one or more active substances into an environment of use, said device comprising a core of said active substance or substances, with or without one or more excipients, surrounded by one or more asymmetric membranes, said assymmetric membrane comprising a thick, porous region which supports a dense, thin region.

2. A device of claim 1, wherein the membrane is permeable and imperforate and wherein the asymmetric membrane controls the release of the active substance or substances from the device.

3. A device of claim 1, wherein the membrane is permeable and perforate and wherein the asymmetric membrane controls the release of the active substance or substances from the device.

4. A device of claim 2, wherein the release is substantially osmotic pumping.

5. A device of claim 2, wherein the release is substantially diffusion.

6. A device of claim 3, wherein the release is substantially osmotic pumping.

7. A device of claim 3, wherein the release is substantially diffusion.

8. A device of claim 1, wherein the asymmetric membrane is a cellulose ester or ethyl cellulose.

9. A device of claim 1, wherein said substance or substances are biologically active.

10. A device of claim 1, which is a tablet.

11. A device of claim 1, which is a capsule.

12. A device of claim 1, which is a bead.

13. A device of claim 1, wherein the membrane is semipermeable and imperforate.

14. A device of claim 13, wherein the release is substantially osmotic pumping.

15. A device of claim 14, which is a capsule, tablet or bead.

16. A tablet, capsule or bead for administration to an animal which releases one or more pharmaceutically active substances into said animal which comprises a core of said active substance or substances, with or without one-or more pharmaceutically acceptable excipients, said core being surrounded by one or more asymmetric membranes, said asymmetric membrane comprising a thick, porous region which supports a dense, thin region.

17. A tablet, capsule or bead of claim 16, wherein the administration is oral and the release is into the fluid of the gastrointestinal tract of said animal and wherein the asymmetric membrane controls the release of the active substance or substances from the device.

18. A tablet, capsule or bead of claim 17, wherein the substance is an antihypertensive.

19. A tablet, capsule or bead of claim 18, wherein the substance as prazosin.

20. A tablet, capsule or bead of claim 18, wherein the substance is nifedipine.

21. A tablet, capsule or bead of claim 18, wherein the substance as trimazosin.

22. A tablet, capsule or bead of claim 18, wherein the substance as doxazosin.

23. A tablet, capsule or bead of claim 17, wherein the substance as an antianxiety agent.

24. A tablet, capsule or bead of claim 23, wherein the substance is hydroxyzine.

25. A tablet, capsule or bead of claim 23, wherein the substance as sertraline.

26. A tablet, capsule or bead of claim 17, wherein the substance as an anticlotting agent.

27. A tablet, capsule or bead of claim 26, wherein the substance is dazmegrel.

28. A tablet, capsule or bead of claim 17, wherein the substance is a blood-glucose lowering agent.

29. A tablet, capsule or bead of claim 28, wherein the substance is glipizide.

30. A tablet, capsule or bead of claim 17, wherein the substance is a decongestant, an antihistamine or cough or cold agent.

31. A tablet, capsule or bead of claim 30, wherein the substance is brompheniramine maleate.

32. A tablet, capsule or bead of claim 30, wherein the substance is chlorpheniramine maleate.

33. A tablet, capsule or bead of claim 30, wherein the substance is phenylephrine hydrochloride.

34. A tablet, capsule or bead of claim 30, wherein the substance is pseudoephedrine hydrochloride.

35. A tablet, capsule or bead of claim 30, wherein the substance is cetirizine.

36. A tablet, capsule or bead of claim 30, wherein the substance is dexbrompheniramine maleate.

37. A method for releasing one or more active substance or substances into an environment of use which comprises placing in said environment a device containing said active substance or substances surrounded by one or more asymmetric membranes, said asymmetric membrane comprising a thick, porous region which supports a dense, thin region.

38. A method of claim 37, wherein the device is a tablet, capsule or bead.

39. A method of claim 38, wherein the asymmetric membrane is permeable and imperforate or perforate and wherein the asymmetric membrane controls the release of the active substance or substances from the device.

40. A method of claim 39, wherein the releasing is substantially diffusion.

41. A method of claim 39, wherein the releasing is substantially osmotic pumping.

42. A method of claim 38, wherein the asymmetric membrane is semipermeable and imperforate.

43. A method of claim 42, wherein the releasing is substantially osmotic pumping.

44. A capsule device for the controlled release of one or more active substances into an environment of use, said device comprising a core of said active substance or substances, with or without excipients, enclosed in a capsule the top or bottom of which is comprised of one or more asymmetric membranes, said asymmetric membrane comprising a thick, porous region which supports a dense, thin region.

45. A device of claim 44, wherein the membrane is permeable and perforate or imperforate and wherein the asymmetric membrane controls the release of the active substance or substances from the device.

46. A device of claim 45, wherein the release is by osmotic pumping.

47. A device of claim 6 wherein the active substance is pseudoephedrine hydrochloride.

48. A device of claim 47 wherein the asymmetric membrane comprises a cellulose acetate and a glycol.

49. A device of claim 6 wherein the active substance is sertraline.

50. A device of claim 49 wherein the asymmetric membrane comprises a cellulose acetate and a glycol.

* * * * *